(12) United States Patent
Waycuilis et al.

(10) Patent No.: US 8,173,851 B2
(45) Date of Patent: May 8, 2012

(54) PROCESSES FOR CONVERTING GASEOUS ALKANES TO LIQUID HYDROCARBONS

(75) Inventors: John J. Waycuilis, Cypress, TX (US); William J. Turner, Seabrook, TX (US); Raphael Thomas, San Antonio, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 334 days.

(21) Appl. No.: 12/477,319

(22) Filed: Jun. 3, 2009

(65) Prior Publication Data

US 2009/0247796 A1   Oct. 1, 2009

Related U.S. Application Data

(63) Continuation-in-part of application No. 12/138,877, filed on Jun. 13, 2008, now Pat. No. 7,674,941, which is a continuation-in-part of application No. 12/112,926, filed on Apr. 30, 2008, now Pat. No. 8,008,535, which is a continuation of application No. 11/254,438, filed on Oct. 19, 2005, now abandoned, which is a continuation-in-part of application No. 11/101,886, filed on Apr. 8, 2005, now Pat. No. 7,348,464, which is a continuation-in-part of application No. 10/826,885, filed on Apr. 16, 2004, now Pat. No. 7,244,867.

(51) Int. Cl.
*C07C 1/00* (2006.01)

(52) U.S. Cl. ........ 585/408; 585/359; 585/649; 585/642; 585/733

(58) Field of Classification Search .................. None
See application file for complete search history.

(56) References Cited

U.S. PATENT DOCUMENTS

| | | | |
|---|---|---|---|
| 2,168,260 | A | 8/1939 | Heisel et al. |
| 2,246,082 | A | 6/1941 | Vaughan et al. |
| 2,488,083 | A | 11/1949 | Gorin et al. |
| 2,536,457 | A | 1/1951 | Mugdan |
| 2,666,024 | A | 1/1954 | Low et al. |
| 2,677,598 | A | 5/1954 | Crummett et al. |

(Continued)

FOREIGN PATENT DOCUMENTS

CA           1099656         4/1981

(Continued)

OTHER PUBLICATIONS

Olah et al.; Hydrocarbons Through Methane Derivatives; Hydrocarbon Chemistry 2nd Edition; 2003; John Wiley & Sons, Inc.; pp. 123, 149, and 153.

(Continued)

*Primary Examiner* — Tam M Nguyen
(74) *Attorney, Agent, or Firm* — Jack E. Ebel

(57) ABSTRACT

A process for converting gaseous alkanes to olefins, higher molecular weight hydrocarbons or mixtures thereof wherein a gaseous feed containing alkanes is thermally reacted with a dry bromine vapor to form alkyl bromides and hydrogen bromide. Poly-brominated alkanes present in the alkyl bromides are further reacted with methane over a suitable catalyst to form mono-brominated species. The mixture of alkyl bromides and hydrogen bromide is then reacted over a suitable catalyst at a temperature sufficient to form olefins, higher molecular weight hydrocarbons or mixtures thereof and hydrogen bromide. Various methods are disclosed to remove the hydrogen bromide from the higher molecular weight hydrocarbons, to generate bromine from the hydrogen bromide for use in the process, and to selectively form mono-brominated alkanes in the bromination step.

16 Claims, 22 Drawing Sheets

U.S. PATENT DOCUMENTS

| | | |
|---|---|---|
| 2,941,014 A | 6/1960 | Rothweiler et al. |
| 3,076,784 A | 2/1963 | Schulte-Huermann et al. |
| 3,172,915 A | 3/1965 | Borkowski et al. |
| 3,246,043 A | 4/1966 | Rosset et al. |
| 3,254,023 A | 5/1966 | Miale et al. |
| 3,273,964 A | 9/1966 | Rosset |
| 3,291,708 A | 12/1966 | Juda |
| 3,294,846 A | 12/1966 | Livak et al. |
| 3,310,380 A | 3/1967 | Lester |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Given et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |

| | | | | | |
|---|---|---|---|---|---|
| 4,634,800 A | 1/1987 | Withers, Jr. et al. | 5,026,934 A | 6/1991 | Bains et al. |
| 4,642,403 A | 2/1987 | Hyde et al. | 5,026,937 A | 6/1991 | Bricker |
| 4,642,404 A | 2/1987 | Shihabi | 5,026,944 A | 6/1991 | Allenger et al. |
| 4,652,688 A | 3/1987 | Brophy et al. | 5,034,566 A | 7/1991 | Ishino et al. |
| 4,654,449 A | 3/1987 | Chang et al. | 5,043,502 A | 8/1991 | Martindale et al. |
| 4,655,893 A | 4/1987 | Beale | 5,055,235 A | 10/1991 | Brackenridge et al. |
| 4,658,073 A | 4/1987 | Tabak | 5,055,625 A | 10/1991 | Neidiffer et al. |
| 4,658,077 A | 4/1987 | Kolts et al. | 5,055,633 A | 10/1991 | Volles |
| 4,665,259 A | 5/1987 | Brazdil et al. | 5,055,634 A | 10/1991 | Volles |
| 4,665,267 A | 5/1987 | Barri | 5,059,744 A | 10/1991 | Harandi et al. |
| 4,665,270 A | 5/1987 | Brophy et al. | 5,068,478 A | 11/1991 | Miller et al. |
| 4,675,410 A | 6/1987 | Feitler et al. | 5,071,449 A | 12/1991 | Sircar |
| 4,690,903 A | 9/1987 | Chen et al. | 5,071,815 A | 12/1991 | Wallace et al. |
| 4,695,663 A | 9/1987 | Hall et al. | 5,073,656 A | 12/1991 | Chafin et al. |
| 4,696,985 A | 9/1987 | Martin | 5,073,657 A | 12/1991 | Warren |
| 4,704,488 A | 11/1987 | Devries et al. | 5,082,473 A | 1/1992 | Keefer |
| 4,704,493 A | 11/1987 | Devires et al. | 5,082,816 A | 1/1992 | Teller et al. |
| 4,709,108 A | 11/1987 | Devries et al. | 5,085,674 A | 2/1992 | Leavitt |
| 4,720,600 A | 1/1988 | Beech, Jr. et al. | 5,087,779 A | 2/1992 | Nubel et al. |
| 4,720,602 A | 1/1988 | Chu | 5,087,786 A | 2/1992 | Nubel et al. |
| 4,724,275 A | 2/1988 | Hinnenkamp et al. | 5,087,787 A | 2/1992 | Kimble et al. |
| 4,735,747 A | 4/1988 | Ollivier et al. | 5,093,533 A | 3/1992 | Wilson |
| 4,737,594 A | 4/1988 | Olah | 5,093,542 A | 3/1992 | Gaffney |
| 4,748,013 A | 5/1988 | Saito et al. | 5,096,469 A | 3/1992 | Keefer |
| 4,762,596 A | 8/1988 | Huang et al. | 5,097,083 A | 3/1992 | Stauffer |
| 4,769,504 A | 9/1988 | Noceti et al. | 5,099,084 A | 3/1992 | Stauffer |
| 4,774,216 A | 9/1988 | Kolts et al. | 5,105,045 A | 4/1992 | Kimble et al. |
| 4,775,462 A | 10/1988 | Imai et al. | 5,105,046 A | 4/1992 | Washecheck |
| 4,777,321 A | 10/1988 | Harandi et al. | 5,107,032 A | 4/1992 | Erb et al. |
| 4,781,733 A | 11/1988 | Babcock et al. | 5,107,051 A | 4/1992 | Pannell |
| 4,783,566 A | 11/1988 | Kocal et al. | 5,107,061 A | 4/1992 | Ou et al. |
| 4,788,369 A | 11/1988 | Marsh et al. | 5,108,579 A | 4/1992 | Casci |
| 4,788,377 A | 11/1988 | Chang et al. | 5,118,899 A | 6/1992 | Kimble et al. |
| 4,792,642 A | 12/1988 | Rule et al. | 5,120,332 A | 6/1992 | Wells |
| 4,795,732 A | 1/1989 | Barri | 5,132,343 A | 7/1992 | Zwecker et al. |
| 4,795,737 A | 1/1989 | Rule et al. | 5,138,112 A | 8/1992 | Gosling et al. |
| 4,795,843 A | 1/1989 | Imai et al. | 5,139,991 A | 8/1992 | Taylor et al. |
| 4,795,848 A | 1/1989 | Teller et al. | 5,146,027 A | 9/1992 | Gaffney |
| 4,804,797 A | 2/1989 | Minet et al. | 5,157,189 A | 10/1992 | Karra |
| 4,804,800 A | 2/1989 | Bortinger et al. | 5,160,502 A | 11/1992 | Kimble et al. |
| 4,808,763 A | 2/1989 | Shum | 5,166,452 A | 11/1992 | Gradl et al. |
| 4,814,527 A | 3/1989 | Diesen | 5,175,382 A | 12/1992 | Hebgen et al. |
| 4,814,532 A | 3/1989 | Yoshida et al. | 5,178,748 A | 1/1993 | Casci et al. |
| 4,814,535 A | 3/1989 | Yurchak | 5,185,479 A | 2/1993 | Stauffer |
| 4,814,536 A | 3/1989 | Yurchak | 5,188,725 A | 2/1993 | Harandi |
| 4,849,562 A | 7/1989 | Buhs et al. | 5,191,142 A | 3/1993 | Marshall et al. |
| 4,849,573 A | 7/1989 | Kaefing | 5,194,244 A | 3/1993 | Brownscombe et al. |
| 4,851,602 A | 7/1989 | Harandi et al. | 5,202,506 A | 4/1993 | Kirchner et al. |
| 4,851,606 A | 7/1989 | Ragonese et al. | 5,202,511 A | 4/1993 | Salinas, III et al. |
| 4,886,925 A | 12/1989 | Harandi | 5,208,402 A | 5/1993 | Wilson |
| 4,886,932 A | 12/1989 | Leyshon | 5,210,357 A | 5/1993 | Kolts et al. |
| 4,891,463 A | 1/1990 | Chu | 5,215,648 A | 6/1993 | Zones et al. |
| 4,895,995 A | 1/1990 | James, Jr. et al. | 5,223,471 A | 6/1993 | Washecheck |
| 4,899,000 A | 2/1990 | Stauffer | 5,228,888 A | 7/1993 | Gmelin et al. |
| 4,899,001 A | 2/1990 | Kalnes et al. | 5,233,113 A | 8/1993 | Periana et al. |
| 4,899,002 A | 2/1990 | Harandi et al. | 5,237,115 A | 8/1993 | Makovec et al. |
| 4,902,842 A | 2/1990 | Kalnes et al. | 5,243,098 A | 9/1993 | Miller et al. |
| 4,925,995 A | 5/1990 | Robschlager | 5,243,114 A | 9/1993 | Johnson et al. |
| 4,929,781 A | 5/1990 | James, Jr. et al. | 5,245,109 A | 9/1993 | Kaminsky et al. |
| 4,939,310 A | 7/1990 | Wade | 5,254,772 A | 10/1993 | Dukat et al. |
| 4,939,311 A | 7/1990 | Washecheck et al. | 5,254,790 A | 10/1993 | Thomas et al. |
| 4,939,314 A | 7/1990 | Harandi et al. | 5,264,635 A | 11/1993 | Le et al. |
| 4,945,175 A | 7/1990 | Hobbs et al. | 5,268,518 A | 12/1993 | West et al. |
| 4,950,811 A | 8/1990 | Doussain et al. | 5,276,226 A | 1/1994 | Horvath et al. |
| 4,950,822 A | 8/1990 | Dileo et al. | 5,276,240 A | 1/1994 | Timmons et al. |
| 4,956,521 A | 9/1990 | Volles | 5,276,242 A | 1/1994 | Wu |
| 4,962,252 A | 10/1990 | Wade | 5,284,990 A | 2/1994 | Peterson et al. |
| 4,973,776 A | 11/1990 | Allenger et al. | 5,300,126 A | 4/1994 | Brown et al. |
| 4,973,786 A | 11/1990 | Karra | 5,306,855 A | 4/1994 | Periana et al. |
| 4,982,024 A | 1/1991 | Lin et al. | 5,316,995 A | 5/1994 | Kaminsky et al. |
| 4,982,041 A | 1/1991 | Campbell | 5,319,132 A | 6/1994 | Ozawa et al. |
| 4,988,660 A | 1/1991 | Campbell | 5,334,777 A | 8/1994 | Miller et al. |
| 4,990,696 A | 2/1991 | Stauffer | 5,345,021 A | 9/1994 | Casci et al. |
| 4,990,711 A | 2/1991 | Chen et al. | 5,354,916 A | 10/1994 | Horvath et al. |
| 5,001,293 A | 3/1991 | Nubel et al. | 5,354,931 A | 10/1994 | Jan et al. |
| 5,004,847 A | 4/1991 | Beaver et al. | 5,366,949 A | 11/1994 | Schubert |
| 5,013,424 A | 5/1991 | James, Jr. et al. | 5,371,313 A | 12/1994 | Ostrowicki |
| 5,013,793 A | 5/1991 | Wang et al. | 5,382,704 A | 1/1995 | Krespan et al. |
| 5,019,652 A | 5/1991 | Taylor et al. | 5,382,743 A | 1/1995 | Beech, Jr. et al. |

| | | | | | | |
|---|---|---|---|---|---|---|
| 5,382,744 A | 1/1995 | Abbott et al. | | 5,895,831 A | 4/1999 | Brasier et al. |
| 5,385,650 A | 1/1995 | Howarth et al. | | 5,898,086 A | 4/1999 | Harris |
| 5,385,718 A | 1/1995 | Casci et al. | | 5,905,169 A | 5/1999 | Jacobson |
| 5,395,981 A | 3/1995 | Marker | | 5,906,892 A | 5/1999 | Thompson et al. |
| 5,399,258 A | 3/1995 | Fletcher et al. | | 5,908,963 A | 6/1999 | Voss et al. |
| 5,401,890 A | 3/1995 | Parks | | 5,928,488 A | 7/1999 | Newman |
| 5,401,894 A | 3/1995 | Brasier et al. | | 5,952,538 A | 9/1999 | Vaughn et al. |
| 5,406,017 A | 4/1995 | Withers, Jr. | | 5,959,170 A | 9/1999 | Withers, Jr. et al. |
| 5,411,641 A | 5/1995 | Trainham, III et al. | | 5,968,236 A | 10/1999 | Bassine |
| 5,414,173 A | 5/1995 | Garces et al. | | 5,969,195 A | 10/1999 | Stabel et al. |
| 5,430,210 A | 7/1995 | Grasselli et al. | | 5,977,402 A | 11/1999 | Sekiguchi et al. |
| 5,430,214 A | 7/1995 | Smith et al. | | 5,983,476 A | 11/1999 | Eshelman et al. |
| 5,430,219 A | 7/1995 | Sanfilippo et al. | | 5,986,158 A | 11/1999 | Van Broekhoven et al. |
| 5,433,828 A | 7/1995 | van Velzen et al. | | 5,994,604 A | 11/1999 | Reagen et al. |
| 5,436,378 A | 7/1995 | Masini et al. | | 5,998,679 A | 12/1999 | Miller |
| 5,444,168 A | 8/1995 | Brown | | 5,998,686 A | 12/1999 | Clem et al. |
| 5,446,234 A | 8/1995 | Casci et al. | | 6,002,059 A | 12/1999 | Hellring et al. |
| 5,453,557 A | 9/1995 | Harley et al. | | 6,015,867 A | 1/2000 | Fushimi et al. |
| 5,456,822 A | 10/1995 | Marcilly et al. | | 6,018,088 A | 1/2000 | Olah |
| 5,457,255 A | 10/1995 | Kumata et al. | | 6,022,929 A | 2/2000 | Chen et al. |
| 5,464,799 A | 11/1995 | Casci et al. | | 6,034,288 A | 3/2000 | Scott et al. |
| 5,465,699 A | 11/1995 | Voigt | | 6,056,804 A | 5/2000 | Keefer et al. |
| 5,470,377 A | 11/1995 | Whitlock | | 6,068,679 A | 5/2000 | Zheng |
| 5,480,629 A | 1/1996 | Thompson et al. | | 6,072,091 A | 6/2000 | Cosyns et al. |
| 5,486,627 A | 1/1996 | Quarderer, Jr. et al. | | 6,087,294 A | 7/2000 | Klabunde et al. |
| 5,489,719 A | 2/1996 | Le et al. | | 6,090,312 A | 7/2000 | Ziaka et al. |
| 5,489,727 A | 2/1996 | Randolph et al. | | 6,093,306 A | 7/2000 | Hanrahan et al. |
| 5,500,297 A | 3/1996 | Thompson et al. | | 6,096,932 A | 8/2000 | Subramanian |
| 5,510,525 A | 4/1996 | Sen et al. | | 6,096,933 A | 8/2000 | Cheung et al. |
| 5,523,503 A | 6/1996 | Funk et al. | | 6,103,215 A | 8/2000 | Zones et al. |
| 5,525,230 A | 6/1996 | Wrigley et al. | | 6,107,561 A | 8/2000 | Thompson |
| 5,538,540 A | 7/1996 | Whitlock | | 6,117,371 A | 9/2000 | Mack |
| 5,563,313 A | 10/1996 | Chung et al. | | 6,124,514 A | 9/2000 | Emmrich et al. |
| 5,565,092 A | 10/1996 | Pannell et al. | | 6,127,588 A | 10/2000 | Kimble et al. |
| 5,565,616 A | 10/1996 | Li et al. | | 6,130,260 A | 10/2000 | Hall et al. |
| 5,571,762 A | 11/1996 | Clerici et al. | | 6,143,939 A | 11/2000 | Farcasiu et al. |
| 5,571,885 A | 11/1996 | Chung et al. | | 6,169,218 B1 | 1/2001 | Hearn et al. |
| 5,599,381 A | 2/1997 | Whitlock | | 6,180,841 B1 | 1/2001 | Fatutto et al. |
| 5,600,043 A | 2/1997 | Johnston et al. | | 6,187,871 B1 | 2/2001 | Thompson et al. |
| 5,600,045 A | 2/1997 | Van Der Aalst et al. | | 6,187,983 B1 | 2/2001 | Sun |
| 5,609,654 A | 3/1997 | Le et al. | | 6,203,712 B1 | 3/2001 | Bronner et al. |
| 5,633,419 A | 5/1997 | Spencer et al. | | 6,207,864 B1 | 3/2001 | Henningsen et al. |
| 5,639,930 A | 6/1997 | Penick | | 6,225,517 B1 | 5/2001 | Nascimento et al. |
| 5,653,956 A | 8/1997 | Zones | | 6,248,218 B1 | 6/2001 | Linkous et al. |
| 5,656,149 A | 8/1997 | Zones et al. | | 6,265,505 B1 | 7/2001 | McConville et al. |
| 5,661,097 A | 8/1997 | Spencer et al. | | 6,281,405 B1 | 8/2001 | Davis et al. |
| 5,663,465 A | 9/1997 | Clegg et al. | | 6,320,085 B1 | 11/2001 | Arvai et al. |
| 5,663,474 A | 9/1997 | Pham et al. | | 6,337,063 B1 | 1/2002 | Rouleau et al. |
| 5,675,046 A | 10/1997 | Ohno et al. | | 6,342,200 B1 | 1/2002 | Rouleau et al. |
| 5,675,052 A | 10/1997 | Menon et al. | | 6,368,490 B1 | 4/2002 | Gestermann |
| 5,679,134 A | 10/1997 | Brugerolle et al. | | 6,369,283 B1 | 4/2002 | Guram et al. |
| 5,679,879 A | 10/1997 | Mercier et al. | | 6,372,949 B1 | 4/2002 | Brown et al. |
| 5,684,213 A | 11/1997 | Nemphos et al. | | 6,376,731 B1 | 4/2002 | Evans et al. |
| 5,693,191 A | 12/1997 | Pividal et al. | | 6,380,328 B1 | 4/2002 | McConville et al. |
| 5,695,890 A | 12/1997 | Thompson et al. | | 6,380,423 B2 | 4/2002 | Banning et al. |
| 5,698,747 A | 12/1997 | Godwin et al. | | 6,380,444 B1 | 4/2002 | Bjerrum et al. |
| 5,705,712 A | 1/1998 | Frey et al. | | 6,395,945 B1 | 5/2002 | Randolph |
| 5,705,728 A | 1/1998 | Viswanathan et al. | | 6,403,840 B1 | 6/2002 | Zhou et al. |
| 5,705,729 A | 1/1998 | Huang | | 6,406,523 B1 | 6/2002 | Connor et al. |
| 5,708,246 A | 1/1998 | Camaioni et al. | | 6,423,211 B1 | 7/2002 | Randolph et al. |
| 5,720,858 A | 2/1998 | Noceti et al. | | 6,426,441 B1 | 7/2002 | Randolph et al. |
| 5,728,897 A | 3/1998 | Buysch et al. | | 6,426,442 B1 | 7/2002 | Ichikawa et al. |
| 5,728,905 A | 3/1998 | Clegg et al. | | 6,452,058 B1 | 9/2002 | Schweizer et al. |
| 5,734,073 A | 3/1998 | Chambers et al. | | 6,455,650 B1 | 9/2002 | Lipian et al. |
| 5,741,949 A | 4/1998 | Mack | | 6,462,243 B1 | 10/2002 | Zhou et al. |
| 5,744,669 A | 4/1998 | Kalnes et al. | | 6,465,696 B1 | 10/2002 | Zhou et al. |
| 5,750,801 A | 5/1998 | Buysch et al. | | 6,465,699 B1 | 10/2002 | Grosso |
| 5,770,175 A | 6/1998 | Zones | | 6,472,345 B2 | 10/2002 | Hintermann et al. |
| 5,776,871 A | 7/1998 | Cothran et al. | | 6,472,572 B1 | 10/2002 | Zhou et al. |
| 5,780,703 A | 7/1998 | Chang et al. | | 6,475,463 B1 | 11/2002 | Elomari et al. |
| 5,782,936 A | 7/1998 | Riley | | 6,475,464 B1 | 11/2002 | Rouleau et al. |
| 5,798,314 A | 8/1998 | Spencer et al. | | 6,479,705 B2 | 11/2002 | Murata et al. |
| 5,814,715 A | 9/1998 | Chen et al. | | 6,482,997 B2 | 11/2002 | Petit-Clair et al. |
| 5,817,904 A | 10/1998 | Vic et al. | | 6,486,368 B1 | 11/2002 | Zhou et al. |
| 5,821,394 A | 10/1998 | Schoebrechts et al. | | 6,491,809 B1 | 12/2002 | Briot et al. |
| 5,847,224 A | 12/1998 | Koga et al. | | 6,495,484 B1 | 12/2002 | Holtcamp |
| 5,849,978 A | 12/1998 | Benazzi et al. | | 6,509,485 B2 | 1/2003 | Mul et al. |
| 5,866,735 A | 2/1999 | Cheung et al. | | 6,511,526 B2 | 1/2003 | Jagger et al. |
| 5,882,614 A | 3/1999 | Taylor, Jr. et al. | | 6,514,319 B2 | 2/2003 | Keefer et al. |

| | | |
|---|---|---|
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,365,102 B1 | 4/2008 | Weissman |
| 7,390,395 B2 | 6/2008 | Elomari |
| 7,560,607 B2 | 7/2009 | Waycuilis |
| 7,674,941 B2 | 3/2010 | Waycuilis et al. |
| 7,713,510 B2 | 5/2010 | Harrod et al. |
| 7,880,041 B2 | 2/2011 | Waycuilis |
| 8,008,535 B2 | 8/2011 | Waycuilis |
| 2002/0102672 A1 | 8/2002 | Mizrahi |
| 2002/0193649 A1 | 12/2002 | O'Rear et al. |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188271 A1 | 9/2004 | Ramachandraiah et al. |
| 2004/0188324 A1 | 9/2004 | Elomari |
| 2004/0220433 A1 | 11/2004 | Van Der Heide |

| Publication No. | Date | Name | | Country | Number | Date |
|---|---|---|---|---|---|---|
| 2005/0027084 A1 | 2/2005 | Clarke | | EP | 1186591 A2 | 3/2002 |
| 2005/0038310 A1 | 2/2005 | Lorkovic et al. | | EP | 1253126 A1 | 10/2002 |
| 2005/0042159 A1 | 2/2005 | Elomari | | EP | 1312411 A2 | 5/2003 |
| 2005/0047927 A1 | 3/2005 | Lee et al. | | EP | 1235769 B1 | 5/2004 |
| 2005/0148805 A1 | 7/2005 | Jones | | EP | 1440939 A1 | 7/2004 |
| 2005/0171393 A1 | 8/2005 | Lorkovic | | EP | 1235772 B1 | 1/2005 |
| 2005/0192468 A1 | 9/2005 | Sherman et al. | | EP | 1661620 A1 | 5/2006 |
| 2005/0215837 A1 | 9/2005 | Hoffpauir | | EP | 1760057 A1 | 3/2007 |
| 2005/0234276 A1 | 10/2005 | Waycuilis | | EP | 1689728 B1 | 4/2007 |
| 2005/0234277 A1 | 10/2005 | Waycuilis | | EP | 1808227 A1 | 7/2007 |
| 2005/0245771 A1 | 11/2005 | Fong et al. | | EP | 1837320 A1 | 9/2007 |
| 2005/0245772 A1 | 11/2005 | Fong | | GB | 5125 | 0/1912 |
| 2005/0245777 A1 | 11/2005 | Fong | | GB | 156122 | 3/1922 |
| 2005/0267224 A1 | 12/2005 | Herling | | GB | 294100 | 6/1929 |
| 2006/0025617 A1 | 2/2006 | Begley | | GB | 363009 | 12/1931 |
| 2006/0100469 A1 | 5/2006 | Waycuilis | | GB | 402928 | 12/1933 |
| 2006/0135823 A1 | 6/2006 | Jun | | GB | 474922 A | 11/1937 |
| 2006/0138025 A1 | 6/2006 | Zones | | GB | 536491 | 5/1941 |
| 2006/0138026 A1 | 6/2006 | Chen | | GB | 553950 | 6/1943 |
| 2006/0149116 A1 | 7/2006 | Slaugh | | GB | 586483 | 3/1947 |
| 2006/0229228 A1 | 10/2006 | Komon et al. | | GB | 775590 | 5/1957 |
| 2006/0229475 A1 | 10/2006 | Weiss et al. | | GB | 793214 | 4/1958 |
| 2006/0270863 A1 | 11/2006 | Reiling | | GB | 796048 | 6/1958 |
| 2006/0288690 A1 | 12/2006 | Elomari | | GB | 796085 | 6/1958 |
| 2007/0004955 A1 | 1/2007 | Kay | | GB | 883256 | 11/1961 |
| 2007/0078285 A1 | 4/2007 | Dagle | | GB | 883256 A | 11/1961 |
| 2007/0100189 A1 | 5/2007 | Stauffer | | GB | 930341 A | 7/1963 |
| 2007/0129584 A1 | 6/2007 | Basset | | GB | 950975 | 3/1964 |
| 2007/0142680 A1 | 6/2007 | Ayoub | | GB | 950976 | 3/1964 |
| 2007/0148067 A1 | 6/2007 | Zones | | GB | 991303 | 5/1965 |
| 2007/0148086 A1 | 6/2007 | Zones | | GB | 995960 | 6/1965 |
| 2007/0149778 A1 | 6/2007 | Zones | | GB | 1015033 | 12/1965 |
| 2007/0149789 A1 | 6/2007 | Zones | | GB | 1104294 | 2/1968 |
| 2007/0149819 A1 | 6/2007 | Zones | | GB | 1133752 | 11/1968 |
| 2007/0149824 A1 | 6/2007 | Zones | | GB | 1172002 | 11/1969 |
| 2007/0149837 A1 | 6/2007 | Zones | | GB | 1212240 | 11/1970 |
| 2007/0197801 A1 | 8/2007 | Bolk | | GB | 1233299 | 5/1971 |
| 2007/0197847 A1 | 8/2007 | Liu | | GB | 1253618 | 11/1971 |
| 2007/0213545 A1 | 9/2007 | Bolk | | GB | 1263806 A | 2/1972 |
| 2007/0238905 A1 | 10/2007 | Arredondo | | GB | 1446803 | 8/1976 |
| 2007/0238909 A1* | 10/2007 | Gadewar et al. ................ 585/16 | | GB | 1542112 | 3/1979 |
| 2007/0276168 A1 | 11/2007 | Garel | | GB | 2095243 A | 9/1982 |
| 2007/0284284 A1 | 12/2007 | Zones | | GB | 2095245 A | 9/1982 |
| 2008/0022717 A1 | 1/2008 | Yoshida et al. | | GB | 2095249 A | 9/1982 |
| 2008/0152555 A1 | 6/2008 | Wang et al. | | GB | 2116546 A | 9/1982 |
| 2008/0171898 A1 | 7/2008 | Waycuilis | | GB | 2120249 A | 11/1983 |
| 2008/0183022 A1 | 7/2008 | Waycuilis | | GB | 2185754 A | 7/1987 |
| 2008/0188697 A1 | 8/2008 | Lorkovic | | GB | 2191214 A | 12/1987 |
| 2008/0200740 A1 | 8/2008 | Waycuilis | | SU | 694483 A1 | 10/1979 |
| 2008/0275284 A1 | 11/2008 | Waycuilis | | WO | 83/00859 | 3/1983 |
| 2009/0005620 A1 | 1/2009 | Waycuilis et al. | | WO | 85/04863 | 11/1985 |
| 2009/0163749 A1 | 6/2009 | Li et al. | | WO | 85/04867 | 11/1985 |
| 2009/0308759 A1 | 12/2009 | Waycuilis | | WO | 90/08120 | 7/1990 |
| 2009/0312586 A1 | 12/2009 | Waycuilis et al. | | WO | 90/08752 | 8/1990 |
| 2009/0326292 A1 | 12/2009 | Waycuilis | | WO | 91/18856 | 12/1991 |
| 2010/0087686 A1 | 4/2010 | Fong et al. | | WO | 92/03401 | 3/1992 |
| 2010/0096588 A1 | 4/2010 | Gadewar et al. | | WO | 92/12946 | 8/1992 |
| 2010/0234637 A1 | 9/2010 | Fong et al. | | WO | 93/16798 | 9/1993 |
| 2011/0015458 A1 | 1/2011 | Waycuilis et al. | | WO | 96/22263 | 7/1996 |
| 2011/0071326 A1 | 3/2011 | Waycuilis | | WO | 97/44302 | 11/1997 |
| 2011/0218372 A1 | 9/2011 | Waycuilis et al. | | WO | 98/12165 | 3/1998 |
| 2011/0218374 A1 | 9/2011 | Waycuilis | | WO | 99/07443 | 2/1999 |
| | | | | WO | 00/07718 A1 | 2/2000 |
| FOREIGN PATENT DOCUMENTS | | | | WO | 00/09261 A1 | 2/2000 |
| CA | 1101441 | 5/1981 | | WO | 01/14300 A1 | 3/2001 |
| CA | 1202610 | 4/1986 | | WO | 01/38275 A1 | 5/2001 |
| CA | 2542857 | 5/2005 | | WO | 01/44149 A1 | 6/2001 |
| CA | 2236126 | 8/2006 | | WO | 02/094749 A1 | 11/2002 |
| CA | 2203115 | 9/2006 | | WO | 02/094750 A1 | 11/2002 |
| CA | 2510093 | 12/2006 | | WO | 02/094751 A2 | 11/2002 |
| EP | 0164798 A1 | 12/1985 | | WO | 02/094752 A1 | 11/2002 |
| EP | 0418971 A1 | 3/1991 | | WO | 03/000635 A1 | 1/2003 |
| EP | 0418974 A1 | 3/1991 | | WO | 03/002251 A2 | 1/2003 |
| EP | 0418975 A1 | 3/1991 | | WO | 03/018524 A1 | 3/2003 |
| EP | 0510238 A1 | 10/1992 | | WO | 03/020676 A1 | 3/2003 |
| EP | 0526908 A2 | 2/1993 | | WO | 03/022827 A1 | 3/2003 |
| EP | 0346612 B1 | 8/1993 | | WO | 03/043575 A2 | 5/2003 |
| EP | 0560546 A1 | 9/1993 | | WO | 03/051813 A1 | 6/2003 |
| EP | 0976705 A1 | 7/1998 | | WO | 03/062143 A1 | 7/2003 |

| | | |
|---|---|---|
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006-067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/076942 A1 | 7/2006 |
| WO | 2006/083427 A2 | 8/2006 |
| WO | 2006-100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A1 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |
| WO | 2008/157047 A1 | 12/2008 |
| WO | 2009/152403 A1 | 12/2009 |
| WO | 2009/152405 A1 | 12/2009 |
| WO | 2009/152408 A1 | 12/2009 |
| WO | 2010/009376 A1 | 1/2010 |
| WO | 2011/008573 A1 | 1/2011 |
| WO | 2011/109244 A2 | 9/2011 |
| WO | 2011/159490 A1 | 12/2011 |

OTHER PUBLICATIONS

Rakoff et al.; Quimica Organica Fundamental; The Macmillan Company; 1966; pp. 58-63 and 76-77.
U.S. Office Action from U.S. Appl. No. 12/112,926 dated Jan. 16, 2009.
U.S. Office Action from U.S. Appl. No. 12/112,926 dated Sep. 14, 2009.
U.S. Office Action from U.S. Appl. No. 12/112,926 dated Jan. 7, 2010.
Liu et al.; "Higher Hydrocarbons from Methane Condensation Mediated by HBr"; Journal of Molecular Catalysis A: Chemical 273; Elsevier B.V. 2007; pp. 14-20.
U.S. Office Action from U.S. Appl. No. 11/778,479 dated Feb. 22, 2010.
U.S. Office Action from U.S. Appl. No. 12/123,924 dated Mar. 19, 2010.
U.S. Appl. No. 60/487,364, filed Jul. 15, 2003, Lorkovic et al.
U.S. Appl. No. 60/559,844, filed Apr. 6, 2004, Sherman et al.
Abstract of EP0021497 (A1), Synthesis of polyoxyalkylene glycol monoalkyl ethers, Publication date: Jan. 7, 1981, Inventor: Gibson, esp@cenet database—worldwide.
U.S. Office Action from U.S. Appl. No. 10/365,346 dated Jun. 12, 2006.
U.S. Office Action from U.S. Appl. No. 10/893,418 dated Jun. 14, 2007.
U.S. Office Action from U.S. Appl. No. 10/893,418 dated Jan. 2, 2008.
U.S. Office Action from U.S. Appl. No. 11/091,130 dated Oct. 3, 2007.
Benizri et al., Study of the Liquid-Vapor Equilibrium in the Bromine-Hydrobromic Acid-Water System, Hydrogen Energy Vector, 1980, pp. 101-116.
Bradshaw et al., Production of Hydrobromic Acid from Bromine and Methane for Hydrogen Production, Proceedings of the 2001 DOE Hydrogen Program Review, NREL/CP-570-30535, 2001.
Motupally et al., Recycling Chlorine from Hydrogen Chloride, The Electrochemical Society Interface, Fall 2008, pp. 32-36.
Wauters et al., Electrolytic Membrane Recovery of Bromine from Waste Hydrogen Bromide Streams, AIChE Journal, Oct. 1998, vol. 44, No. 10, pp. 2144-2148.
Kirk-Othmer Encyclopedia of Chemical Technology, 4th Edition, vol. 1, A Wiley-Interscience Publication, John Wiley & Sons, 1991, pp. 946-997.
Adachi et al., Synthesis of Sialyl Lewis X Ganglioside Analogs Containing a Variable Length Spacer Between the Sugar and Lipophilic Moieties, J. Carbohydrate Chemistry, vol. 17, No. 4-5, 1998, pp. 595-607; XP009081720.
Bakker et al., An Exploratory Study of the Addition Reactions of Ethyleneglycol, 2-Chloroethanol and 1,3-Dichloro-2-Propanol to 1-Dodecene, J. Am. Oil Chem. Soc., vol. 44, No. 9, 1967, pp. 517-521; XP009081570.
Bouzide et al., Highly Selective Silver (I) Oxide Mediated Monoprotection of Symmetrical Diols, Tetrahedron Letters, Elsevier, vol. 38, No. 34, 1997, pp. 5945-5948; XP004094157.
Gibson et al., Phase-Transfer Synthesis of Monoalkyl Ethers of Oligoethylene Glycols, J. Org. Chem., vol. 45, No. 6, 1980, pp. 1095-1098; XP002427776.
Loiseau et al., Multigram Synthesis of Well-Defined Extended Bifunctional Polyethylene Glycol (PEG) Chains, J. Org. Chem., vol. 69, No. 3, 2004, pp. 639-647; XP002345040.
Mihai et al., Application of Bronsted-Type LFER in the Study of the Phospholipase C Mechanism, J. Am. Chem. Soc., vol. 125, No. 11, 2003, pp. 3236-3242; XP002427777.
Nishikawa et al., Ultrasonic Relaxations in Aqueous Solutions of Alcohols and the Balance between Hydrophobicity and Hydrophilicity of the Solutes, J. Phys. Chem., vol. 97, No. 14, 1993, pp. 3539-3544; XP002427775.
Prelog et al., Chirale 2,2'-Polyoxaalkano-9,9'-Spirobifluorene, Helvetica Chimica ACTA, vol. 62, No. 7, 1979, pp. 2285-2302; XP002030901.

Shimizu et al., Gas-Phase Electrolysis of Hydrobromic Acid Using PTFE-Bonded Carbon Electrode, Int. J. Hydrogen Energy, vol. 13, No. 6, pp. 345-349, 1988.
Velzen et al., HBr Electrolysis in the Ispra Mark 13A Flue Gas Desulphurization Process: Electrolysis in a DEM Cell, J. of Applied Electrochemistry, vol. 20, pp. 60-68, 1990.
Whitesides et al., Nuclear Magnetic Resonance Spectroscopy. The Effect of Structure on Magnetic Nonequivalence Due to Molecular Asymmetry, J. Am. Chem. Soc., vol. 86, No. 13, 1964, pp. 2628-2634; XP002427774.
Combined International Search Report and Written Opinion Dated Apr. 17, 2007 for PCT/US2006/13394, in the name of GRT, Inc.
U.S. Office Action from U.S. Appl. No. 10/826,885 dated Oct. 31, 2005.
U.S. Office Action from U.S. Appl. No. 10/826,885 dated Apr. 19, 2006.
U.S. Office Action from U.S. Appl. No. 10/826,885 dated Jul. 27, 2006.
U.S. Office Action from U.S. Appl. No. 10/826,885 dated Nov. 2, 2006.
U.S. Office Action from U.S. Appl. No. 10/826,885 dated Jan. 24, 2007.
U.S. Office Action from U.S. Appl. No. 11/101,886 dated Jan. 24, 2007.
U.S. Office Action from U.S. Appl. No. 11/254,438 dated Jan. 24, 2007.
U.S. Office Action from U.S. Appl. No. 11/254,438 dated Nov. 1, 2007.
JLM Technology Ltd.; "The Miller GLS Technology for Conversion of Light Hydrocarbons to Alcohols"; New Science for the Benefit of Humanity; May 31, 2000, pp. 1-10.
Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.
Taylor, Charles E.; "Conversion of Substituted Methanes Over ZSM-Catalysts"; 2000; pp. 3633-3638; Studies in Surface Science and Catalysis 130; Elsevier Science B.V.
ZSM-5 Catalyst; http://chemelab.ucsd.edu/methanol/memos/ZSM-5.html; Nov. 6, 2003; p. 1.
Final Report; "Abstract"; http://chemelab.ucsd.edu/methanol/memos/final.html; May 9, 2004; pp. 1-7.
Driscoll, Daniel J.; "Direct Methane Conversion"; Federal Energy Technology Center, U.S. Department of Energy; M970779; pp. 1-10.
Olah et al.; "Selective Monohalogenation of Methane over Supported Acid or Platinum Metal Catalysts and Hydrolysis of Methyl Halides . . . "; J. American Chemical Society 1985, vol. 107; 0002-7863/85/1507-7097$01.50/0; pp. 7097-7105.
Murray et al.; "Conversion of Methyl Halides to Hydrocarbons on Basic Zeolites: A Discovery by in Situ NMR"; J. American Chemical Society 1993, vol. 115; pp. 4732-4741.
Lorkovic et al.; "A Novel Integrated Process for the Functionalization of Methane and Ethane: Bromine as Mediator", Catalysis Today 98; 2004; pp. 317-322.
Lorkovic et al.; "C1 Oxidative Coupling via Bromine Activation and Tandem Catalytic Condensation over CaO/Zeolite Composites II . . . "; Catalysis Today 98; 2004; pp. 589-594.
Abstract of 8E812868, Aromatic hydrocarbons prodn. from chlorinated hydrocarbons, Publication date: Sep. 27, 1974, esp@cenet database—worldwide.
Abstract of BE814900, Volatile aramatic cpds. prodn., Publication date: Sep. 2, 1974, esp@cenet database—worldwide.
Abstract of CN1199039, Pentanol and its production process, Publication date: Nov. 18, 1998, Inventor: Kailun, esp@cenet database—worldwide.
Abstract of CN1210847, Process for producing low carbon alcohol by directly hydrating low carbon olefines, Publication date: Mar. 17, 1999, Inventor: Zhenguo et al., esp@cenet database—worldwide.
Abstract of CN1321728, Method for preparing aromatic hydrocarbon and hydrogen gas by using low-pressure gas, Publication date: Nov. 14, 2001, Inventor: Jie et al., esp@cenet database—worldwide.
Abstract of CN1451721, Process for non-catalytic combustion deoxidizing coal mine gas for producing methanol, Publication date: Oct. 29, 2003, Inventor: Pengwan et al., esp@cenet database—worldwide.
Abstract of CN1623969, Method for preparing 1, 4-benzene dimethanol, Publication date: Jun. 8, 2005, Inventor: Jiarong et al., esp@cenet database—worldwide.
Abstract of CN1657592, Method for converting oil to multiple energy fuel product, Publication date: Aug. 24, 2005, Inventor: Li, esp@cenet database—worldwide.
Abstract of CN1687316, Method for producing biologic diesel oil from rosin, Publication date: Oct. 26, 2005, Inventor: Jianchun et al, esp@cenet database—worldwide.
Abstract of CN1696248, Method for synthesizing biologic diesel oil based on ion liquid, Publication date: Nov. 16, 2005, Inventor: Sun, esp@cenet database—worldwide.
Abstract of CN1699516, Process for preparing bio-diesel-oil by using microalgae fat, Publication date: Nov. 23, 2005, Inventor: Miao, esp@cenet database—worldwide.
Abstract of CN1704392, Process for producing alkylbenzene, Publication date: Dec. 7, 2005, Inventor: Gao, esp@cenet database—worldwide.
Abstract of CN1724612, Biological diesel oil catalyst and method of synthesizing biological diesel oil using sai catalyst, Publication date: Jan. 25, 2006, Inventor: Gu, esp@cenet database—worldwide.
Abstract of CN1986737, Process of producing biodiesel oil with catering waste oil, Publication date: Jun. 27, 2007, Inventor: Chen, esp@cenet database—worldwide.
Abstract of CN100999680, Esterification reaction tech. Of preparing biodiesel by waste oil, Publication date: Jul. 18, 2007, Inventor: Weiming, esp@cenet database—worldwide.
Abstract of CN101016229, Refining method for bromomeoamyl alcohol, Publication date: Aug. 15, 2007, Inventor: Tian, esp@cenet database—worldwide.
Abstract of DE3209964, Process for the preparation of chlorinated hydrocarbons, Publication date: Nov. 11, 1982, Inventor: Pyke et al., esp@cenet database—worldwide.
Abstract of DE3210196, Process for the preparation of a monochlorinated olefin, Publication date: Jan. 5, 1983, Inventor: Pyke et al., esp@cenet database—worldwide.
Abstract of DE3226028, Process for the preparation of monochlorinated olefin, Publication date: Feb. 3, 1983, Inventor: Pyke et al., esp@cenet database—worldwide.
Abstract of DE3334225, Process for the preparation of 1, 2-dichloroethane, Publication date: Apr. 4, 1985, Inventor: Hebgen et al., esp@cenet database—worldwide.
Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE4434823, Continuous prodn. of hydroxy-benzyl alkyl ether, Publication date: Apr. 4, 1996, Inventor: Stein et al., esp@cenet database—worldwide.
Abstract of FR2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2-dichloroethane from reactor, Publication date: Oct. 6, 2006, Inventor: Balthasart et al., esp@cenet database—worldwide.

Abstract of IT1255246, Process for the preparation of dinitrodiphenylmethanes, Publication date: Oct. 20, 1995, Applicant: Enichem Spa et al., esp@cenet database—worldwide.

Abstract of IT1255358, Process for the synthesis of 1, 4-butanediol, Publication date: Oct. 31, 1995, Inventor: Marco, esp@cenet database—worldwide.

Abstract of JP2142740, Production of fluoroalcohol, Publication date: May 31, 1990, Inventor: Tsutomu et al., esp@cenet database—worldwide.

Abstract of JP2144150, Chemical process and catalyst used therefore, Publication date: Jun. 1, 1990, Inventor: Deidamusu et al., esp@cenet database—worldwide.

Abstract of JP4305542, Production of halogenated hydrocarbon compounds, Publication date: Oct. 28, 1992, Inventor: Shinsuke et al., esp@cenet database—worldwide.

Abstract of JP6172225, Method for fluorinating halogenated hydrocarbon, Publication date: Jun. 21, 1994, Inventor: Takashi et al., esp@cenet database—worldwide.

Abstract of JP6206834, Production of tetrachloroethanes, Publication date: Jul. 26, 1994, Inventor: Toshiro et al., esp@cenet database—worldwide.

Abstract of JP8266888, Method for decomposing aromatic halogen compound, Publication date: Oct. 15, 1996, Inventor: Yuuji et al., esp@cenet database—worldwide.

Abstract of JP2001031605, Production of 3-hydroxy-1-cycloalkene, Publication date: Feb. 6, 2001, Inventor: Hideo et al, esp@cenet database—worldwide.

Abstract of JP2004075683, Method for producing optically active halogenohydroxypropyl compound and glycidyl compound, Publication date: Mar. 11, 2004, Inventor: Keisuke et al., esp@cenet database—worldwide.

Abstract of JP2004189655, Method for fluorinating with microwave, Publication date: Jul. 8, 2004, Inventor: Masaharu et al., esp@cenet database—worldwide.

Abstract of JP2005075798, Method for Producing adamantyl ester compound, Publication date: Mar. 24, 2005, Inventor: Norihiro et al., esp@cenet database—worldwide..

Abstract of JP2005082563, Method for producing 1, 3-adamantanediol, Publication date: Mar. 31, 2005, Inventor: Norihiro et al., esp@cenet database—worldwide.

Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.

Abstract of JP2005254092, Method of manufacturing alkynes, Publication date: Sep. 22, 2005, Inventor: Shirakawa Eiji, esp@cenet database—worldwide.

Abstract of JP2006151892, Preparation method of alcohol derivative, Publication date: Jun. 15, 2006, Inventor: Baba Akio et al., esp@cenet database—worldwide.

Abstract of JP2006152263, Organic-inorganic hybrid-type mesoporous material, method for producing the same, and solid catalyst, Publication date: Jun. 15, 2006, Inventor: Junko et al., esp@cenet database—worldwide.

Abstract of JP2006193473, Aryl polyadamantane derivative having carboxy or acid anhydride group and method for producing the same, Publication date: Jul. 27, 2006, Inventor: Yasuto et al., esp@cenet database—worldwide.

Abstract of JP2006231318, Phosphorus containing macromolecule immobilizing palladium catalyst and method for using the same, Publication date: Sep. 7, 2006, Inventor: Osamu et al., esp@cenet database—worldwide.

Abstract of JP2006263567, Optical resolution method of optical isomer and optical resolution device, Publication date: Oct. 5, 2006, Inventor: Yoshikazu et al., esp@cenet database—worldwide.

Abstract of JP2006265157, Method for catalytically activating silicated nucleating agent using phosphazene base, Publication date: Oct. 5, 2006, Inventor: Yoshinori et al., esp@cenet database—worldwide.

Abstract of JP2006306758, Method for producing biaryl compound, Publication date: Nov. 9, 2006, Inventor: Yuji et al., esp@cenet database—worldwide.

Abstract of JP2007001942, Production method of para-xylene, Publication date: Jan. 11, 2007, Inventor: Kazuyoshi, esp@cenet database—worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.

Abstract of JP2007061594, Method for decomposing organohalogen compound and mobile decomposition system, Publication date: Mar. 15, 2007, Inventor: Koichi et al., esp@cenet database—worldwide.

Abstract of JP2007099729, Method for producing alpha-methylstyrene or cumene, Publication date: Apr. 19, 2007, Inventor: Toshio, esp@cenet database—worldwide.

Abstract of RO119778, Process for preparing perchloroethylene, Publication date: Mar. 30, 2005, Inventor: Horia et al., esp@cenet database—worldwide.

Abstract of WO0105737, Method for preparing a carboxylic acid, Publication date: Jan. 25, 2001, Inventor: Pascal et al., esp@cenet database—worldwide.

Abstract of WO0105738, Method for preparing a carboxylic acid, Publication date: Jan. 25, 2001, Inventor: Pascal et al., esp@cenet database—worldwide.

Abstract of WO2004092099, Method for producing cyclic enols, Publication date: Oct. 28, 2004, Inventor: Marko et al., esp@cenet database—worldwide.

Abstract of WO2006063852, Electroluminescent polymers and use thereof, Publication date: Jun. 22, 2006, Inventor: Arne et al., esp@cenet database—worldwide.

Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.

Abstract of WO2007028761, Method for chlorinating alcohols, Publication date: Mar. 15, 2007, Inventor: Rohde et al., esp@cenet database—worldwide.

Abstract of WO2007128842, Catalytic transalkylation of dialkyl benzenes, Publication date: Nov. 15, 2007, Inventor: Goncalvesalmeida et al., esp@cenet database—worldwide.

Abstract of WO2007137566, Method for catalytic conversion of organic oxygenated compounds from biomaterials, Publication date: Dec. 6, 2007, Inventor: Reschetilowski, esp@cenet database—worldwide.

Abstract of WO9721656, Method for making fluoroalkanols, Publication date: Jun. 19, 1997, Inventor: Gillet, esp@cenet database—worldwide.

Abstract of WO9950213, Method for producing dialkyl ethers, Publication date: Oct. 7, 1999, Inventor: Falkowski Juergen et al., esp@cenet database—worldwide.

Abstract of WO2006076942, Method for the production of synthetic fuels from oxygenates, Publication date: Jul. 27, 2006, Inventor: Rothaemel et al., esp@cenet database—worldwide.

Abstract of EP0039471, Process for the preparation of 2-chloro-1,1,1,2,3,3,3-heptafluoropropane, Publication date: Nov. 11, 1981, Inventor: Von Halasz, esp@cenet database—worldwide.

Abstract of EP0101337, Process for the production of methylene chloride, Publication date: Feb. 22, 1984, Inventor: Olah et al., esp@cenet database—worldwide.

Abstract of EP0407989, Method for the production of 1,1,1-trifluoro-2,2-dichloroethane by photochlorination, Publication date: Jan. 16, 1991, Inventor: Cremer et al., esp@cenet database—worldwide.

Abstract of EP0442258, Process for the preparation of a polyunsaturated olefin, Publication date: Aug. 21, 1991, Inventor: Gaudin et al., esp@cenet database—worldwide.

Abstract of EP0465294, Process for the preparation of unsaturated bromides, Publication date: Jan. 8, 1992, Inventor: Decaudin et al., esp@cenet database—worldwide.

Abstract of EP0549387, Synthesis of n-perfluorooctylbromide, Publication date: Jun. 30, 1993, Inventor: Drivon et al., esp@cenet database—worldwide.

Abstract of EP0850906, Process and apparatus for the etherification of olefinic hydrocarbon feedstocks, Publication date: Jul. 1, 1998, Inventor: Masson, esp@cenet database—worldwide.

Abstract of EP0858987, Process for the conversion of lighter alkanes to higher hydrocarbons, Publication date: Aug. 19, 1998, Inventor: Amariglio et al., esp@cenet database—worldwide.

Abstract of EP1404636, Integrated process for synthesizing alcohols and ethers from alkanes, Publication date: Apr. 7, 2004, Inventor: Zhou et al., esp@cenet database—worldwide.

Abstract of EP0235110, Process for the stabilization of silicalite catalysts, Publication date: Sep. 2, 1987, Inventor: Debras et al., esp@cenet database—worldwide.

U.S. Office Action from U.S. Appl. No. 12/112,926 dated Jul. 22, 2010.

U.S. Office Action from U.S. Appl. No. 12/123,924 dated Aug. 30, 2010.

U.S. Office Action from U.S. Appl. No. 12/502,024 dated Oct. 26, 2010.

U.S. Office Action from U.S. Appl. No. 12/139,135 dated Nov. 24, 2010.

Chretien; "Process for the Adjustment of the Hhv in the LNG Plants"; 23rd World Gas Conference; Amsterdam 2006; Jun. 5-9, 2006; pp. 1-14.

U.S. Office Communication from U.S. Appl. No. 12/139,135 dated Oct. 14, 2011.

U.S. Office Communication from U.S. Appl. No. 12/477,307 dated Oct. 7, 2011.

U.S. Office Communication from U.S. Appl. No. 12/502,024 dated Sep. 16, 2011.

Yang et al.; "Maximising the Value of Surplus Ethane and Cost-Effective Design to Handle Rich LNG"; publ. date Jun. 1, 2007; pp. 1-13.

U.S. Appl. No. 60/765,115, filed Feb. 3, 2006, Gadewar et al.

Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.

Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.

Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.

Zhou, Xiao-Ping et al.; "An Integrated Process for Partial Oxidation of Alkanes"; Chem. Commun. 2003; The Royal Society of Chemistry 2003; pp. 2294-2295.

Sun, Shouli et al.; "A General Integrated Process for Synthesizing Olefin Oxides"; Chem. Commun. 2004; The Royal Society of Chemistry 2004; pp. 2100-2101.

Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.

Yilmaz, Aysen et al.; "Bromine Mediated Partial Oxidation of Ethane over Nanostructured Zirconia Supported Metal Oxide/Bromide"; Microporous and Mesoporous Materials, 79; 2005; pp. 205-214.

Taylor, Charles E.; "PETC's On-Site Natural Gas Conversion Efforts"; Preprints of the Fuel Division, 208th National Meeting of the American Chemical Society, 39 (4); 1994; pp. 1228-1232.

Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.

Olah, George A. et al.; "Hydrocarbons Through Methane Derivatives"; Hydrocarbon Chemistry; 1995; pp. 89-90; John Wiley & Sons, Inc.

Akhrem, Irena S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.

Smirnov, Vladimir V. et al.; "Selective Bromination of Alkanes and Arylalkanes with CBr4"; Mendeleev Commun. 2000; pp. 175-176.

Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.

Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.

Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.

Mochida, Isao et al.; "The Catalytic Dehydrohalogenation of Haloethanes on Solid Acids and Bases"; Bulletin of the Chemical Society of Japan, vol. 44; 1971; pp. 3305-3310.

Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.

Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.

Mishakov, Ilya V. et al.; "Nanocrystalline MgO as a Dehydrohalogenation Catalyst"; Journal of Catalysis 206; 2002; pp. 40-48; Elsevier Science, USA.

Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.

Fenelonov, Vladimir B. et al.; "Changes in Texture and Catalytic Activity of Nanocrystalline MgO during its Transformation to MgCl2 in the Reaction with 1-Chlorobutane"; J. Phys. Chem. B 2001, 105; pp. 3937-3941; 2001 American Chemical Society.

http://webbook.nist.gov/; "Welcome to the NIST Chemistry WebBook"; 2005; U.S. Secretary of Commerce on Behalf of the United States of America.

Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.

Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.

Thomas, John Meurig et al.; "Catalytically Active Centres in Porous Oxides: Design and Performance of Highly Selective New Catalysts"; Chem. Commun.; 2001; pp. 675-687.

Lorkovic, Ivan et al.; "C1 Coupling via Bromine Activation and Tandem Catalytic Condensation and Neutralization over CaO/Zeolite Composites"; Chem. Commun., 2004; pp. 566-567.

Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.

Weissermel, Klaus et al.; "Industrial Organic Chemistry"; 3rd Edition 1997. pp. 160-162, and 208.

Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.

Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.

Abstract of EP 1474371, Integrated process for synthesizing alcohols, ethers, and olefins from alkanes, Publication date: Nov. 10, 2004, Inventor: Zhou et al., esp@cenet database—worldwide.

Abstract of EP 1404636, Integrated process for synthesizing alcohols and ethers from alkanes, Publication date: Apr. 7, 2004, Inventor: Zhou et al., esp@cenet database—worldwide.

Abstract of CA 2447761 A1, Oxidative halogenation of C1 hydrocarbons to halogenated C1 hydrocarbons and integrated processes related thereto, Publication date: Nov. 28, 2002, Inventor: Hickman et al.

Abstract of CA 2471295 A1, Integrated process for synthesizing alcohols, ethers, and olefins from alkanes, Publication date: Jul. 31, 2003, Inventor: Sherman et al.

Abstract of EP 1435349 A2, Integrated process for synthesizing alcohols and ethers from alkanes, Publication date: Jul. 7, 2004, Inventor: Zhou et al.

Abstract of JP 2004-529189 (best available copy).

Abstract of GB 998681 (A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jul. 3, 1980, Inventor: Shigeo et al, http://www19.ipdl.inpit.go.jp/PA1/result. . . .

Hannus; "Adsorption and Transformation of Halogenated Hydrocarbons Over Zeolites", Applied Catalysis A: General 189; 1999; XP-002634422; pp. 263-276.

Howe; "Zeolite Catalysts for Dehalogenation Processes"; Applied Catalysis A: General 271; 2004; XP-002634421; pp. 3-11.

Li et al.; "Pyrolysis of Halon 1301 Over Zeolite Catalysts"; Microporous and Mesoporous Materials 35-36; 2000; XP-002634423; pp. 219-226.

U.S. Office Communication from U.S. Appl. No. 12/112,926 dated Jan. 7, 2011.

U.S. Office Communication from U.S. Appl. No. 12/502,024 dated May 31, 2011.

U.S. Office Communication from U.S. Appl. No. 12/715,526 dated Feb. 17, 2011.

U.S. Office Communication from U.S. Appl. No. 12/715,526 dated May 24, 2011.

U.S. Office Communication from U.S. Appl. No. 12/139,135 dated Apr. 14, 2011.

U.S. Office Communication from U.S. Appl. No. 12/715,526 dated Jan. 4, 2012.

U.S. Office Communication from U.S. Appl. No. 12/477,307 dated Feb. 27, 2012.

* cited by examiner

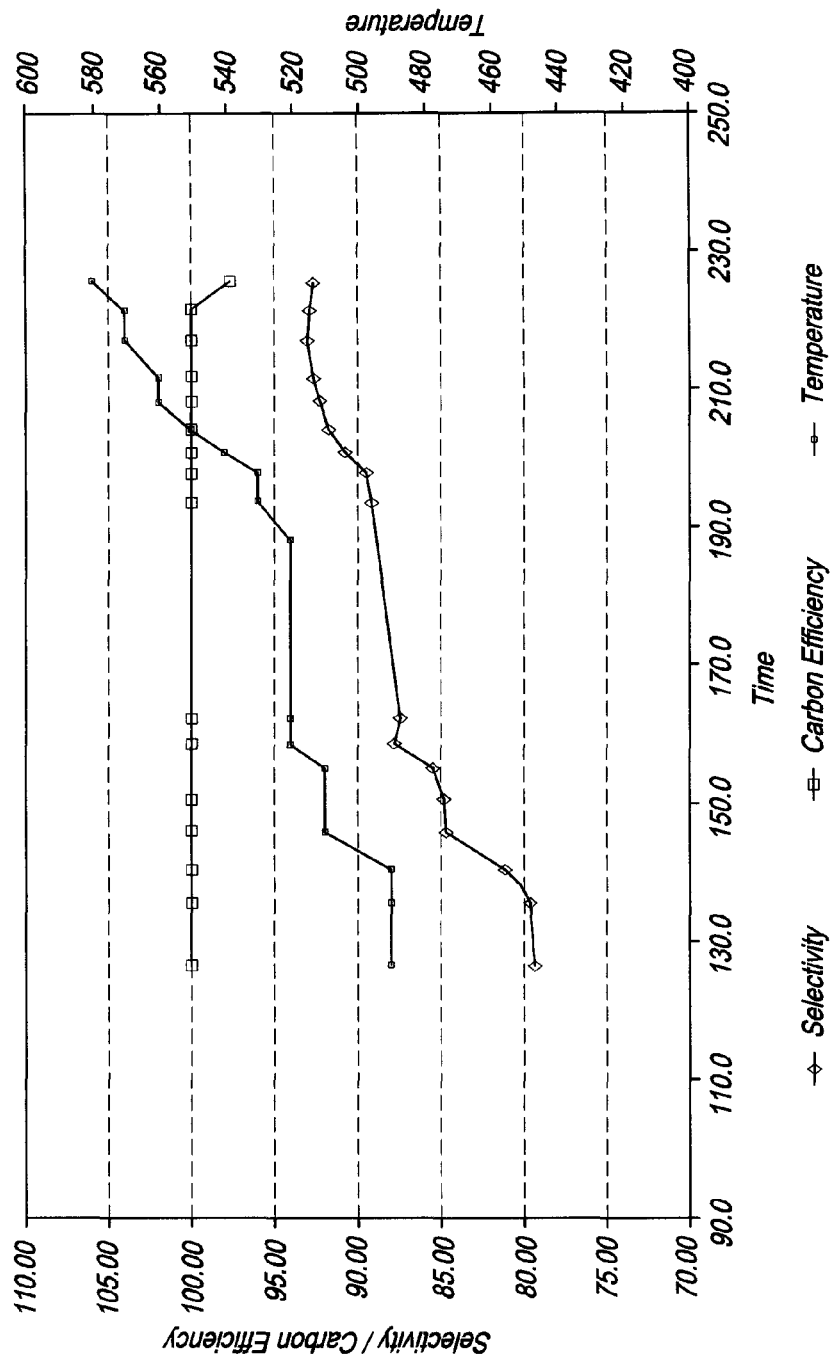

US 8,173,851 B2

PROCESSES FOR CONVERTING GASEOUS ALKANES TO LIQUID HYDROCARBONS

REFERENCE TO RELATED PATENT APPLICATION

This application is a continuation-in-part of Ser. No. 12/138,877, filed Jun. 13, 2008, now U.S. Pat. No. 7,674,941 issued on Mar. 9, 2010 and entitled "Processes for Converting Gaseous Alkanes to Liquid Hydrocarbons", which is a continuation-in-part of Ser. No. 12/112,926, filed Apr. 30, 2008, now U.S. Pat. No. 8,008,535 issued on Aug. 30, 2011 and entitled "Process for Converting Gaseous Alkanes to Olefins" which is a continuation of U.S. patent application Ser. No. 11/254,438 filed on Oct. 19, 2005 now abandoned and entitled "Process for Converting Gaseous Alkanes to Olefins and Liquid Hydrocarbons," which is a continuation-in-part of Ser. No. 11/101,886, filed Apr. 8, 2005, now U.S. Pat. No. 7,348,464 issued on Mar. 25, 2008 and entitled "Process for Converting Gaseous Alkanes to Liquid Hydrocarbons," which is a continuation-in-part of Ser. No. 10/826,885, filed Apr. 16, 2004, now U.S. Pat. No. 7,244,867 issued on Jul. 17, 2007 and entitled "Process for Converting Gaseous Alkanes to Liquid Hydrocarbons."

This application is related to the following copending patent applications: U.S. patent application Ser. No. 11/778,479 filed on Jul. 16, 2007 and entitled "Process for Converting Gaseous Alkanes to Liquid Hydrocarbons"; U.S. patent application Ser. No. 11/957,261 filed on Dec. 14, 2007 and entitled "Process for Converting Gaseous Alkanes to Liquid Hydrocarbons"; U.S. patent application Ser. No. 12/123,924 filed on May 20, 2008 and entitled "Process for Converting Gaseous Alkanes to Liquid Hydrocarbons" and U.S. patent application Ser. No. 12/139,135 filed on Jun. 13, 2008 and entitled "Hydrogenation of Multi-Brominated Alkanes."

BACKGROUND OF THE INVENTION

The present invention relates to processes for converting lower molecular weight alkanes to olefins, higher molecular weight hydrocarbons, or mixtures thereof that may be useful as fuels or monomers and intermediates in the production of fuels or chemicals, such as lubricants and fuel additives, and more particularly, in one or more embodiments, to processes wherein a gas that comprises lower molecular weight alkanes is reacted with bromine to form alkyl bromides and hydrobromic acid in a manner to effectively reduce formation of multi-brominated species to a level that can be tolerated in subsequent process steps.

Natural gas which is primarily composed of methane and other light alkanes has been discovered in large quantities throughout the world. Many of the locales in which natural gas has been discovered are far from populated regions which have significant gas pipeline infrastructure or market demand for natural gas. Due to the low density of natural gas, transportation thereof in gaseous form, for example, by pipeline or as compressed gas in vessels, is expensive. Accordingly, practical and economic limits exist to the distance over which natural gas may be transported in its gaseous form. Cryogenic liquefaction of natural gas (often referred to as "LNG") is often used to more economically transport natural gas over large distances. However, this LNG process is expensive and there are limited regasification facilities in only a few countries that are equipped to import LNG.

Another use of methane is as feed to processes for the production of methanol. Methanol can be made commercially via conversion of methane to synthesis gas (CO and $H_2$) (often referred to as "syn-gas") at high temperatures (e.g., approximately 1000° C.) followed by synthesis at high pressures (approximately 100 atmospheres). There are several types of technologies for the production of synthesis gas from methane. Among these are steam-methane reforming (SMR), partial oxidation (POX), autothermal reforming (ATR), gas-heated reforming (GHR), and various combinations thereof. There are advantages and disadvantages associated with each. For instance, SMR and GHR usually operate at high pressures and temperatures, generally in excess of 600° C., and are endothermic reactions thus requiring expensive furnaces or reactors containing special heat and corrosion-resistant alloy heat-transfer tubes filled with expensive reforming catalyst and high-temperature heat supplied from a source external to the reactor, such as from the combustion of natural gas, as is often utilized in SMR. POX and ATR processes usually operate at high pressures and even higher temperatures, generally in excess of 1000° C. and utilize exothermic reactions in which a significant fraction of the hydrocarbon feed is converted to CO2 and a large amount of high-temperature waste-heat must be rejected or recovered, thus complex and costly refractory-lined reactors and high-pressure waste-heat boilers to quench and cool the synthesis gas effluent are required. Also, significant capital cost and large amounts of power are required for compression of oxygen or air to these high-pressure processes. Thus, due to the high temperatures and pressures involved, synthesis gas technology is generally viewed as expensive, resulting in a high cost methanol product. This cost can limit higher-value uses of the methanol, such as for chemical feedstocks and solvents. Furthermore, it is generally thought that production of synthesis gas can be thermodynamically and chemically inefficient, in that it can produce large excesses of waste heat and unwanted carbon dioxide, which lowers the carbon conversion efficiency of the process. Fischer-Tropsch Gas-to-Liquids (GTL) technology can also be used to convert synthesis gas to heavier liquid hydrocarbons, however investment cost for this process at this point in time are higher than other types of processes. In each case, the production of synthesis gas represents a large fraction of the capital costs for these methane conversion processes and limits the maximum carbon efficiencies that these processes can attain.

Numerous alternatives to the conventional production of synthesis gas as a route to methanol or higher molecular weight hydrocarbons have been proposed. However, to date, none of these alternatives has attained commercial status for various reasons. Some of the previous alternative prior-art methods are directed to reacting a lower alkane, such as methane, with a metal halide to form an alkyl halide and hydrogen halide, which can be reacted with magnesium oxide to form corresponding alkanols. Halogenation of methane using chlorine as the halogen usually results in poor selectivity to the monomethyl halide ($CH_3Cl$), but rather produces unwanted by-products such as $CH_2Cl_2$ and $CHCl_3$. These are thought to be difficult to convert or require severe limitation of conversion per pass, and hence very high recycle rate.

Other existing processes propose the catalytic chlorination or bromination of methane as an alternative to generation of synthesis gas (CO and $H_2$). To improve the selectivity of a methane halogenation step in an overall process for the production of methanol, one process teaches the use of bromine, generated by thermal decomposition of a metal bromide, to brominate alkanes in the presence of excess alkanes, which results in improved selectivity to mono-halogenated intermediates such as methyl bromide. To avoid the drawbacks of utilizing fluidized beds of moving solids, the process utilizes a circulating liquid mixture of metal chloride hydrates and metal bromides. Other processes are also capable of attaining higher selectivity to mono-halogenated intermediates by the use of bromination. The resulting alkyl bromides intermediates such as methyl bromide, are further converted to the corresponding alcohols and ethers, by reaction with metal oxides in circulating beds of moving solids. Another embodiment of such processes avoids the drawbacks of moving beds by utilizing a zoned reactor vessel containing a fixed bed of metal bromide/oxide solids that is operated cyclically in four steps. While certain ethers, such as dimethylether (DME) are a promising potential diesel engine fuel substitute, as of yet, there currently exists no substantial market for DME, and hence an expensive additional catalytic process conversion step would be required to convert DME into a currently marketable product. Other processes have been proposed which circumvent the need for production of synthesis gas, such as U.S. Pat. No. 4,467,130 to Olah in which methane is catalytically condensed into gasoline-range hydrocarbons via catalytic condensation using superacid catalysts. However, none of these earlier alternative approaches have resulted in commercial processes.

In some instances, substituted alkanes, in particular methanol, can be converted to olefins and gasoline boiling-range hydrocarbons over various forms of crystalline alumino-silicates also known as zeolites. In the Methanol to Gasoline (MTG) process, a shape selective zeolite catalyst, ZSM-5, is used to convert methanol to gasoline. Coal or methane gas can thus be converted to methanol using conventional technology and subsequently converted to gasoline. However due to the high cost of methanol production, and at current or projected prices for gasoline, the MTG process is not considered economically viable. Thus, a need exists for an economic process for the conversion of methane and other alkanes found in various gas feeds to olefins, higher molecular weight hydrocarbons or mixtures thereof which have an increased value and are more economically transported thereby significantly aiding development of remote natural gas reserves. A further need exists for an efficient manner of brominating alkanes present in various gas feeds, such as natural gas, to mono-brominated alkanes while minimizing the amount of undesirable multi-halogenated alkanes formed.

SUMMARY OF THE INVENTION

To achieve the foregoing and other objects, and in accordance with the purposes of the present invention, as embodied and broadly described herein, one characterization of the present invention is a process comprising contacting bromine with gaseous alkanes containing methane at a first temperature sufficient to form bromination products comprising alkyl bromides and reacting the alkyl bromides with a portion of the methane in the presence of a catalyst and at a second temperature sufficient to convert at least a portion of poly-brominated alkanes present in the alkyl bromides to mono-brominated alkanes.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings:

FIG. 21 is a graph of carbon efficiencies and monobromination selectivity for varying temperatures used in the bromination stage of an embodiment of the processes of the present invention.

DETAILED DESCRIPTION OF THE PREFERRED EMBODIMENTS

Figure 1:
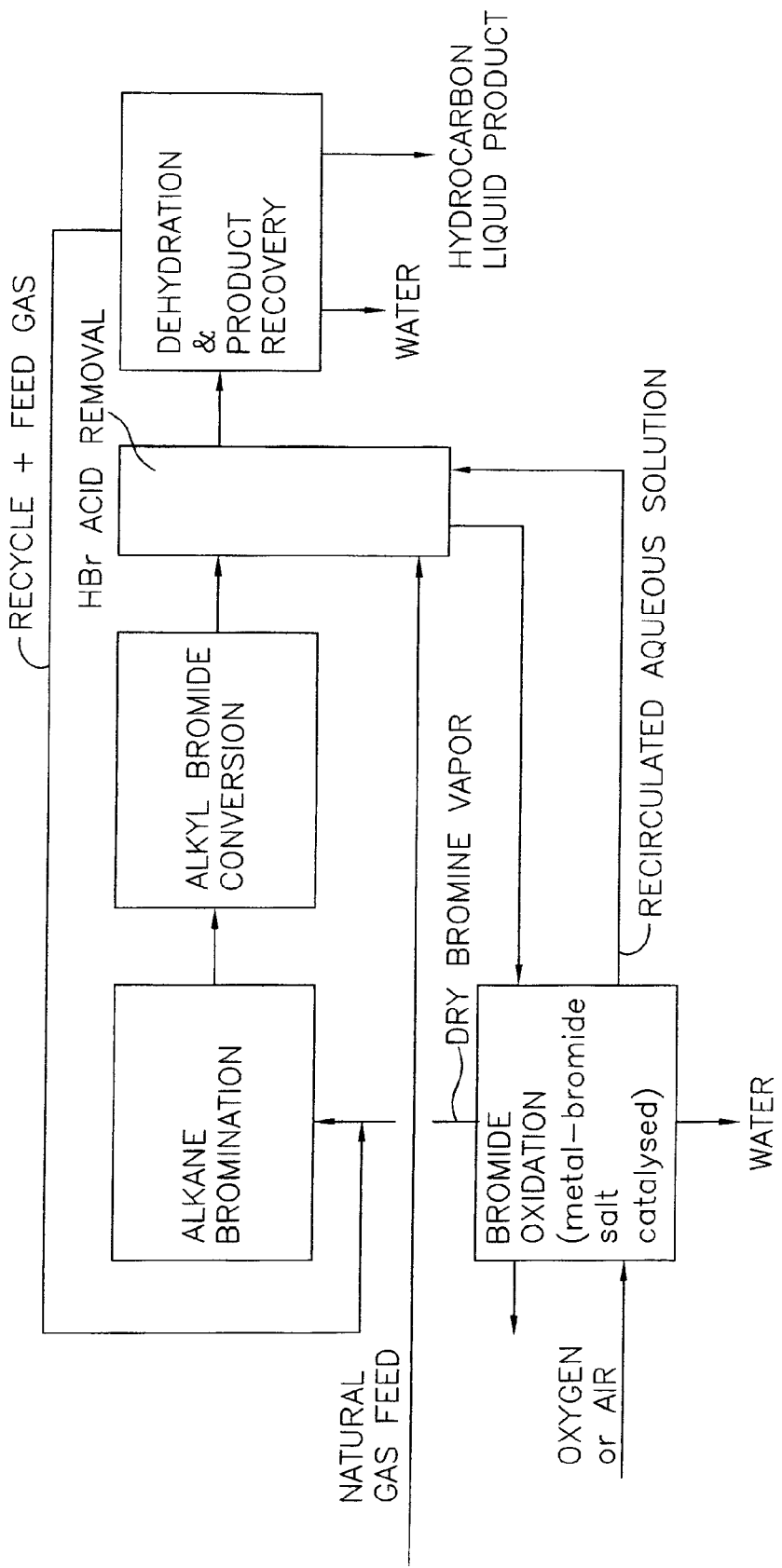
FIG. 1 is a simplified block flow diagram of the processes of the present invention.

The term "high molecular weight hydrocarbons" as used herein refers to hydrocarbons comprising $C_3$ chains and longer hydrocarbon chains. In some embodiments, the higher molecular weight hydrocarbons may be used directly as a product (e.g., LPG, motor fuel, etc.). In other instances, the higher molecular weight hydrocarbon stream may be used as an intermediate product or as a feedstock for further processing. In other instances, the higher molecular weight hydrocarbons may be further processed, for example, to produce gasoline grade fuels, diesel grade fuels, and fuel additives. In some embodiments, the higher molecular weight hydrocarbons obtained by the processes of the present invention can be used directly as a motor gasoline fuel having a substantial aromatic content, as a fuel blending stock, or as feedstock for further processing such as an aromatic feed to a process producing aromatic polymers such as polystyrene or related polymers an olefin feed to a process for producing polyolefins. The term "olefins" as used herein refers to hydrocarbons that contain two to six carbon atoms and at least one carbon-carbon double bond. The olefins may be further processed if desired. For instance, in some instances, the olefins produced by the processes of the present invention may be further reacted in a polymerization reaction (for example, a reaction using a metallocene catalyst) to produce poly(olefins), which may be useful in many end products such as plastics or synthetic lubricants.

The end use of the high molecular weight hydrocarbons, the olefins or mixtures thereof may depend on the particular catalyst employed in the oligomerization portion of the methods discussed below, as well as the operating parameters employed in the process. Other uses will be evident to those skilled in the art with the benefit of this disclosure.

In some embodiments, the present invention comprises reacting a feed gas stream with bromine from a suitable bromine source to produce alkyl bromides. As used herein, the term "alkyl bromides" refers to mono-, di-, and tri-brominated alkanes, and combinations of these. Poly-brominated alkanes include di-brominated alkanes, tri-brominated alkanes and mixtures thereof. These alkyl bromides may then be reacted over suitable catalysts so as to form olefins, higher molecular weight hydrocarbons or mixtures thereof.

Lower molecular weight alkanes may be used as a feedstock for the methods described herein. A suitable source of lower molecular weight alkanes may be natural gas. As utilized throughout this description, the term "lower molecular weight alkanes" refers to methane, ethane, propane, butane, pentane or mixtures of two or more of these individual alkanes. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or chlathrates, gas derived from anaerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

Suitable sources of bromine that may be used in various embodiments of the present invention include, but are not limited to, elemental bromine, bromine salts, aqueous hydrobromic acid, metal bromide salts, and the like. Combinations may be suitable, but as recognized by those skilled in the art, using multiple sources may present additional complications. Certain embodiments of the methods of the invention are described below. Although major aspects of what is believed to be the primary chemical reactions involved in the methods are discussed in detail as it is believed that they occur, it should be understood that side reactions may take place. One should not assume that the failure to discuss any particular side reaction herein means that such side reaction does not occur. Conversely, those that are discussed should not be considered exhaustive or limiting. Additionally, although figures are provided that schematically show certain aspects of the methods of the present invention, these figures should not be viewed as limiting on any particular method of the invention.

A block flow diagram generally depicting the processes of the present invention is illustrated in FIG. 1 and depicts some aspects of certain embodiments of the processes of the present invention. In accordance with the general depiction of the processes of the present invention as illustrated in FIG. 1, a gas stream containing lower molecular weight alkanes, comprised of a mixture of a feed gas plus a recycled gas stream, and a dry bromine vapor are reacted in an alkyl bromination stage to produce alkyl bromides and hydrogen bromide. The resultant alkyl bromides are reacted over a suitable catalyst in the presence of hydrogen bromide in an alkyl bromide conversion stage to form olefins, higher molecular weight hydrocarbons or mixtures thereof. The particular olefins and higher molecular weight hydrocarbons produced will be dependent upon the catalyst employed in the alkyl bromide conversion stage, the composition of the alkyl bromides introduced into this stage and the exact operating parameters employed in this stage. The mixture of hydrogen bromide and olefins, higher molecular weight hydrocarbons or mixtures thereof are contacted with an aqueous solution in a hydrogen bromide (HBr) removal stage to remove hydrogen bromide from the olefins and higher molecular weight hydrocarbons. The resultant aqueous solution having hydrobromic acid dissolved therein is also contacted with a feed gas in this HBr removal stage to remove any residual hydrocarbons from the aqueous solution.

The feed gas, residual hydrocarbons and olefins, higher molecular weight hydrocarbons or mixtures thereof are conveyed to a dehydration and product recovery unit wherein water is removed from the remaining constituents. The feed gas and primarily methane and ethane hydrocarbons are then separated from the olefins, higher molecular weight hydrocarbons or mixtures thereof and conveyed to the alkane bromination stage of the present invention. The remaining olefins, higher molecular weight hydrocarbons or mixtures thereof are removed from the dehydration and product recovery stage for use as a fuel, a fuel blend or for further petrochemical or fuel processing.

As further generally illustrated in FIG. 1, the aqueous solution containing hydrobromic acid is conveyed to a bromide oxidation stage. The aqueous solution that is used to contact the olefins higher molecular weight hydrocarbons or mixtures thereof may be water, water containing dissolved hydrogen bromide, or may contain a partially oxidized metal bromide salt. In the case of the aqueous solution containing dissolved hydrogen bromide, this solution may be vaporized and then be passed through a bed of a partially oxidized metal bromide salt in the bromide oxidation stage of the process. In the case of the aqueous solution containing partially-oxidized metal bromide salt, hydrogen bromide that is dissolved in the aqueous solution is neutralized by the partially oxidized metal bromide salt to yield a metal bromide salt and water. The resultant metal bromide salt is then contacted with oxygen or air in the bromide oxidation stage of the present invention to yield elemental bromine which may be recycled to the alkane bromination stage as a dry bromine vapor and a partially oxidized metal bromide salt which may be used to neutralize and remove hydrogen bromide from the aqueous solution used to contact the olefins, higher molecular weight hydrocarbons or mixtures thereof produced by the process. Effluent water may also be removed from this stage.

Figure 2:
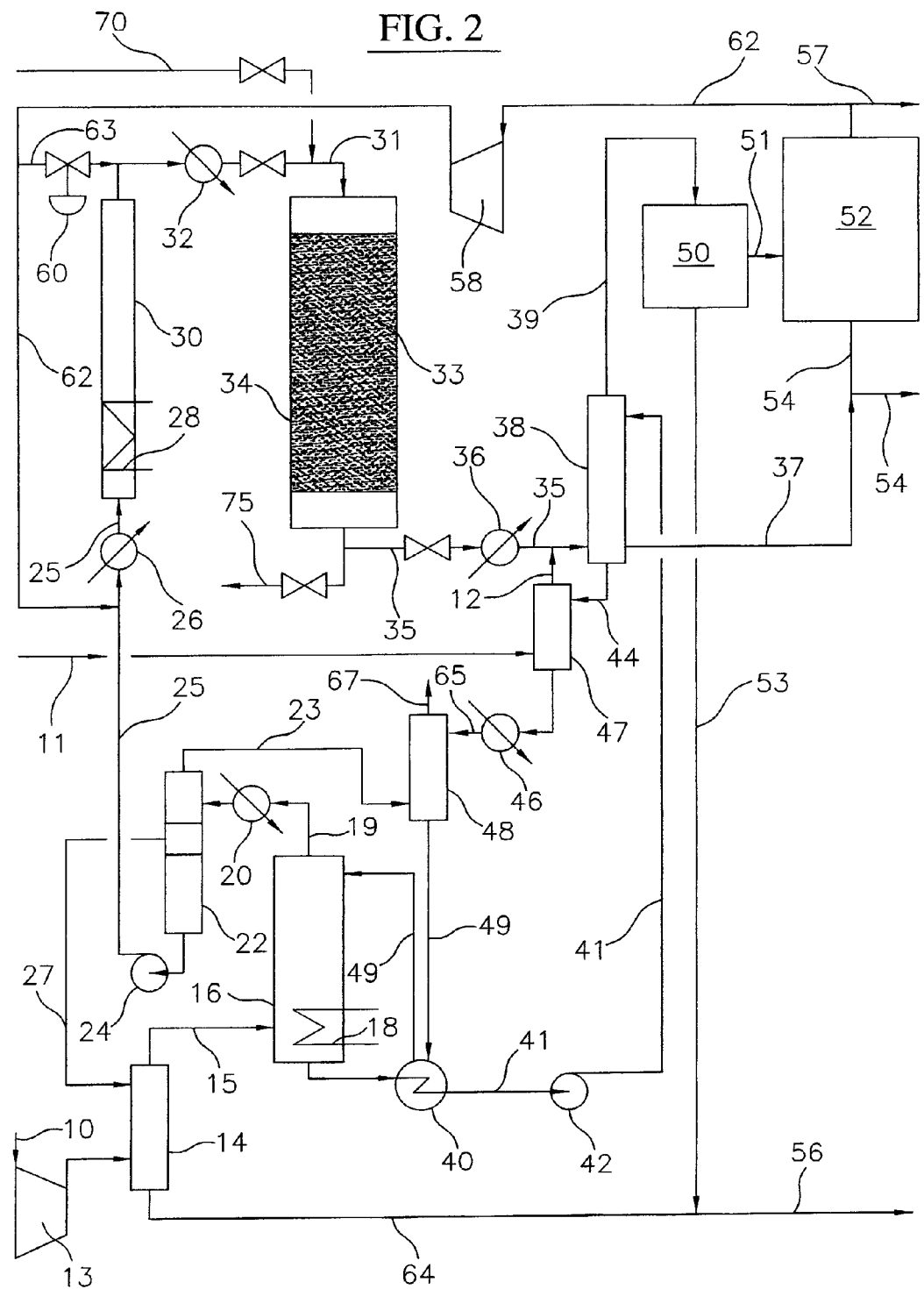
FIG. 2 is a schematic view of one embodiment of the processes of the present invention.

Referring to FIG. 2, a gas stream comprising lower molecular weight alkanes (which, in some embodiments, may include a mixture of a feed gas plus a recycled gas stream) at a pressure in the range of about 1 bar to about 75 bar, may be transported or conveyed via line, pipe or conduit 62, mixed with dry bromine liquid transported via line 25 and pump 24, and passed to heat exchanger 26 wherein the liquid bromine is vaporized. The mixture of lower molecular weight alkanes and dry bromine vapor can then be fed to reactor 30. Preferably, the molar ratio of lower molecular weight alkanes to dry bromine vapor in the mixture introduced into reactor 30 is in excess of about 2.5:1, and more preferably in excess of about 4:1, and most preferably in excess of about 7:1. Reactor 30 may have an inlet pre-heater zone 28 that can heat the mixture to a reaction initiation temperature in the range of about 250° C. to about 400° C.

In first reactor 30, the lower molecular weight alkanes may be reacted exothermically with dry bromine vapor at a temperature in the range of about 250° C. to about 600° C., and at a pressure in the range of about 1 bar to about 80 bar, and more preferably about 1 bar to 30 bar, to produce gaseous alkyl bromides and hydrobromic acid vapors. As will be evident to a skilled artisan with the benefit of this disclosure, the bromination reaction in first reactor 30 may be an exothermic reaction or a catalytic reaction. Non-limiting examples of suitable catalysts that may be used in first reactor 30 include platinum, palladium, or supported non-stiochiometric metal oxy-halides, such as $FeO_xBr_y$ or $FeO_xCl_y$, or supported metal oxyhalides, such as $TaOF_3$, $NbOF_3$, $ZrOF_2$, $SbOF_3$ as described in Olah, et al, J. Am. Chem. Soc. 1985, 107, 7097-7105. It is believed that the upper limit of the operating temperature range may be greater than the upper limit of the reaction initiation temperature range to which the feed mixture is heated due to the exothermic nature of the bromination reaction. In the case of methane, it is believed that the formation of methyl bromide occurs in accordance with the following general overall reaction:

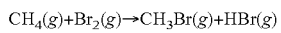

Due to the free-radical mechanism of the gas-phase bromination reaction, di-bromomethane and some tri-bromomethane and other alkyl bromides are also formed. However, this reaction in accordance with the processes of the present invention often occurs with a relatively high degree of selectivity to methyl bromide due to the alkane to bromine ratio employed in first reactor 30. For example, in the case of the bromination of methane, a methane to bromine ratio of about 6:1 is believed to increase the selectivity to mono-halogenated methyl bromide to average approximately 88%, depending on reaction conditions, such as residence time, temperature, and turbulent mixing. At these conditions, some dibromomethane and only extremely small amounts of tri-bromomethane approaching the detectable limits also may be formed in the bromination reaction. If a lower methane to bromine ratio of approximately 2.6 to 1 is utilized, selectivity to the mono-halogenated methyl bromide may fall to the range of approximately 65 to 75% depending on other reaction conditions. At a methane to bromine ratio significantly less than about 2.5 to 1, unacceptable low selectivities to methyl bromide occurs, and, moreover, significant formation of undesirable di-bromomethane, tri-bromomethane, and carbon soot is observed. The residence time of the reactants in first reactor 30 necessary to achieve such selectivity to mono-halogenated methyl bromide is relatively short and may be as little as 1-5 seconds under adiabatic reaction conditions. Higher alkanes, such as ethane, propane and butane, also may be brominated, resulting in mono and multiple brominated species such as ethyl bromides, propyl bromides and butyl bromides. Further, in some embodiments, the dry bromine vapor that is fed into first reactor 30 may be substantially water-free. Applicant has discovered that, at least in some instances, this may be preferred because it appears that elimination of substantially all water vapor from the bromination step in first reactor 30 substantially eliminates the formation of unwanted carbon dioxide. This may increase the selectivity of alkane bromination to alkyl bromides, thus possibly eliminating the large amount of waste heat generated in the formation of carbon dioxide from alkanes.

An effluent that comprises alkyl bromides and hydrogen bromide may be withdrawn from the first reactor via line 31. This effluent may be partially cooled in heat exchanger 32 before flowing to a second reactor 34. The temperature to which the effluent is partially cooled in heat exchanger 34 is in the range of about 150° C. to about 390° C. when it is desired to convert the alkyl bromides to higher molecular weight hydrocarbons in second reactor 34, or to range of about 150° C. to about 450° C. when it is desired to convert the alkyl bromides to olefins a second reactor 34. Second reactor 34 is thought to oligomerize the alkyl units so as to form products that comprise olefins, higher molecular weight hydrocarbons or mixtures thereof. In second reactor 34, the alkyl bromides are reacted exothermically at a temperature range of from about 150° C. to about 450° C., and a pressure in the range of about 1 to 80 bar, over a suitable catalyst to produce desired products (e.g., olefins and higher molecular weight hydrocarbons).

The catalyst used in reactor 34 may be any of a variety of suitable materials for catalyzing the conversion of the brominated alkanes to product hydrocarbons. In certain embodiments, second reactor 34 may comprise a fixed bed 33 of the catalyst. A fluidized-bed of synthesis catalyst may also be used in certain circumstances, particularly in larger applications and may have certain advantages, such as constant removal of coke and a steady selectivity to product composition. Examples of suitable catalysts include a fairly wide range of materials that have the common functionality of being acidic ion-exchangers and which also contain a synthetic crystalline alumino-silicate oxide framework. In certain embodiments, a portion of the aluminum in the crystalline alumino-silicate oxide framework may be substituted with magnesium, boron, gallium and/or titanium. In certain embodiments, a portion of the silicon in the crystalline alumino-silicate oxide framework may be optionally substituted with phosphorus. The crystalline alumino-silicate catalyst generally may have a significant anionic charge within the crystalline alumino-silicate oxide framework structure which may be balanced, for example, by cations of elements selected from the group H, Li, Na, K or Cs or the group Mg, Ca, Sr or Ba or the group La or Ce. Although zeolitic catalysts may be commonly obtained in a sodium form, a protonic or hydrogen form (via ion-exchange with ammonium hydroxide, and subsequent calcining) is preferred, or a mixed protonic/sodium form may also be used. The zeolite may also be modified by ion exchange with other alkali metal cations, such as Li, K, or Cs, with alkali-earth metal cations, such as Mg, Ca, Sr, or Ba, or with transition metal cations, such as Fe, Ni, Cu, Mn, V, W or with rare-earth metal cations La or Ce. Such subsequent ion-exchange, may replace the charge-balancing counter-ions, but furthermore may also partially replace ions in the oxide framework resulting in a modification of the crystalline make-up and structure of the oxide framework. The crystalline alumino-silicate or substituted crystalline alumino-silicate may include a microporous or mesoporous crystalline aluminosilicate, but, in certain embodiments, may include a synthetic microporous crystalline zeolite, and, for example, being of the MFI structure such as ZSM-5. Moreover, the crystalline alumino-silicate or substituted crystalline alumino-silicate, in certain embodiments, may be subsequently impregnated with an aqueous solution of a Mg, Ca, Sr, Ba, La or Ce salt. In certain embodiments, the salts may be a halide salt, such as a bromide salt, such as MgBr2, CeBr3 or other solid compound having Lewis acid functionality which has been found to reduce the deactivation rate of the base crystalline alumino-silicate or substituted alumino-silicate catalyst. Optionally, the crystalline alumino-silicate or substituted crystalline alumino-silicate may also contain between about 0.1 to about 1 weight % Pt, about 0.1 to 5 weight % Pd, or about 0.1 to about 5 weight % Ni in the metallic state. Although, such materials are primarily initially crystalline, it should be noted that some crystalline catalysts may undergo some loss of crystallinity either due to initial ion-exchange or impregnation or due to operation at the reaction conditions or during regeneration and hence may also contain significant amorphous character, yet still retain significant, and in some cases improved activity.

The particular catalyst used in second reactor 34 will depend, for example, upon the particular product hydrocarbons that are desired. For example, when product hydrocarbons having primarily C3, C4 and $C_{5+}$ gasoline-range aromatic compounds and heavier hydrocarbon fractions are desired, a ZSM-5 zeolite catalyst may be used. When it is desired to produce product hydrocarbons comprising a mixture of olefins and $C_{5+}$ products, an X-type or Y-type zeolite catalyst or SAPO zeolite catalyst may be used. Examples of suitable zeolites include an X-type, such as 10-X, or Y-type zeolite, although other zeolites with differing pore sizes and acidities, may be used in embodiments of the present invention.

In addition to the catalyst, the temperature at which the second reactor 34 is operated is an important parameter in determining the selectivity and conversion of the reaction to the particular product desired. For example, when a X type or Y type zeolite catalyst is used and it is desired to produce olefins, it may be advisable to operate second reactor 34 at a temperature within the range of about 250° C. to 500° C. Alternatively, in an embodiment involving a ZSM-5 zeolite catalyst operating in a slightly lower temperature range of about 250° C. to 450° C., cyclization reactions in the second reactor occur such that the $C_{7+}$ fractions contain primarily substituted aromatics and also light alkanes primarily in the $C_3$ to $C_{5+}$ range. Surprisingly, very little ethane or $C_2$, $-C_3$ olefin components are found in the products.

In the example of a gas mixture containing methyl bromide reacting over a ZSM-5 catalyst at a GHSV in the range of about 100 to 2000 hr−1, at increasing temperatures approaching 400° C., methyl bromide conversion increases towards the range of about 90% to 98% or greater, however selectivity towards $C_{5+}$ hydrocarbons decreases and selectivity towards lighter products of the process, particularly increases. At temperatures exceeding 550° C., it is believed that a high conversion of methyl bromide to methane and carbonaceous, coke may occur. In the preferred operating temperature range of between about 350° C. and 450° C., as a byproduct of the reaction, a lesser amount of coke may build up on the catalyst over time during operation. Coke build-up may be problematic as it can lead to a decline in catalyst activity over a range of hours, up to hundreds of hours, depending on the reaction conditions and the composition of the feed gas. It is believed that higher reaction temperatures above about 400° C., associated with the formation of methane favor the thermal cracking of alkyl bromides and formation of carbon or coke, and hence, an increase in the rate of deactivation of the catalyst. Conversely, temperatures at the lower end of the range, particularly below about 350° C. may also contribute to deactivation due to a reduced rate of desorption of heavier products from the catalyst. Hence, operating temperatures within the range of about 350° C. to about 450° C., but preferably in the range of about 375° C. to about 425° C. in the second reactor 34 balance increased selectivity of the desired $C_{5+}$ hydrocarbons and lower rates of deactivation due to lesser carbonaceous coke formation or heavy product accumulation on the catalyst, against higher conversion per pass, which minimizes the quantity of catalyst, recycle rates and equipment size required.

In some embodiments, the catalyst may be periodically regenerated in situ. One suitable method of regenerating the catalyst is to isolate reactor 34 from the normal process flow, purge it with an inert gas via line 70 at a pressure in a range from about 1 to about 5 bar at an elevated temperature in the range of about 400° C. to about 650° C. This should remove unreacted alkyl bromides and heavier hydrocarbon products adsorbed on the catalyst insofar as is practical. Optionally, the catalyst then may be subsequently oxidized by addition of air or inert gas-diluted oxygen to reactor 34 via line 70 at a pressure in the range of about 1 bar to about 5 bar at an elevated temperature in the range of about 400° C. to about 650° C. Carbon dioxide and residual air or inert gas may be vented from reactor 34 via line 75 during the regeneration period. In most cases it is preferable to route the regeneration off-gas from reactor 34 via line 75 to the oxidation portion of the process (not illustrated) such that trace amounts of bromine, resulting from oxidation of HBr or alkyl bromides adsorbed on the catalyst, may be recovered and reused within the process.

The effluent from reactor 34, which comprises hydrogen bromide and olefins, higher molecular weight hydrocarbons or mixtures thereof, may be withdrawn from the second reactor 34 via line 35. It can be cooled if desired to a temperature in the range of 0° C. to about 100° C. (for example, in exchanger 36). It may be combined with vapor effluent in line 12 from hydrocarbon stripper 47, which contains feed gas and residual hydrocarbons stripped-out by contact with the feed gas in hydrocarbon stripper 47. The combined vapor mixture can then be passed to a scrubber 38, wherein it may be contacted with a concentrated aqueous partially-oxidized metal bromide salt solution containing metal hydroxide, metal oxide, metal oxy-bromide species or mixtures of these substances, which may be transported to scrubber 38 via line 41 by any suitable means (such as pump 42). The preferred bromide salt is Fe(III), Cu(II) or Zn(II) salt, or mixtures thereof, as these are less expensive and readily oxidize at lower temperatures in the range of about 120° C. to about 180° C., beneficially allowing the use of glass-lined or fluoropolymer-lined equipment. As recognized by those skilled in the art however, Co(II), Ni(II), Mn(II), V(II), Cr(II) or other transition-metals that are capable of forming oxidizable bromide salts also may be suitable in the processes of the present invention. Alternatively, alkaline-earth metals which also form oxidizable bromide salts, such as Ca (II) or Mg(II), may be suitable as well. Optionally, any liquid hydrocarbons condensed in scrubber 38 may be skimmed and withdrawn in line 37, and then added to liquid hydrocarbons exiting the product recovery unit 52 in line 54. Hydrogen bromide should be dissolved in the aqueous solution, and then neutralized by the metal hydroxide, metal oxide, metal oxy-bromide, or mixtures of these species to yield metal bromide salt in solution and water. This can be removed from the scrubber 38 via line 44.

Any suitable method of dehydration and liquids recovery used to process natural gas or refinery gas streams to recover products such as olefins and higher molecular weight hydrocarbons, for example, solid-bed desiccant adsorption followed by refrigerated condensation, cryogenic expansion, or circulating absorption oil or other solvent, as, may be employed in the processes of the present invention. In some embodiments, the residual vapor stream comprising olefins, higher molecular weight hydrocarbons or mixtures thereof that is removed as effluent from the scrubber 38 may be forwarded via line 39 to dehydrator 50 to remove substantially all water via line 53 from the vapor stream. The water can be removed from dehydrator 50 via line 53. The dried vapor stream comprising the olefins, higher molecular weight hydrocarbons or mixtures thereof can be further passed to product recovery unit 52 (for example, via line 51) to recover olefins, the $C_{5+}$ gasoline-range hydrocarbon fraction or mixtures thereof as a liquid product in line 54. The residual vapor effluent from product recovery unit 52 can be split into a purge stream 57, which may be utilized as fuel for the process, and a recycled residual vapor, which can be compressed via compressor 58. The recycled residual vapor discharged from compressor 58 can be split into at least two fractions. If desired, a first fraction (that may be equal to at least 2.5 times the feed gas molar volume) can be transported via line 62 to be combined with dry liquid bromine conveyed by pump 24, heated in exchanger 26 to vaporize the bromine, and fed into first reactor 30. A second fraction can be drawn off of line 62 via line 63 (which can regulated by control valve 60), at a rate sufficient to dilute the alkyl bromide concentration to reactor 34 and absorb the heat of reaction such that reactor 34 is maintained at the selected operating temperature, preferably in the range of about 350° C. to about 450° C. In most instances, this temperature range appears to maximize conversion versus selectivity and to minimize the rate of catalyst deactivation due to the deposition of carbon. Thus, the dilution provided by the recycled vapor effluent permits selectivity of bromination in the first reactor 30 to be controlled in addition to moderating the temperature in second reactor 34.

Optionally, the water containing metal bromide salt in solution which is removed from scrubber 38 via line 44 can be passed to hydrocarbon stripper 47 wherein residual dissolved hydrocarbons can be stripped from the aqueous phase, e.g., by contact with incoming feed gas transported via line 11. After the stripping process, the stripped aqueous solution can be transported from hydrocarbon stripper 47 via line 65 to a heat exchanger (e.g., heat exchanger 46) to be cooled to a temperature in the range of about 0° C. to about 70° C. Cooling the stripped aqueous solution may be desirable because it may suppress the hydrogen bromide vapor pressure of the aqueous solution minimizing or substantially eliminating the loss thereof to the oxidation vent stream 67. The cooled stripped aqueous solution can be then passed to absorber 48 in which residual bromine can be recovered from vent stream in line 67. This recovered bromine can be recycled and used again in the process.

The aqueous solution effluent from scrubber 48 can be transported via line 49 to a heat exchanger 40 to be vaporized and/or preheated to a temperature in the range of about 100° C. to about 600° C., and most preferably in the range of about 120° C. to about 180° C. and passed to third reactor 16. Oxygen or air can be delivered via line 10 by blower or compressor 13 at a pressure in the range of about ambient to about 5 bar to bottom-heated bromine stripper 14 to strip residual bromine from water. Water is removed from stripper 14 in line 64 and is combined with water stream 53 from dehydrator 50 to form water effluent stream in line 56 which is removed from the process. The oxygen or air leaving bromine stripper 14 is fed via line 15 to reactor 16 which operates at a pressure in the range of about ambient to about 5 bar and at a temperature in the range of about 100° C. to about 600° C., but most preferably in the range of about 120° C. to about 180° C. so as to oxidize an aqueous metal bromide salt solution to yield elemental bromine and metal hydroxide, metal oxide, metal oxy-bromide, or mixtures of these species. As stated above, although any oxidizable bromide salt may be used, either alone or in combination with other bromide salts, the preferred metal of the bromide salt is Fe(III), Cu(II), or Zn(II), or mixtures thereof, as these are less expensive and readily oxidize at lower temperatures in the range of about 120° C. to about 180° C., allowing the use of glass-lined or fluoropolymer-lined equipment. Alternatively, alkaline-earth metals which also form oxidizable bromide salts, such as Ca (II) or Mg(II) could be used.

Hydrogen bromide reacts with the metal hydroxide, metal oxide, metal oxy-bromide, or mixtures of these species so formed to once again yield the metal bromide salt and water. Heat exchanger 18 in reactor 16 supplies heat to preheat the solution during start-up and may supply heat, to supplement the heat of reaction to vaporize water and strip bromine from the reactor 16. Thus, the overall reactions result in the net oxidation of hydrogen bromide produced in first reactor 30 and second reactor 34 to elemental bromine and water in the liquid phase catalyzed by the metal bromide/metal oxide or metal hydroxide operating in a catalytic cycle. In the case of the metal bromide being Fe(III)Br3, the reactions are believed to be:

$$Fe(+3a)+6Br(-a)+3H(+a)+3/2O2(g)=3Br2(g)+Fe(OH)3 \quad 1)$$

$$3HBr(g)+H_2O=3H(+a)+3Br(-a)+H_2O \quad 2)$$

$$3H(+a)+3Br(-a)+Fe(OH)3=Fe(+3a)+3Br(-a)+3H_2O \quad 3)$$

The elemental bromine and water and any residual oxygen or nitrogen (if air is utilized as the oxidant) leaving as vapor from the outlet of third reactor 16 via line 19, are cooled in condenser 20 at a temperature in the range of about 0° C. to about 70° C. and a pressure in the range of about ambient to 5 bar to condense the bromine and water and passed to three-phase separator 22. In three-phase separator 22, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus a substantially dry bromine vapor may be easily obtained by condensing liquid bromine and water, decanting water by simple physical separation and subsequently re-vaporizing liquid bromine.

Liquid bromine is pumped in line 25 from three-phase separator 22 via pump 24 to a pressure sufficient to mix with vapor stream 62. Thus bromine is recovered and recycled within the process. The residual oxygen or nitrogen and any residual bromine vapor which is not condensed exits three-phase separator 22 and is passed via line 23 to bromine scrubber 48, wherein residual bromine is recovered by solution into and by reaction with reduced metal bromides in the aqueous metal bromide solution stream 65. Water is removed from separator 22 via line 27 and introduced into stripper 14.

Figure 3:
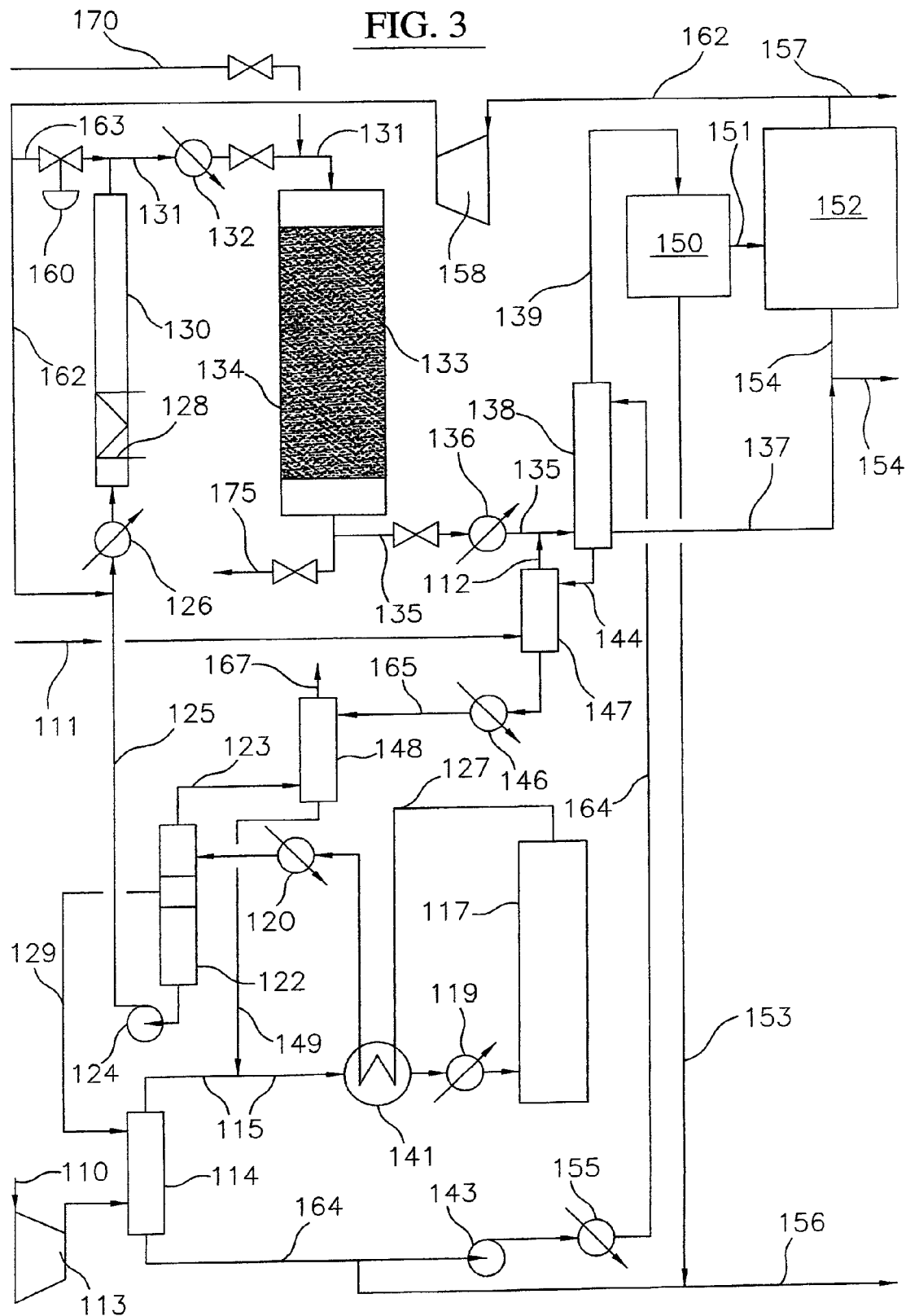
FIG. 3 is a schematic view of another embodiment of processes of the present invention.

In another embodiment of the invention, referring to FIG. 3, a gas stream containing lower molecular weight alkanes, comprised of mixture of a feed gas plus a recycled gas stream at a pressure in the range of about 1 bar to about 30 bar, is transported or conveyed via line, pipe or conduit 162, mixed with dry bromine liquid transported via pump 124 and passed to heat exchanger 126 wherein the liquid bromine is vaporized. The mixture of lower molecular weight alkanes and dry bromine vapor can be fed to reactor 130. Preferably, the molar ratio of lower molecular weight alkanes to dry bromine vapor in the mixture introduced into reactor 130 is in excess of about 2.5:1, more preferably in excess of about 4:1, and most preferably in excess of about 7:1. Optionally, reactor 130 has an inlet pre-heater zone 128, which can heat the mixture to a reaction initiation temperature in the range of about 250° C. to about 400° C.

In first reactor 130, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. As will be evident to a skilled artisan with the benefit of this disclosure, the bromination reaction in first reactor 30 may be an homogeneous gas-phase reaction or a heterogeneous catalytic reaction. Non-limiting examples of suitable catalysts that may be used in first reactor 30 include platinum, palladium, or supported non-stiochiometric metal oxy-halides, such as $FeO_xBr_y$ or $FeO_xCl_y$, or supported metal oxyhalides, such as $TaOF_3$, $NbOF_3$, $ZrOF_2$, $SbOF_3$ as described in Olah, et al, J. Am. Chem. Soc. 1985, 107, 7097-7105. The upper limit of the operating temperature range is greater than the upper limit of the reaction initiation temperature range to which the feed mixture is heated due to the exothermic nature of the bromination reaction. In the case of methane, the formation of methyl bromide is believed to occur in accordance with the following general reaction:

$$CH_4(g)+Br_2(g) \rightarrow CH_3Br(g)+HBr(g)$$

Due to the free-radical mechanism of the gas-phase bromination reaction, di-bromomethane and some tri-bromomethane and other alkyl bromides are also formed. However, this reaction in accordance with the processes of the present invention often occurs with a relatively high degree of selectivity to methyl bromide due to the alkane to bromine ratio employed in first reactor 130. For example, in the case of the bromination of methane, a methane to bromine ratio of about 6:1 is believed to increase the selectivity to mono-halogenated methyl bromide to average approximately 88%, depending on reaction conditions, such as residence time, temperature, and turbulent mixing. At these conditions, some dibromomethane and only extremely small amounts of tri-bromomethane approaching the detectable limits also may be formed in the bromination reaction. If a lower methane to bromine ratio of approximately 2.6 to 1 is utilized, selectivity to the mono-halogenated methyl bromide may fall to the range of approximately 65 to 75% depending on other reaction conditions. At a methane to bromine ratio significantly less than about 2.5 to 1, unacceptable low selectivities to methyl bromide occurs, and, moreover, significant formation of undesirable di-bromomethane, tri-bromomethane, and carbonaceous soot may be observed. The residence time of the reactants in first reactor 130 necessary to achieve such selectivity to mono-halogenated methyl bromide is relatively short and may be as little as 1-5 seconds under adiabatic reaction conditions. Higher alkanes, such as ethane, propane and butane, also may be brominated, resulting in mono and multiple brominated species such as ethyl bromides, propyl bromides and butyl bromides. Further, in some embodiments, the dry bromine vapor that is fed into first reactor 130 may be substantially water-free. Applicant has discovered that, at least in some instances, this may be preferred because it appears that elimination of substantially all water vapor from the bromination step in first reactor 130 substantially eliminates the formation of unwanted carbon dioxide. This may increase the selectivity of alkane bromination to alkyl bromides, thus possibly eliminating the large amount of waste heat generated in the formation of carbon dioxide from alkanes.

The effluent that contains alkyl bromides and hydrobromic acid can be withdrawn from the first reactor 130 via line 131. In some embodiments, this effluent can be partially cooled to a temperature in the range of about 150° C. to 500° C. in heat exchanger 132 before flowing to a second reactor 134. The temperature to which the effluent is partially cooled in heat exchanger 132 is in the range of about 150° C. to about 400° C. when it is desired to convert the alkyl bromides to higher molecular weight hydrocarbons in second reactor 134, or to range of about 150° C. to about 450° C. when it is desired to convert the alkyl bromides to olefins a second reactor 134. Second reactor 134 is thought to dehydrohalogenate and oligomerize the resultant alkyl moieties so as to form products that comprise olefins, higher molecular weight hydrocarbons or mixtures thereof. The catalyst used in second reactor 134 and the temperature at which the reactor 134 is operated can be selected to achieve the desired hydrocarbon product as described above with respect to reactor 34. In certain embodiments, second reactor 134 may comprise a fixed bed 133 of the catalyst. A fluidized-bed of synthesis catalyst may also be used in certain circumstances, particularly in larger applications and may have certain advantages, such as constant removal of coke and a steady selectivity to product composition.

The catalyst may be periodically regenerated in situ, by isolating reactor 134 from the normal process flow, purging with an inert gas via line 170 at a pressure in the range of about 1 bar to about 5 bar and an elevated temperature in the range of 400° C. to 650° C. to remove unreacted material adsorbed on the catalyst insofar as is practical, and then subsequently oxidizing the deposited carbon to $CO_2$ by addition of air or inert gas-diluted oxygen via line 170 to reactor 134 at a pressure in the range of about 1 bar to about 5 bar and an elevated temperature in the range of 400° C. to 650° C. Carbon dioxide and residual air or inert gas are vented from reactor 134 via line 175 during the regeneration period. In most cases, it is preferable to route the regeneration off-gas from reactor 134 via line 175 to the oxidation portion of the process (not illustrated) such that trace amounts of bromine, resulting from oxidation of HBr or alkyl bromides adsorbed on the catalyst, may be recovered and reused within the process.

The effluent which comprises hydrogen bromide, and higher molecular weight hydrocarbons, olefins or mixtures thereof is withdrawn from the second reactor 134 via line 135, cooled to a temperature in the range of about 0° C. to about 100° C. in exchanger 136, and combined with vapor effluent in line 112 from hydrocarbon stripper 147. The mixture is then passed to a scrubber 138 and contacted with a stripped, re-circulated water that is transported to scrubber 138 in line 164 by any suitable means, such as pump 143, and is cooled to a temperature in the range of about 0° C. to about 50° C. in heat exchanger 155. Any liquid hydrocarbon product condensed in scrubber 138 may be skimmed and withdrawn as stream 137 and added to liquid hydrocarbon product 154. Hydrogen bromide is dissolved in scrubber 138 in the aqueous solution which is removed from the scrubber 138 via line 144, and passed to hydrocarbon stripper 147 wherein residual hydrocarbons dissolved in the aqueous solution are stripped-out by contact with feed gas 111. The stripped aqueous phase effluent from hydrocarbon stripper 147 is cooled to a temperature in the range of about 0° C. to about 50° C. in heat exchanger 146 and then passed via line 165 to absorber 148 in which residual bromine is recovered from vent stream 167.

The residual vapor phase comprising olefins, higher molecular weight hydrocarbons or mixtures thereof is removed as effluent from the scrubber 138 and forwarded via line 139 to dehydrator 150 to remove substantially all water from the gas stream to prevent formation of liquid water, freezing, or formation of hydrates in product recovery unit 152. Water may be removed from dehydrator 150 via line 153. The dried gas stream containing the olefins, higher molecular weight hydrocarbons or mixtures thereof is further passed via line 151 to product recovery unit 152 to recover olefins, the higher molecular weight hydrocarbon fraction or mixtures thereof as a liquid product in line 154. Any conventional method of dehydration and liquids recovery such as solid-bed desiccant adsorption followed by, for example, refrigerated condensation, cryogenic expansion, or circulating absorption oil, or other solvents as used to process natural gas or refinery gas streams and recover olefinic hydrocarbons, as known to a skilled artisan, may be employed in the implementation of this invention. The residual vapor effluent from product recovery unit 152 is then split into a purge stream 157 that may be utilized as fuel for the process and a recycled residual vapor which is compressed via compressor 158. The recycled residual vapor discharged from compressor 158 is split into two fractions. A first fraction that is equal to at least 2.5 times the feed gas volume is transported via line 162, combined with the liquid bromine conveyed in line 125 and passed to heat exchanger 126 wherein the liquid bromine is vaporized and fed into first reactor 130. The second fraction which is drawn off line 162 via line 163 and is regulated by control valve 160, at a rate sufficient to dilute the alkyl bromide concentration to reactor 134 and absorb the heat of reaction such that reactor 134 is maintained at the selected operating temperature, preferably in the range of about 350° C. to about 450° C. in order to maximize conversion vs. selectivity and to minimize the rate of catalyst deactivation due to the deposition of carbon. Thus, the dilution provided by the recycled vapor effluent permits selectivity of bromination in the first reactor 130 to be controlled in addition to moderating the temperature in second reactor 134.

Oxygen, oxygen enriched air, or air 110 may be added to bromine stripper 114 by any suitable device or method (for example, via compressor 113) at a pressure in the range of about ambient to about 5 bar. This may be desirable where it is advantageous to strip residual bromine from water. The stripped water may exit stripper 114 via line 164, and can be divided into at least two portions. The first portion of the stripped water can be recycled via line 164, cooled in heat exchanger 155 to a temperature in the range of about 20° C. to about 50° C., and maintained at a pressure sufficient to enter scrubber 138 by any suitable means, such as pump 143. The portion of water that is recycled is selected such that the hydrobromic acid solution effluent removed from scrubber 138 via line 144 has a concentration in the range from about 10% to about 50% by weight hydrobromic acid, but more preferably in the range of about 30% to about 48% by weight to minimize the amount of water which must be vaporized in exchanger 141 and preheater 119 and to minimize the vapor pressure of HBr over the resulting acid. A second portion of water from stripper 114 is removed from line 164 and the process via line 156.

The dissolved hydrogen bromide that is contained in the aqueous solution effluent from scrubber 148 can be mixed with the oxygen, oxygen enriched air, or air leaving bromine stripper 114 in line 115. This mixture can be vaporized and preheated to a temperature in the range of about 120° C. to about 600° C. and most preferably in the range of about 150° C. to about 250° C., for example, by heat exchanger 141 and preheater 119. Once vaporized and preheated, the mixture may be added to third reactor 117 that contains a metal bromide salt or metal oxide. Any suitable bromide salt or combination of bromide salts may be used. The preferred metal of the bromide salt or metal oxide is Fe(III), Cu(II) or Zn(II) or mixtures thereof. The metal bromide salt in the oxidation reactor 117 may be utilized as a concentrated aqueous solution or preferably, the concentrated aqueous salt solution may be imbibed into a porous, low to medium surface area, acid resistant inert support such as a silica gel. More preferably, the oxide form of the metal in a range of 10 to 20% by weight is deposited on an inert support such as alumina with a specific surface area in the range of 5 to 200 m2/g. The oxidation reactor 117 operates at a pressure in the range of about ambient to about 5 bar and at a temperature in the range of about 100° C. to 600° C., but most preferably in the range of about 130° C. to 350° C.; therein, the metal bromide is oxidized by oxygen, yielding elemental bromine and metal hydroxide, metal oxide or metal oxy-bromide species or, metal oxides in the case of the supported metal bromide salt or metal oxide operated at higher temperatures and lower pressures at which water may primarily exist as a vapor. In either case, the hydrogen bromide reacts with the metal hydroxide, metal oxy-bromide or metal oxide species and is neutralized, restoring the metal bromide salt and yielding water. Thus, the overall reaction results in the net oxidation of hydrogen bromide produced in first reactor 130 and second reactor 134 to elemental bromine and steam, catalyzed by the metal bromide/metal hydroxide or metal oxide operating in a catalytic cycle. In the case of the metal bromide being Fe(III)Br$_3$ in an aqueous solution and operated in a pressure and temperature range in which water may exist as a liquid the reactions are believed to be:

$$Fe(+3a)+6Br(-a)+3H(+a)+3/2O_2(g)=3Br_2(g)+Fe(OH)3 \quad 1)$$

$$3HBr(g)+H_2O=3H(+a)+3Br(-a)+H_2O \quad 2)$$

$$3H(+a)+3Br(-a)+Fe(OH)3=Fe(+3a)+3Br(-a)+3H_2O \quad 3)$$

In the case of the metal bromide being Cu(II)Br$_2$ supported on an inert support and operated at higher temperature and lower pressure conditions at which water primarily exists as a vapor, the reactions are believed to be:

$$2Cu(II)Br2=2Cu(I)Br+Br2(g) \quad 1)$$

$$2Cu(I)Br+O_2(g)=Br2(g)+2Cu(II)O \quad 2)$$

$$2HBr(g)+Cu(II)O=Cu(II)Br2+H_2O(g) \quad 3)$$

The elemental bromine and water and any residual oxygen or nitrogen (if air or oxygen enriched air is utilized as the oxidant) leaving as vapor from the outlet of third reactor 117, are transported via line 127 and cooled in the second side of exchanger 141 and condenser 120 to a temperature in the range of about 0° C. to about 70° C. wherein the bromine and water are condensed and passed to three-phase separator 122. In three-phase separator 122, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus, a substantially dry bromine vapor may be easily obtained by condensing liquid bromine and water, decanting water by simple physical separation and subsequently re-vaporizing liquid bromine. It is important to operate at conditions that result in the near complete reaction of HBr so as to avoid significant residual HBr in the condensed liquid bromine and water, as HBr increases the miscibility of bromine in the aqueous phase, and at sufficiently high concentrations, results in a single ternary liquid phase.

Optionally, liquid bromine can be pumped from three-phase separator 122 via pump 124 to a pressure sufficient to mix with vapor stream 162. Thus, in these embodiments, the bromine can be recovered and recycled within the process, which can be beneficial. The residual air, oxygen enriched air or oxygen and any bromine vapor which is not condensed may exit three-phase separator 122 to bromine scrubber 148, wherein residual bromine can be recovered by dissolution into the hydrobromic acid solution stream conveyed to scrubber 148 via line 165. Water can be removed from the three-phase separator 122 via line 129 and passed to stripper 114.

Thus, in certain embodiments of the processes of the present invention, the metal bromide/metal hydroxide, metal oxy-bromide or metal oxide operates in a catalytic cycle allowing bromine to be recycled for reuse within the process. The metal bromide is readily oxidized by oxygen, oxygen enriched air or air either in the aqueous phase or the vapor phase at temperatures in the range of about 100° C. to about 600° C. and most preferably in the range of about 120° C. to about 350° C. to yield elemental bromine vapor and metal hydroxide, metal oxy-bromide or metal oxide. Operation at temperatures below about 180° C. is advantageous, thereby allowing the use of low-cost corrosion-resistant fluoropolymer-lined equipment. Hydrogen bromide is neutralized by reaction with the metal hydroxide or metal oxide yielding steam and the metal bromide.

The elemental bromine vapor and steam are condensed and easily separated in the liquid phase by simple physical separation, yielding substantially dry bromine. The absence of significant water allows selective bromination of alkanes, without production of $CO_2$ and the subsequent efficient and selective reactions of alkyl bromides to primarily higher molecular weight hydrocarbons which contain substantial branched alkanes, substituted aromatics, or mixtures thereof. Byproduct hydrogen bromide vapor from the bromination reaction and subsequent reaction in reactor 134 are readily dissolved into an aqueous phase and neutralized by the metal hydroxide or metal oxide species resulting from oxidation of the metal bromide.

Figure 4A:
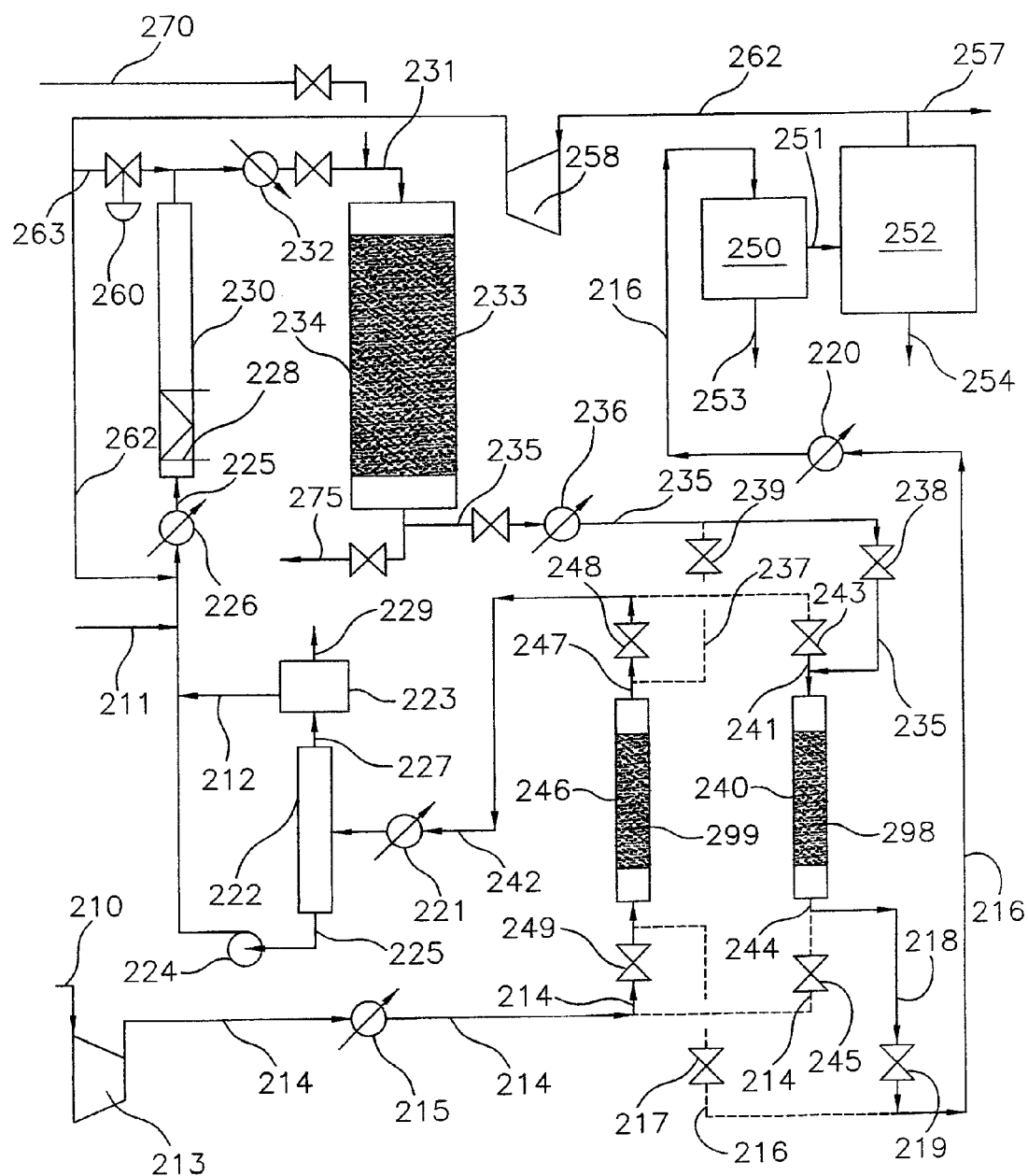
FIG. 4A is schematic view of another embodiment of the processes of the present invention.

In accordance with another embodiment of the processes of the present invention illustrated in FIG. 4A, the alkyl bromination and alkyl bromide conversion stages are operated in a substantially similar manner to those corresponding stages described with respect to FIGS. 2 and 3 above. More particularly, a gas stream containing lower molecular weight alkanes comprised of mixture of a feed gas and a recycled gas stream at a pressure in the range of about 1 bar to about 30 bar, is transported or conveyed via line, pipe or conduits 262 and 211, respectively, and mixed with dry bromine liquid in line 225. The resultant mixture is transported via pump 224 and passed to heat exchanger 226 wherein the liquid bromine is vaporized. The mixture of lower molecular weight alkanes and dry bromine vapor is fed to reactor 230. Preferably, the molar ratio of lower molecular weight alkanes to dry bromine vapor in the mixture introduced into reactor 230 is in excess of about 2.5:1, more preferably in excess of about 4:1, and most preferably in excess of about 7:1. Reactor 230 has an inlet pre-heater zone 228 which heats the mixture to a reaction initiation temperature in the range of 250° C. to 400° C.

In first reactor 230, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. As will be evident to a skilled artisan with the benefit of this disclosure, the bromination reaction in first reactor 30 may be an exothermic reaction or a catalytic reaction. Non-limiting examples of suitable catalysts that may be used in first reactor 30 include platinum, palladium, or supported non-stiochiometric metal oxy-halides, such as FeO$_x$Br$_y$, or FeO$_x$Cl$_y$, or supported metal oxy-halides, such as TaOF$_3$, NbOF$_3$, ZrOF$_2$, SbOF$_3$ as described in Olah, et al, J. Am. Chem. Soc. 1985, 107, 7097-7105. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

$$CH_4(g)+Br_2(g) \rightarrow CH_3Br(g)+HBr(g)$$

Due to the free-radical mechanism of the gas-phase bromination reaction, di-bromomethane and some tri-bromomethane and other alkyl bromides are also formed. However, this reaction in accordance with the processes of the present invention often occurs with a relatively high degree of selectivity to methyl bromide due to the alkane to bromine ratio employed in first reactor 230. For example, in the case of the bromination of methane, a methane to bromine ratio of about 6:1 is believed to increase the selectivity to mono-halogenated methyl bromide to average approximately 80%, depending on reaction conditions, such as residence time, temperature, and turbulent mixing. At these conditions, some dibromomethane and only extremely small amounts of tri-bromomethane approaching the detectable limits also may be formed in the bromination reaction. If a lower methane to bromine ratio of approximately 2.6 to 1 is utilized, selectivity to the mono-halogenated methyl bromide may fall to the range of approximately 65 to 75% depending on other reaction conditions. At a methane to bromine ratio significantly less than about 2.5 to 1, unacceptable low selectivities to methyl bromide occurs, and, moreover, significant formation of undesirable di-bromomethane, tri-bromomethane, and carbon soot may be observed. The residence time of the reactants in first reactor 230 necessary to achieve such selectivity to mono-halogenated methyl bromide is relatively short and may be as little as 1-5 seconds under adiabatic reaction conditions. Higher alkanes, such as ethane, propane and butane, also may be brominated, resulting in mono and multiple brominated species such as ethyl bromides, propyl bromides and butyl bromides. Further, in some embodiments, the dry bromine vapor that is fed into first reactor 230 may be substantially water-free. Applicant has discovered that, at least in some instances, this may be preferred because it appears that elimination of substantially all water vapor from the bromination step in first reactor 230 substantially eliminates the formation of unwanted carbon dioxide. This may increase the selectivity of alkane bromination to alkyl bromides, thus possibly eliminating the large amount of waste heat generated in the formation of carbon dioxide from alkanes.

The effluent that contains alkyl bromides and hydrogen bromide is withdrawn from the first reactor 230 via line 231. In some embodiments, the effluent may be partially cooled in heat exchanger 232 before flowing to a second reactor 234. The temperature to which the effluent is partially cooled in heat exchanger 232 is in the range of about 150° C. to about 390° C. when it is desired to convert the alkyl bromides to higher molecular weight hydrocarbons in second reactor 234, or to range of about 150° C. to about 450° C. when it is desired to convert the alkyl bromides to olefins a second reactor 234. Second reactor 234 is thought to dehydrohalogenate and oligomerize the resultant alkyl moieties so as to form products that comprise olefins, higher molecular weight hydrocarbons or mixtures thereof. The catalyst used in second reactor 234 and the temperature at which the reactor 234 is operated can be selected to achieve the desired hydrocarbon product as described above with respect to reactor 34. In certain embodiments, second reactor 234 may comprise a fixed bed 233 of the catalyst. A fluidized-bed of synthesis catalyst may also be used in certain circumstances, particularly in larger applications and may have certain advantages, such as constant removal of coke and a steady selectivity to product composition.

The catalyst may be periodically regenerated in situ, by isolating reactor 234 from the normal process flow, purging with an inert gas via line 270 at a pressure in the range of about 1 bar to about 5 bar and an elevated temperature in the range of about 400° C. to about 650° C. to remove unreacted material adsorbed on the catalyst insofar as is practical, and then subsequently oxidizing the deposited carbon to $CO_2$ by addition of air or inert gas-diluted oxygen via line 270 to reactor 234 at a pressure in the range of about 1 bar to about 5 bar and an elevated temperature in the range of about 400° C. to about 650° C. Carbon dioxide and residual air or inert gas are vented from reactor 234 via line 275 during the regeneration period.

In most cases it is preferable to route the regeneration off-gas from reactor 234 via line 275 to the oxidation portion of the process (not illustrated) such that trace amounts of bromine, resulting from oxidation of HBr or alkyl bromides adsorbed on the catalyst, may be recovered and reused within the process.

The effluent which comprises hydrogen bromide and higher molecular weight hydrocarbons, olefins, or mixtures thereof is withdrawn from the second reactor 234 via line 235 and cooled to a temperature in the range of about 100° C. to about 600° C. in exchanger 236. As illustrated in FIG. 4A, the cooled effluent is transported via lines 235 and 241 with valve 238 in the opened position and valves 239 and 243 in the closed position and introduced into a vessel or reactor 240 containing a bed 298 of a solid phase metal oxide. The metal of the metal oxide is selected form magnesium (Mg), calcium (Ca), vanadium (V), chromium (Cr), manganese (Mn), iron (Fe), cobalt (Co), nickel (Ni), copper (Cu), zinc (Zn), or tin (Sn). The metal is selected for the impact of its physical and thermodynamic properties relative to the desired temperature of operation, and also for potential environmental and health impacts and cost. Preferably, magnesium, nickel, copper, iron, or mixtures thereof are employed as the metal(s), with magnesium, nickel or mixtures thereof being the most preferred. These metals have the property of not only forming oxides but bromide salts as well, with the reactions being reversible in a temperature range of less than about 500° C. The solid metal oxide is preferably immobilized on a suitable attrition-resistant support, for example a synthetic amorphous silica, such as Davicat Grade 57, manufactured by Davison Catalysts of Columbia, Md. Or more preferably, on a silica or alumina support with a specific surface area in the range of about 5 to 400 m2/g. In reactor 240, hydrobromic acid is reacted with the metal oxide at temperatures below about 600° C. and preferably between about 100° C. to about 550° C. in accordance with the following general reaction wherein M represents the metal:

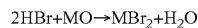

$$2HBr + MO \rightarrow MBr_2 + H_2O$$

The steam resulting from this reaction is transported together with the high molecular hydrocarbons in line 244, 218 and 216 via opened valve 219 to heat exchanger 220 wherein the mixture is cooled to a temperature in the range of about 0° C. to about 70° C. This cooled mixture is forwarded to dehydrator 250 to remove substantially all water from the gas stream. The water is then removed from the dehydrator 250 via line 253. The dried gas stream containing olefins, higher molecular weight hydrocarbons or mixtures thereof is further passed via line 251 to product recovery unit 252 to recover olefins, the $C_{5+}$ fraction or mixtures thereof as a liquid product in line 254. Any conventional method of dehydration and liquids recovery such as solid-bed desiccant adsorption followed by, for example, refrigerated condensation, cryogenic expansion, or circulating absorption oil or other solvent, as used to process natural gas or refinery gas streams and recover olefinic hydrocarbons, as known to a skilled artisan, may be employed in the implementation of this invention. The residual vapor effluent from product recovery unit 252 is then split into a purge stream 257 that may be utilized as fuel for the process and a recycled residual vapor which is compressed via compressor 258. The recycled residual vapor discharged from compressor 258 is split into two fractions. A first fraction that is equal to at least 1.5 times the feed gas volume is transported via line 262, combined with the liquid bromine and feed gas conveyed in line 225 and passed to heat exchanger 226 wherein the liquid bromine is vaporized and fed into first reactor 230 in a manner as described above. The second fraction which is drawn off line 262 via line 263 and is regulated by control valve 260, at a rate sufficient to dilute the alkyl bromide concentration to reactor 234 and absorb the heat of reaction such that reactor 234 is maintained at the selected operating temperature, preferably in the range of about 300° C. to about 450° C. in order to maximize conversion vs. selectivity and to minimize the rate of catalyst deactivation due to the deposition of carbon. Thus, the dilution provided by the recycled vapor effluent permits selectivity of bromination in the first reactor 230 to be controlled in addition to moderating the temperature in second reactor 234.

Oxygen, oxygen enriched air or air 210 is delivered via blower or compressor 213 at a pressure in the range of about ambient to about 10 bar to bromine via line 214, line 215 and valve 249 through heat exchanger 215, wherein oxygen, oxygen enriched air or air is preheated to a temperature in the range of about 30° C. to about 600° C., more preferably 100° C. to about 500° C., to a second vessel or reactor 246 containing a bed 299 of a solid phase metal bromide. Oxygen reacts with the metal bromide in accordance with the following general reaction wherein M represents the metal:

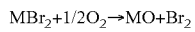

In this manner, a dry, substantially HBr free bromine vapor is produced thereby eliminating the need for subsequent separation of water or hydrogen bromide from the liquid bromine. Reactor 246 is operated below 600° C., and more preferably between about 300° C. to about 500° C. The resultant bromine vapor is transported from reactor 246 via line 247, valve 248 and line 242 to heat exchanger or condenser 221 where the bromine is condensed into a liquid. The liquid bromine is transported via line 242 to separator 222 wherein liquid bromine is removed via line 225 and transported via line 225 to heat exchanger 226 and first reactor 230 by any suitable means, such as by pump 224. The residual air or unreacted oxygen is transported from separator 222 via line 227 to a bromine scrubbing unit 223, such as venturi scrubbing system containing a suitable solvent, or suitable solid adsorbent medium, as selected by a skilled artisan, wherein the remaining bromine is captured. The captured bromine is desorbed from the scrubbing solvent or adsorbent by heating or other suitable means and the thus recovered bromine transported via line 212 to line 225. The scrubbed air or oxygen is vented via line 229. In this manner, nitrogen and any other substantially non-reactive components are removed from the system of the present invention and thereby not permitted to enter the hydrocarbon-containing portion of the process; also loss of bromine to the surrounding environment is avoided.

One advantage of removing the HBr by chemical reaction in accordance with this embodiment, rather than by simple physical solubility, is the substantially complete scavenging of the HBr to low levels at higher process temperatures. Another distinct advantage is the elimination of water from the bromine removed thereby eliminating the need for separation of bromine and water phases and for stripping of residual bromine from the water phase.

Reactors 240 and 246 may be operated in a cyclic fashion. As illustrated in FIG. 4A, valves 238 and 219 are operated in the open mode to permit hydrobromic acid to be removed from the effluent that is withdrawn from the second reactor 240, while valves 248 and 249 are operated in the open mode to permit air, oxygen enriched air or oxygen to flow through reactor 246 to oxidize the solid metal bromide contained therein. Once significant conversion of the metal oxide and metal bromide in reactors 240 and 246, respectively, has occurred, these valves are closed. At this point, bed 299 in reactor 246 is a bed of substantially solid metal oxide, while bed 298 in reactor 240 is substantially solid metal bromide.

As will be evident to the skilled artisan, in between the steps of cycling flows between reactors 240 and 246, it is preferred to first purge residual hydrocarbons that remain in reactor 240 and also purge residual bromine that remains in reactor 246 with a source of inert gas to inhibit the loss of hydrocarbons and bromine to the subsequent step in the cycle. By purging between bed in between steps of the cycle the possible loss and/or bromination of higher molecular-weight product hydrocarbons is inhibited.

Figure 5A:
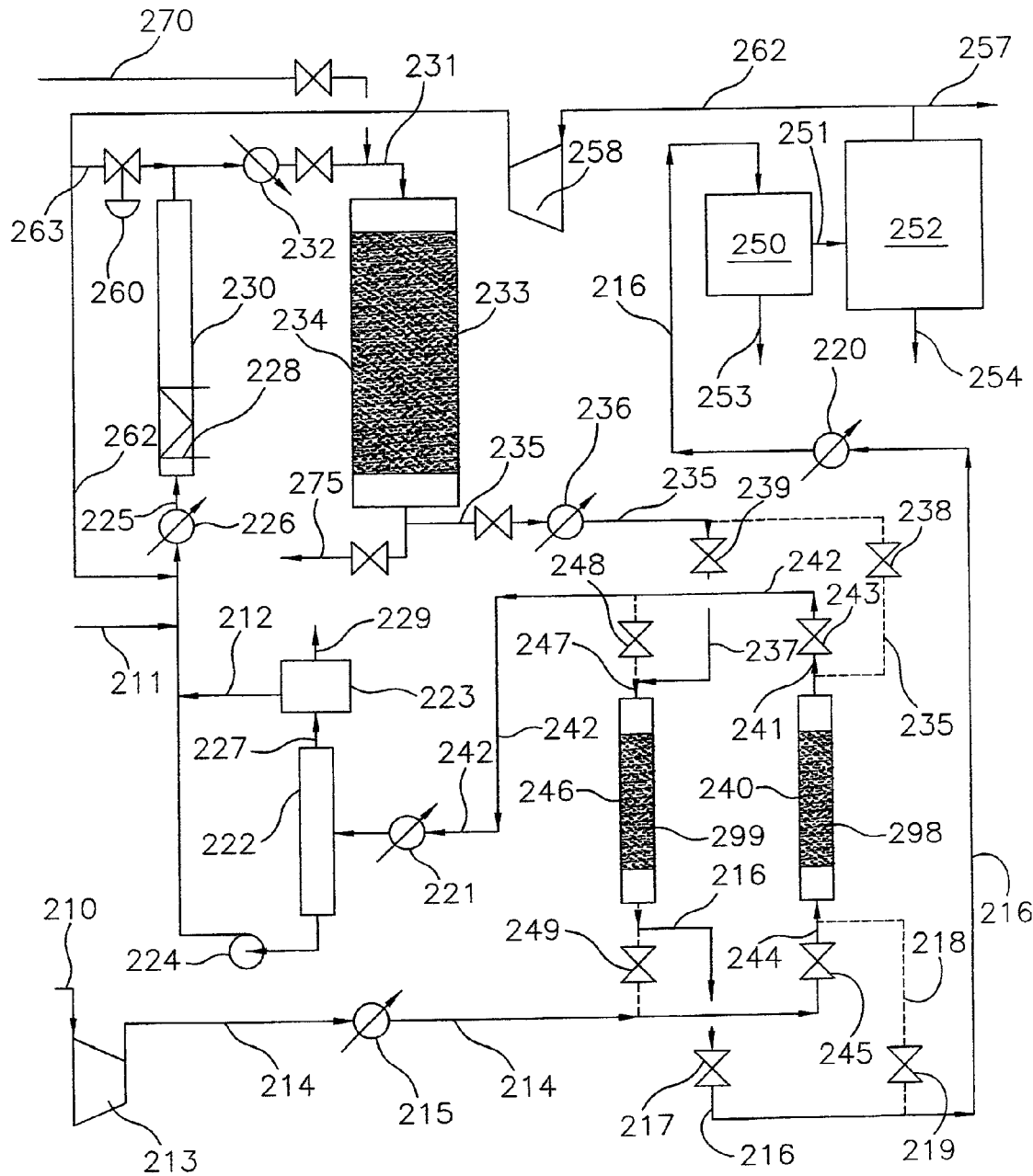
FIG. 5A is a schematic view of the embodiment of the processes of the present invention illustrated in FIG. 4A with the flow through the metal oxide beds being reversed.

As illustrated in FIG. 5A, valves 245 and 243 are then subsequently opened to permit oxygen, oxygen enriched air or air to flow through reactor 240 to oxidize the solid metal bromide contained therein, while valves 239 and 217 are opened to permit effluent which comprises higher molecular weight hydrocarbons and hydrogen bromide that is withdrawn from the second reactor 234 to be introduced into reactor 246 via line 237. The reactors are operated in this manner until significant conversion of the metal oxide and metal bromide in reactors 246 and 240, respectively, has occurred and then the reactors are cycled back to the flow schematic illustrated in FIG. 4A by opening and closing valves as previously discussed.

As will also be further evident to the skilled artisan, the amount of active metal oxide/metal bromide such as MgO/MgBr2 deposited on the solid inert support (which may be expressed as weight percent loading of the metal, as atomic metal, on the inert solid support) will have an effect on the temperature changes that will occur across reactors 240 and 246, because of the ratio of the heat of reaction to the heat capacity of the solid inert support occurring in solid beds 298 and 299. Increasing the metal loading relative to the amount of inert support is desirable as it decreases the sizes of the vessels required for a specified HBr-removal capacity, however the heat rise which occurs will be also be greater due to the relatively larger ratio of the heats of reaction to the heat capacity of the inert support. The resultant temperature rise may be excessive and could result in oxidation of thermal cracking of the higher molecular-weight hydrocarbon products or volatility of the metal bromide. Thus the acceptable temperature rise may alternatively limit the cycle time or effectively limit the useful HBr removal capacity of the solid beds 298 and 299. The use of effluent gas recycle through an external heat exchanger by means of a blower or compressor (not shown) may be considered by the skilled artisan as a means to limit the temperature rise across reactors 240 and 246 and also to effect cooling of the solid beds 298 and 299 in between cycling of reactors 240 and 246. Although two reactors 240 and 246 are shown to illustrate the concept of the invention, it should be apparent to the skilled artisan that more than two reactors, i.e. three (or more) could be utilized in the implementation of the invention in certain embodiments, as a practical means to allow continuous process operation and also allow purging and cool-down between switching of reactors from HBr-removal to Br2-generating steps.

Figure 4B:
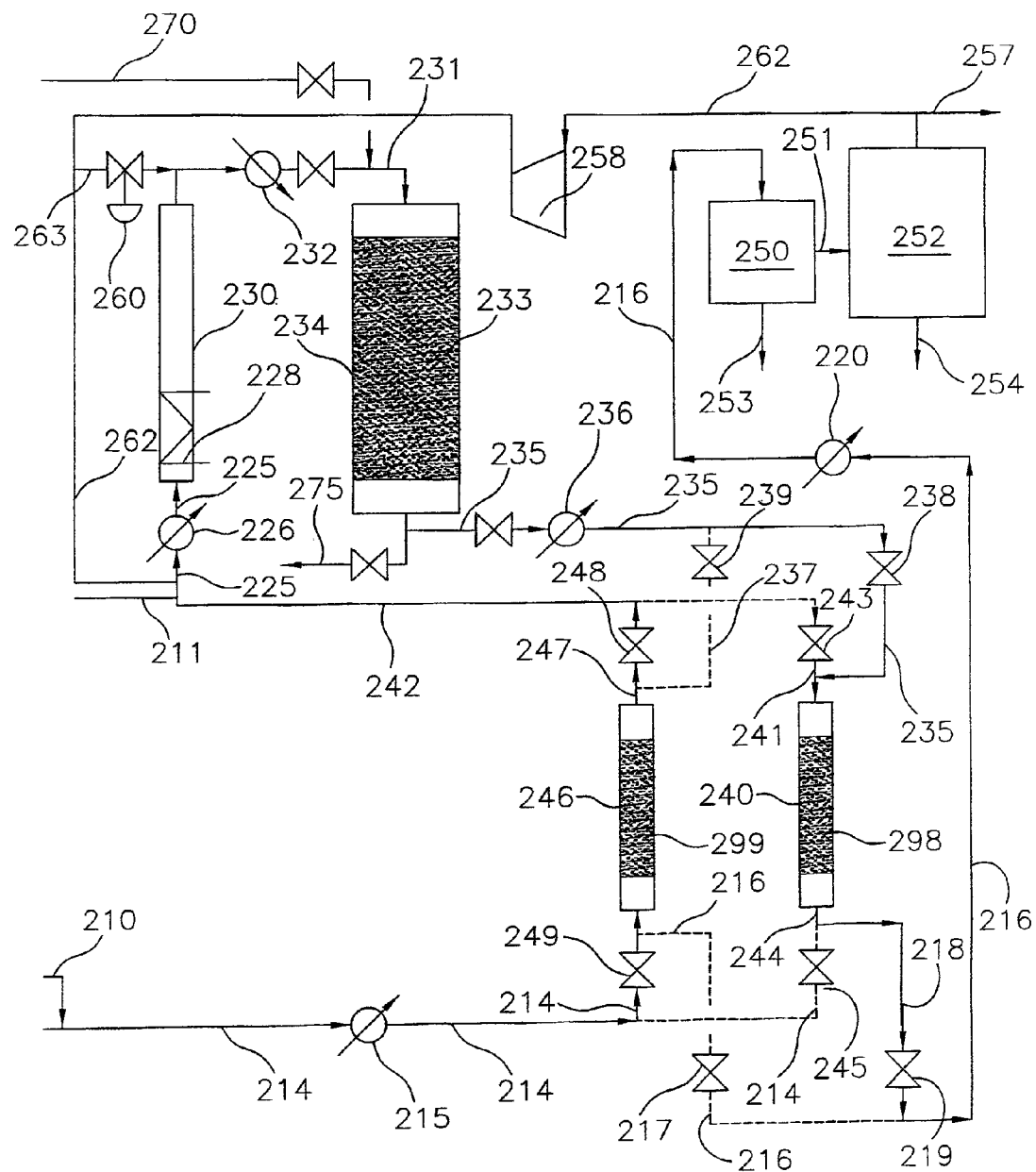
FIG. 4B is a schematic view of the embodiment of the processes of the present invention illustrated in FIG. 4A depicting an alternative processing scheme which may be employed when oxygen is used in lieu of air in the oxidation stage.
Figure 5B:
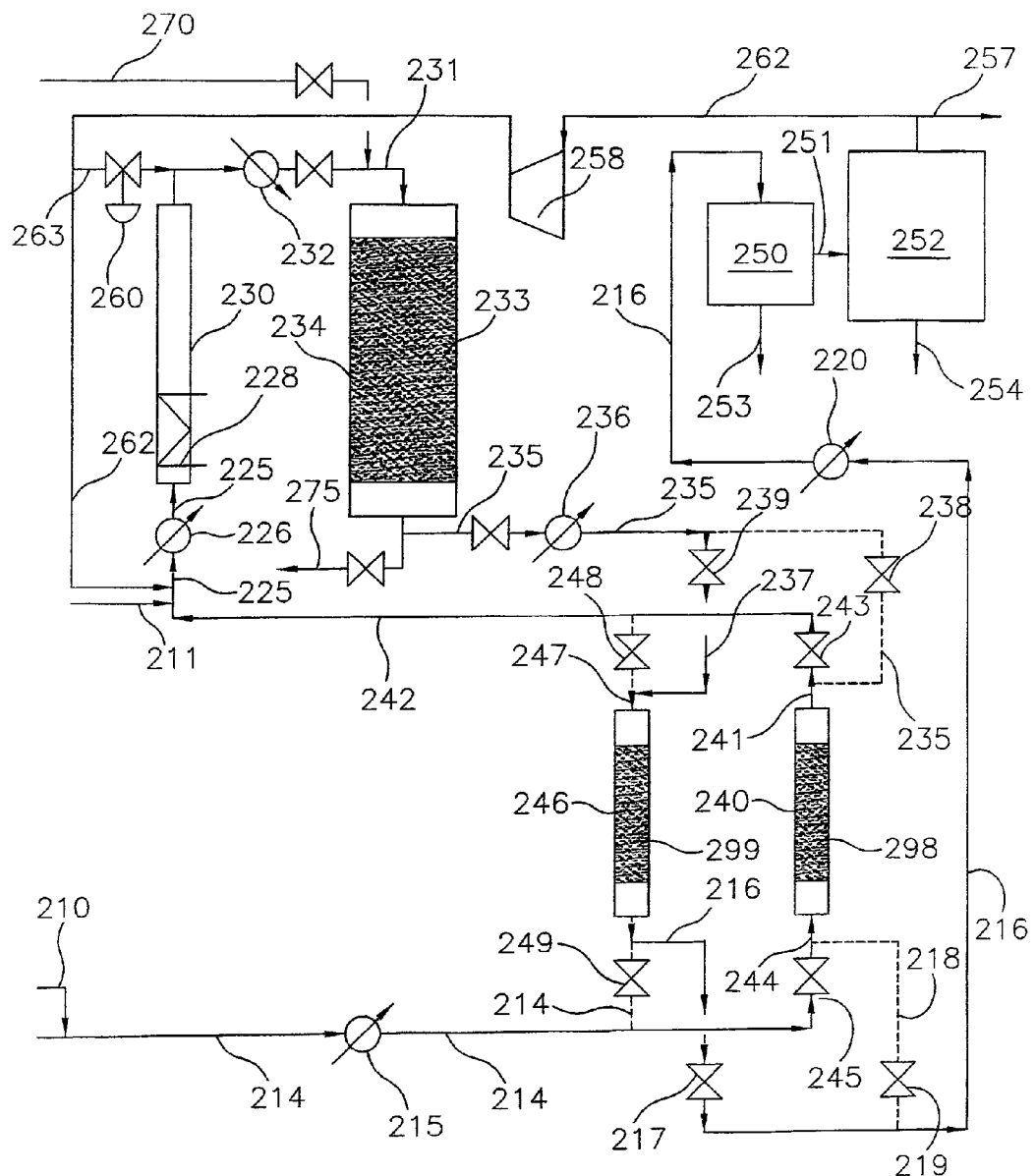
FIG. 5B is a schematic view of the embodiment of the processes of the present invention illustrated in FIG. 5A depicting an alternative processing scheme which may be employed when oxygen is used in lieu of air in the oxidation stage.

When oxygen is utilized as the oxidizing gas transported in via line 210 to the reactor being used to oxidize the solid metal bromide contained therein, the embodiment of the processes of the present invention illustrated in FIGS. 4A and 5A may be modified such that the bromine vapor produced from either reactor 246 (FIG. 4B) or 240 (FIG. 5B) is transported via lines 242 and 225 directly to first reactor 230. Since oxygen is reactive, and reactors 246 and 240 can be operated with a controlled, limited feed of oxygen to avoid the substantial presence of oxygen in the effluent Br2 vapor, hence the need to condense the bromine vapor to a liquid to separate it from unreactive components, such as nitrogen, is obviated. Compressor 213 is not illustrated in FIGS. 4B and 5B as substantially all commercial sources of oxygen, such as a commercial air separation unit (ASU), will provide oxygen to line 210 at the required pressure. If not, a compressor 213 could be utilized to achieve such pressure as will be evident to a skilled artisan.

In the embodiment of the present invention illustrated in FIG. 6A, the beds of solid metal oxide particles and solid metal bromide particles contained in reactors 240 and 246, respectively, are fluidized and are connected in the manner described below to provide for continuous operation of the beds without the need to provide for equipment, such as valves, to change flow direction to and from each reactor. In accordance with this embodiment, the effluent which comprises higher molecular weight hydrocarbons and hydrobromic acid is withdrawn from the second reactor 234 via line 235, cooled to a temperature in the range of about 100° C. to about 500° C. in exchanger 236, and introduced into the bottom of reactor 240 which contains a bed 298 of solid metal oxide particles. The flow of this introduced fluid induces the particles in bed 298 to move upwardly within reactor 240 as the hydrogen bromide is reacted with the metal oxide in the manner as described above with respect to FIG. 4A. At or near the top of the bed 298, the particles which contain substantially solid metal bromide on the attrition-resistant support due to the substantially complete reaction of the hydrogen bromide with the solid metal oxide in reactor 240 are withdrawn via a weir or cyclone or other conventional means of solid/gas separation, flow by gravity down line 259 and are introduced at or near the bottom of the bed 299 of solid metal bromide particles in reactor 246. In the embodiment illustrated in FIG. 6A, oxygen, oxygen enriched air or air 210 is delivered via blower or compressor 213 at a pressure in the range of about ambient to about 10 bar, transported via line 214 through heat exchanger 215, wherein the oxygen, oxygen enriched air or air is preheated to a temperature in the range of about 30° C. to about 600° C., more preferably 100° C. to about 500° C., and introduced into second vessel or reactor 246 below bed 299 of a solid phase metal bromide. Oxygen reacts with the metal bromide in the manner described above with respect to FIG. 4A to produce a dry, substantially HBr free bromine vapor. The flow of this introduced gas induces the particles in bed 299 to flow upwardly within reactor 246 as oxygen is reacted with the metal bromide. At or near the top of the bed 298, the particles which contain a substantial amount of solid metal oxide on the attrition-resistant support due to the substantially complete reaction of the oxygen with the solid metal bromide in reactor 246 are withdrawn via a weir or cyclone or other conventional means of solid/gas separation, flow by gravity down line 264 and are introduced at or near the bottom of the bed 298 of solid metal oxide particles in reactor 240. In this manner, reactors 240 and 246 may be operated continuously without changing the parameters of operation.

As known to the skilled artisan, it may be advantageous to utilize heat exchangers positioned within the moving beds of solids 298 and 299 to remove heat in the case of exothermic reactions or to add heat in the case of endothermic reactions depending on the choice of metal oxide or metal bromide selected. In the case of using the preferred MgO/MgBr2, both reactions are exothermic.

Figure 6A:
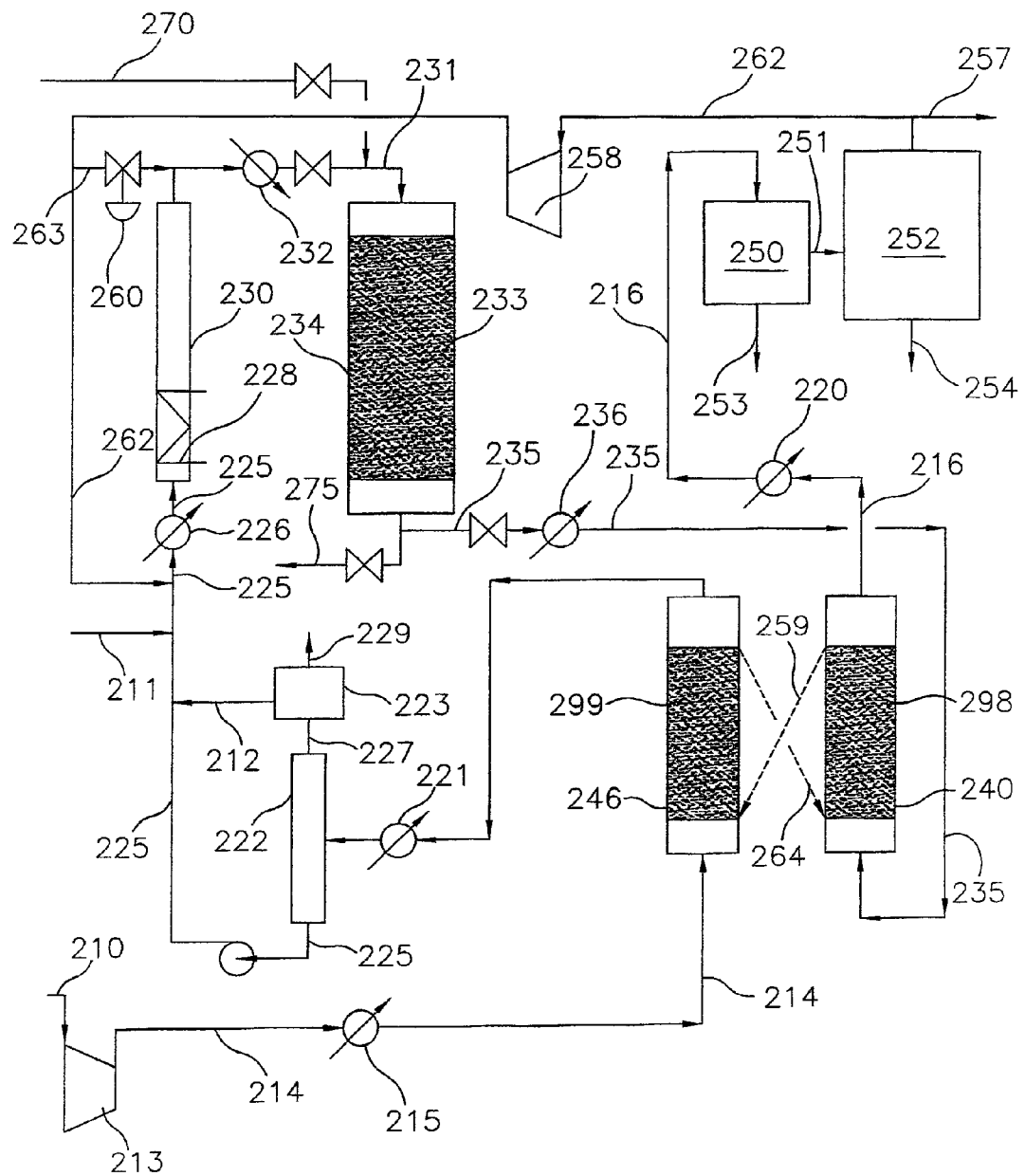
FIG. 6A is a schematic view of another embodiment of the processes of the present invention.
Figure 6:
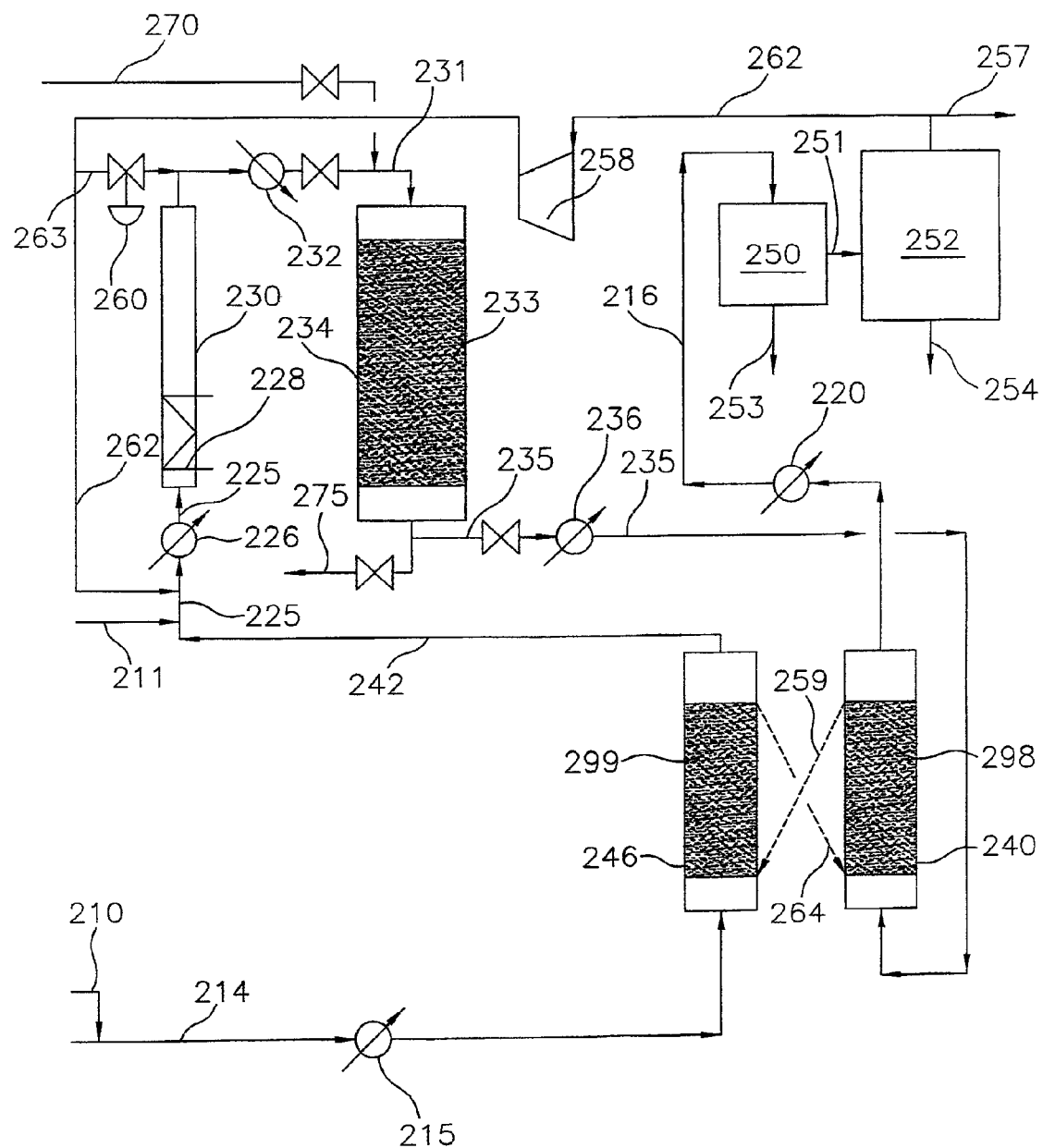
FIG. 6B is a schematic view of the embodiment of the processes of the present invention illustrated in FIG. 6A depicting an alternative processing scheme which may be employed when oxygen is used in lieu of air in the oxidation stage.

In the embodiment illustrated in FIG. 6B, oxygen is utilized as the oxidizing gas and is transported in via line 210 to reactor 246. Accordingly, the embodiment of the processes of the present invention illustrated in FIG. 6A is modified such that the bromine vapor produced from reactor 246 is transported via lines 242 and 225 directly to first reactor 230. Since oxygen is reactive, and reactor 246 can be operated with a controlled, limited feed of oxygen to avoid the presence of substantial oxygen in the effluent bromine vapor, hence the need to condense the bromine vapor to a liquid to separate it from unreactive components, such as nitrogen, is obviated. Compressor 213 is not illustrated in FIG. 6B as substantially all commercial sources of oxygen, such as a commercial air separator unit, will provide oxygen to line 210 at the required pressure. If not, a compressor 213 could be utilized to achieve such pressure as will be evident to a skilled artisan.

Figure 7:
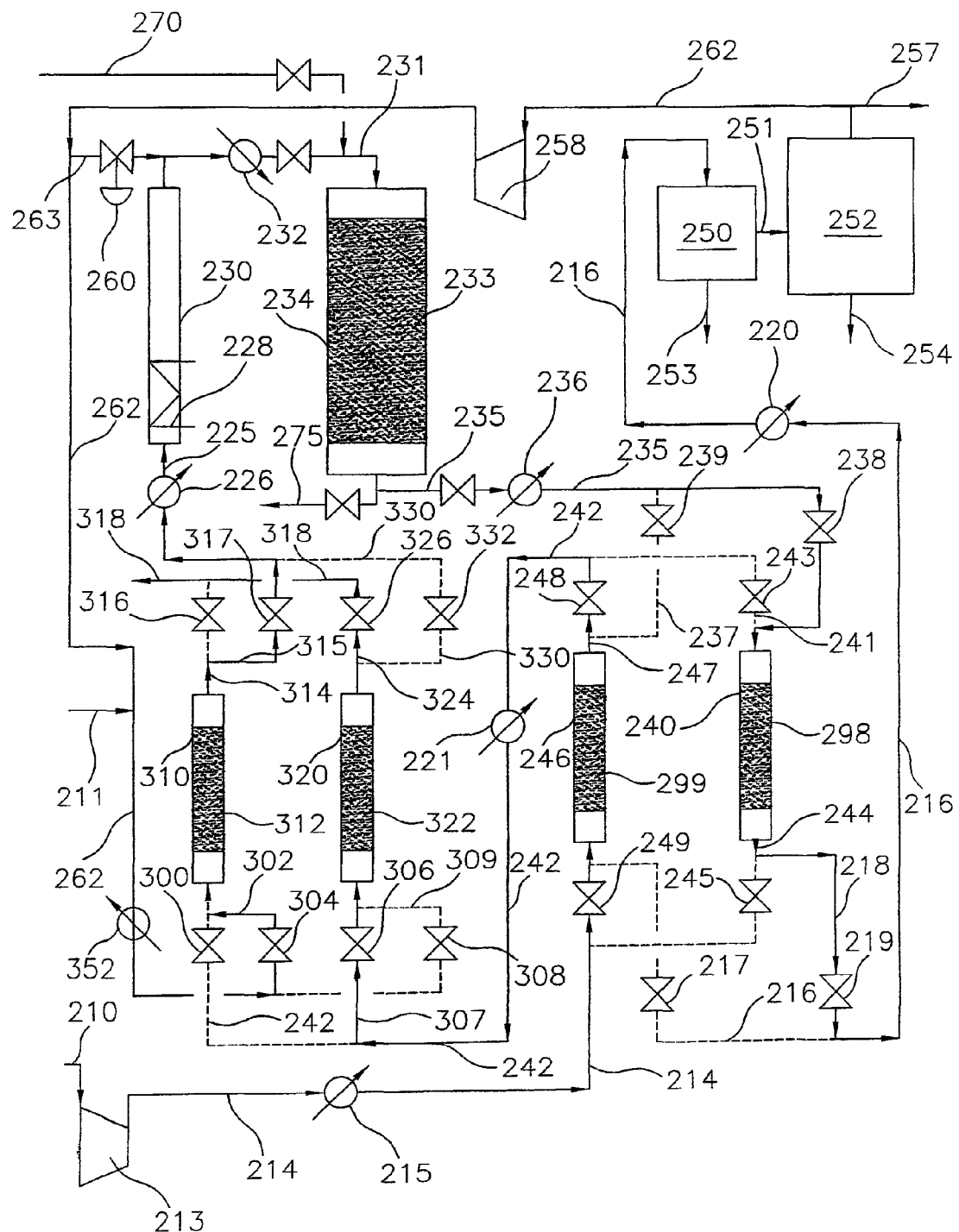
FIG. 7 is a schematic view of another embodiment of the processes of the present invention.

In accordance with another embodiment of the processes of the present invention that is illustrated in FIG. 7, the alkyl bromination and alkyl bromide conversion stages are operated in a substantially similar manner to those corresponding stages described in detail with respect to FIG. 4A except as discussed below. In this embodiment, however it is important to operate reactor 246 with a controlled limited amount of oxidizing gas so as to prevent the presence of substantial unreacted oxygen in the effluent from reactor 246. Residual nitrogen and bromine vapor emanating from reactor 246 is transported via line 247, valve 248 and line 242 and valve 300 to heat exchanger or condenser 221 wherein the bromine-containing gas is cooled to a temperature in the range of about 30° C. to about 300° C. The bromine-containing vapor is then transported via line 242 to vessel or reactor 320 containing a bed 322 of a solid phase metal bromide in a reduced valence state. The metal of the metal bromide in a reduced valence state is selected from copper (Cu), iron (Fe), or molybdenum (Mo). The metal is selected for the impact of its physical and thermodynamic properties relative to the desired temperature of operation, and also for potential environmental and health impacts and cost. Preferably, copper or iron are employed as the metal, with iron being the most preferred. The solid metal bromide is preferably immobilized on a suitable attrition-resistant support, for example a synthetic amorphous silica, such as Davicat Grade 57, manufactured by Davison Catalysts of Columbia, Md. More preferably the metal is deposited in oxide form in a range of about 10 to 20 wt % on an alumina support with a specific surface area in the range of about 5 to 400 m2/g. In reactor 320, bromine vapor is reacted with the solid phase metal bromide, preferably retained on a suitable attrition-resistant support at temperatures below about 300° C. and preferably between about 30° C. to about 200° C. depending on the metal bromide selected, in accordance with the following general reaction wherein $M^2$ represents the metal:

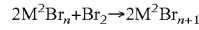

$$2M^2Br_n+Br_2\rightarrow 2M^2Br_{n+1}$$

In this manner, bromine is stored as a second metal bromide, i.e. $2M^2Br_{n+1}$, in reactor 320 while the resultant vapor containing residual air or oxygen is vented from reactor 320 via line 324, valve 326 and line 318.

The gas stream containing lower molecular weight alkanes, comprised of mixture of a feed gas (line 211) and a recycled gas stream, is transported or conveyed via line 262, heat exchanger 352, wherein the gas stream is preheated to a temperature in the range of about 150° C. to about 600° C., valve 304 and line 302 to a second vessel or reactor 310 containing a bed 312 of a solid phase metal bromide in an oxidized valence state. The metal of the metal bromide in an oxidized valence state is selected from copper (Cu), iron (Fe), or molybdenum (Mo). The metal is selected for the impact of its physical and thermodynamic properties relative to the desired temperature of operation, and also for potential environmental and health impacts and cost. Preferably, copper or iron are employed as the metal, with iron being the most preferred. The solid metal bromide in an oxidized state is preferably immobilized on a suitable attrition-resistant support, for example a synthetic amorphous silica such as Davicat Grade 57, manufactured by Davison Catalysts of Columbia, Md. More preferably the metal is deposited in an oxide state in a range of 10 to 20 wt % supported on an alumina support with a specific surface area in the range of about 5 to 200 m2/g. The temperature of the gas stream is from about 150° C. to about 600° C., and preferably from about 150° C. to about 300° C. In second reactor 310, the temperature of the gas stream thermally decomposes the solid phase metal bromide in an oxidized valence state to yield elemental bromine vapor and a solid metal bromide in a reduced state in accordance with the following general reaction wherein $M^2$ represents the metal:

$$2M^2Br_{n+1} \rightarrow 2M^2Br_n + Br_2$$

In addition, at temperatures of about 200° C. and higher the lower molecular weight alkanes contained in the gas stream may react over the heated bed of the solid metal bromide in an oxidized state to produce gaseous alkyl bromides, hydrobromic acid vapors and a solid metal bromide in a reduced state in accordance with the following general reaction wherein $M^2$ represents the metal:

$$CH_4(g) + 2M^2Br_{n+1} \rightarrow CH_3Br(g) + HBr(g) + M^2Br_n$$

By controlling the temperature of the gas stream and therefore the temperature of the bed 312 of the solid phase metal bromide in an oxidized valence state, the degree to which bromine is liberated and the lower molecular weight alkanes are brominated in second vessel or reactor 310 may be controlled. While the exact mechanism by which the lower molecular weight alkanes react over the heated bed of the solid metal bromide in an oxidized state to produce gaseous alkyl bromides is not completely understood, it is applicants' belief that bromination may occur on the solid surface of the support for the metal bromide thereby allowing the reaction to proceed at lower temperatures, for example about 200° C. to about 300° C. thereby inhibiting free-radical gas phase bromination and minimizing the production of multi-brominated alkanes.

The resultant bromine vapor, alkyl bromide and hydrobromic acid are transported with the gas stream containing lower molecular weight alkanes via lines 314, 315, valve 317, line 330, heat exchanger 226 prior to being introduced into alkyl bromination reactor 230. If significant amounts of the lower molecular weight gaseous alkanes are brominated in second vessel or reactor 310, heat exchanger 226 and bromination reactor 230 may be eliminated from the process schematic and the gas stream may be transported directly to second reactor 234 via exchanger 232. This may be accomplished by passing the gas stream through heat exchanger 226 and reactor 230 without heating the gas stream or both of these components may be eliminated or bypassed as will be evident to a skilled artisan.

Figure 8:
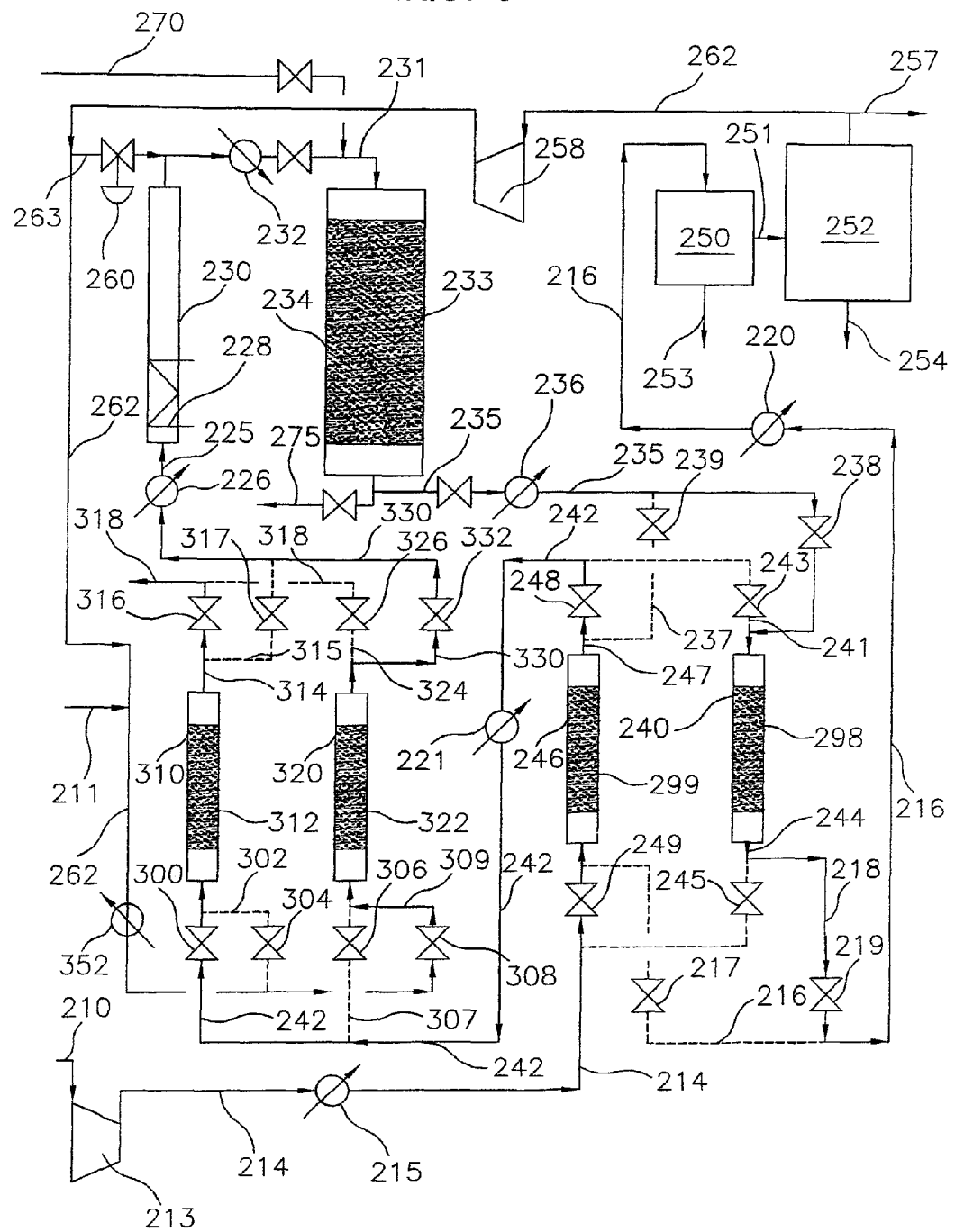
FIG. 8 is a schematic view of the embodiment of the processes of the present invention illustrated in FIG. 7 with the flow through the metal oxide beds being reversed.

Reactors 310 and 320 may be operated in a cyclic fashion. As illustrated in FIG. 7, valve 304 is operated in the open mode to permit the gas stream containing lower molecular weight alkanes to be transported to the second reactor 310, while valve 317 is operated in the open mode to permit this gas stream with bromine vapor, alkyl bromide and hydrobromic acid that is generated in reactor 310 to be transported to alkyl bromination reactor 230 or to reactor 234 via heat exchanger 232 if significant amounts of lower molecular weight gaseous alkanes are brominated in second reactor 310 in a manner as noted above. Likewise, valve 306 is operated in the open mode to permit bromine vapor from reactor 246 to be transported to reactor 320 via line 307, while valve 326 is operated in the open mode to permit residual air or oxygen to be vented from reactor 320 via line 307. Once significant conversion of the reduced metal bromide and oxidized metal bromide in reactors 320 and 310, respectively, to the corresponding oxidized and reduced states has occurred, these valves are closed as illustrated in FIG. 8. At this point, bed 322 in reactor 320 is a bed of substantially metal bromide in an oxidized state, while bed 312 in reactor 310 is substantially metal bromide in a reduced state. As illustrated in FIG. 8, valves 308 and 332 are opened and then valves 304, 317, 306 and 326 are closed, to permit the gas stream containing lower molecular weight alkanes to be transported or conveyed via lines 262, heat exchanger 352, wherein gas stream is heated to a range of about 150° C. to about 600° C. or preferably in the range of about 150° C. to about 300° C., when using the preferred iron bromide or copper bromide, through valve 308 and line 309 to reactor 320 to thermally decompose the solid phase metal bromide in an oxidized valence state to yield elemental bromine vapor and a solid metal bromide in a reduced state. When operated above about 250° C., the resultant bromine vapor may also react with the lower molecular weight alkanes contained in the gas stream over the heated bed of the solid metal bromide in an oxidized state to produce gaseous alkyl bromides and hydrogen bromide. The resultant bromine vapor, and any alkyl bromide and hydrogen bromide produced by reaction with the lower molecular-weight alkanes are transported with the gas stream containing lower molecular weight alkanes via lines 324 and 330 and heat exchanger 226 prior to being introduced into alkyl bromination reactor 230 (or to reactor 234 via heat exchanger 232 if significant amounts of lower molecular weight gaseous alkanes are brominated in second reactor 310 in a manner as noted above). As may be evident to the skilled artisan, lower molecular-weight hydrocarbons, bromine, and any alkyl bromides and hydrogen bromide which remain in reactor, are preferably purged out with a flow of inert gas (not shown) to inhibit the loss of hydrocarbons and bromine before cycling of the beds. Next, valve 300 is opened to permit bromine vapor emanating from reactor 246 to be transported via line 242 through exchanger 221 into reactor 310 wherein the solid phase metal bromide in a reduced valence state reacts with bromine to effectively store bromine as a metal bromide. In addition, valve 316 is also opened to permit the resulting gas, which is substantially devoid of bromine to be vented via lines 314 and 318. The reactors are operated in this manner until significant conversion of the beds of reduced metal bromide and oxidized metal bromide in reactors 310 and 320, respectively, to the corresponding oxidized and reduced states has occurred and then the reactors are cycled back to the flow schematic illustrated in FIG. 7 by opening and closing valves as previously discussed.

As will also be evident to the skilled artisan, the amount of active metal bromide such as FeBr2/FeBr3 deposited on the solid inert support (which may be expressed as weight percent loading of the metal, as atomic metal, on the inert solid support) will have an effect on the temperature changes that will occur across reactors 312 and 320, because of the ratio of the heats of reaction to the heat capacity of the solid inert support occurring in solid beds 312 and 322. Increasing the metal loading relative to the amount of inert support is desirable as it decreases the sizes of the vessels required for a specified bromine storage capacity, however the heat rise which occurs will be also be greater due to the relatively larger ratio of the heats of reaction to the heat capacity of the inert support. The resultant temperature rise may be excessive and could limit the equilibrium bromine-storage capacity of the reduced metal bromide due to the temperature dependence of this equilibrium. Thus the acceptable temperature rise may alternatively limit the cycle time or effectively limit the useful bromine storage capacity of the solid beds 312 and 322. The use of effluent gas recycle through an external heat exchanger by means of a blower or compressor (not shown) may be considered by the skilled artisan as a means to limit the temperature rise across reactors 310 and 320 during the bromine-storage step and also to effect cooling and heating of the solid beds 312 and 322 between the cycling steps of reactors 310 and 320. Although two reactors 310 and 320 are shown to illustrate the concept of the invention, it should be apparent to the skilled artisan that more than two reactors, i.e. three (or more) could be utilized in the implementation of the invention in certain embodiments, as a practical means to allow continuous process operation and also allow purging, cool-down and heat-up between the bromine storage and bromine generating steps.

Figure 9:
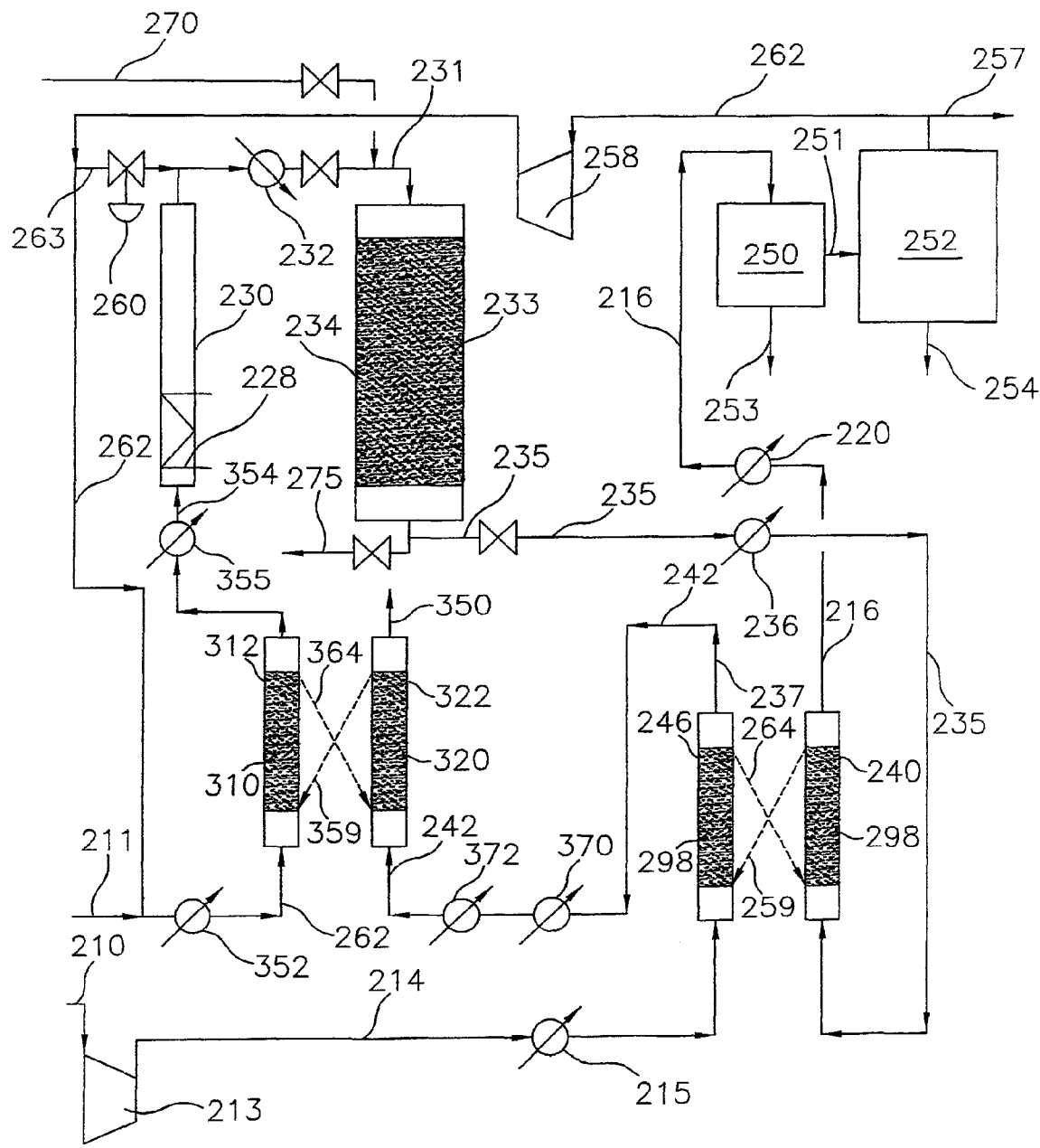
FIG. 9 is a schematic view of another embodiment of the processes of the present invention.

In the embodiment of the present invention illustrated in FIG. 9, the beds 312 and 322 contained in reactors 310 and 320, respectively, are fluidized and are connected in the manner described below to provide for continuous operation of the beds without the need to provide for equipment, such as valves, to change flow direction to and from each reactor. In accordance with this embodiment, the bromine-containing gas withdrawn from the reactor 246 via line 242 is cooled to a temperature in the range of about 30° C. to about 300° C. depending on the metal bromide selected in exchangers 370 and 372, and introduced into the bottom of reactor 320 which contains a moving solid bed 322 in a fluidized state. The flow of this introduced fluid induces the particles in bed 322 to flow upwardly within reactor 320 as the bromine vapor is reacted with the reduced metal bromide entering the bottom of bed 322 in the manner as described above with respect to FIG. 7. At or near the top of the bed 322, the particles, which contain a substantial amount of oxidized metal bromide on the attrition-resistant support due to the substantially complete reaction of the bromine vapor with the reduced metal bromide in reactor 320, are withdrawn via a weir, cyclone or other conventional means of solid/gas separation, flow by gravity down line 359 and are introduced at or near the bottom of the bed 312 in reactor 310.

As known to the skilled artisan, it may be advantageous to utilize a heat exchanger positioned within the moving bed of solids 322 to remove heat generated by the exothermic reaction occurring in reactor 320 in order to increase the extent of the temperature-dependent equilibrium reaction and thereby increase the bromine-storage capacity for a given mass flow of solids. The resulting gas which is substantially devoid of bromine is vented via line 350. In the embodiment illustrated in FIG. 9, the gas stream containing lower molecular weight alkanes, comprised of mixture of a feed gas (line 211) and a recycled gas stream, is transported or conveyed via line 262 and heat exchanger 352 wherein the gas stream is heated to a range of about 150° C. to about 600° C., or preferably in the range of about 150° C. to about 300° C., when using the preferred iron bromide or copper bromide, and introduced into reactor 310. The heated gas stream thermally decomposes the solid phase metal bromide in an oxidized valence state present entering at or near the bottom of bed 312 to yield elemental bromine vapor and a solid metal bromide in a reduced state and may also react the lower molecular weight alkanes contained in the gas stream over the heated bed of the solid metal bromide in an oxidized state to produce gaseous alkyl bromides, and hydrogen bromide. The flow of this introduced gas induces the particles in bed 312 to flow upwardly within reactor 310 as the oxidized metal bromide is thermally decomposed. At or near the top of the bed 312, the particles which contain a substantial amount of reduced solid metal bromide on the attrition-resistant support due to the thermal decomposition in reactor 310 are withdrawn via a weir or cyclone or other conventional means of gas/solid separation and flow by gravity down line 364 and introduced at or near the bottom of the bed 322 of particles in reactor 310. As will be evident to a skilled artisan, it may be advantageous to utilize a heat exchanger positioned within the moving bed of solids 312 to supply heat to the endothermic reaction occurring in reactor 310, in order to increase the extent of the temperature-dependent equilibrium reaction and thereby increase the bromine-generating capacity for a given mass flow of solids.

The resulting bromine vapor, alkyl bromide and hydrobromic acid is transported with the gas stream containing lower molecular weight alkanes via line 354 and heat exchanger 355 and introduced into alkyl bromination reactor 230 or to reactor 234 via heat exchanger 232 if significant amounts of lower molecular weight gaseous alkanes are brominated in second reactor 310 in a manner as noted above. In this manner, reactors 310 and 320 may be operated continuously without changing the parameters of operation.

Figure 10:
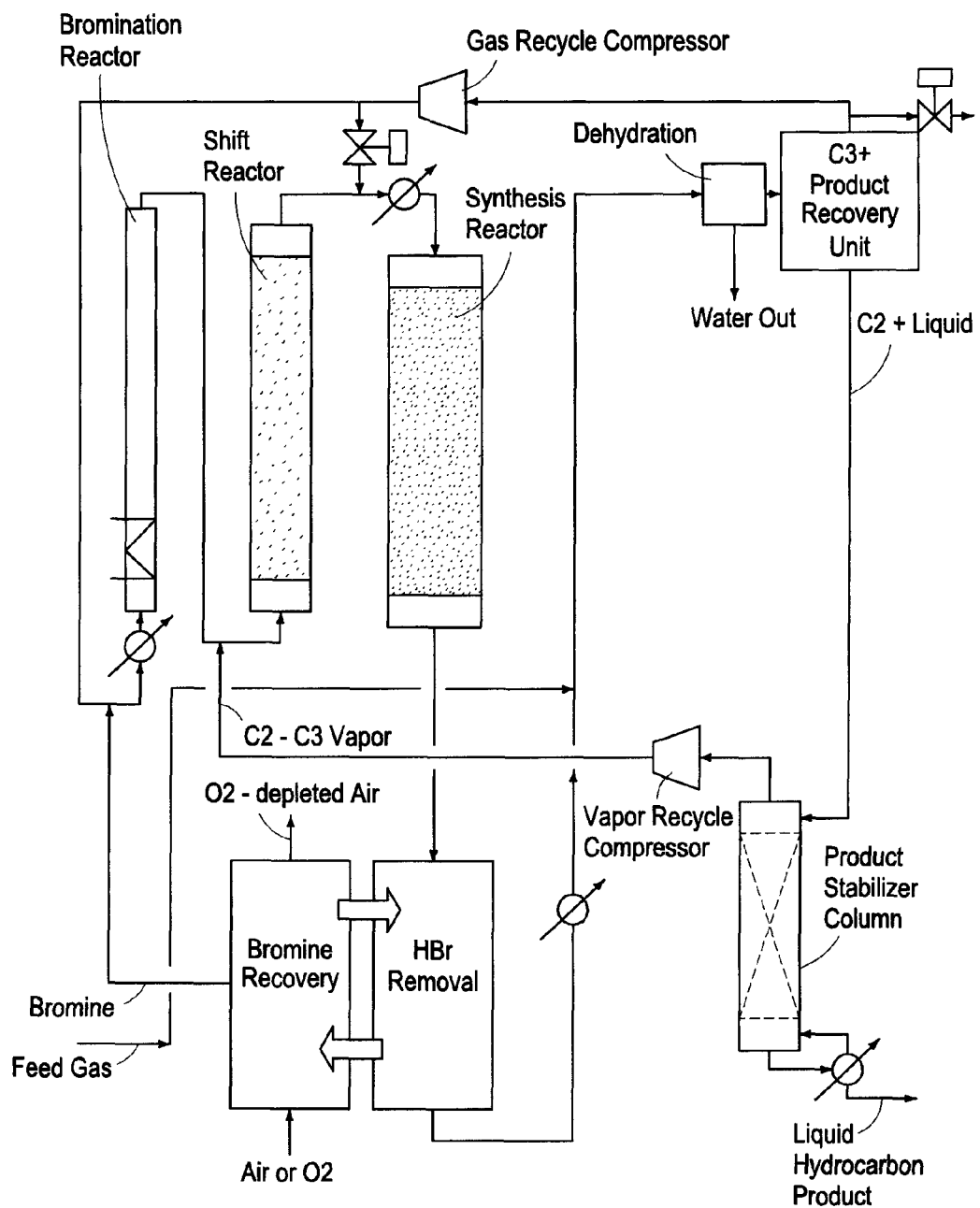
FIG. 10 is a simplified block flow diagram of the processes of the present invention configured in accordance with one embodiment of the present invention to reduce formation of multi-brominated alkanes.

A block flow diagram generally depicting the processes of the present invention is illustrated in FIG. 10 and depicts some aspects of certain embodiments of the processes of the present invention. In accordance with the general depiction of the processes of the present invention as illustrated in FIG. 10, the feed gas stream containing lower molecular weight alkanes may be pretreated to remove $C_{2+}$ components, and especially the $C_{3+}$ components prior to being combined with bromine vapor and conveyed to a bromination reactor. The concentration of $C_2$ components in the feed gas stream introduced into the bromination reactor may be from about 0.1 mol % to about 10.0 mol %, more preferably from about 0.5 mol % to about 5.0 mol %, and most preferably from about 1 mol % to about 5 mol %. While some $C_{3+}$ hydrocarbons may be tolerated in the bromination reactor, higher concentrations thereof may result in the rapid formation of carbon-containing coke-like solids which cause fouling and plugging in the bromination reactor as well as downstream components. The concentration of C3+ components in the feed gas stream introduced into the bromination reactor may be about 0.01 to 0.2 mol %, and preferably between about 0.01 to 0.1 mol % and most preferably between about 0.01 to 0.05 mol %. As illustrated in FIG. 10, the feed gas may be combined with the effluent from the synthesis reactor and pretreated to selectively remove $C_{2+}$, and particularly $C_{3+}$ components contained in the feed gas and also from the higher molecular-weight products of the process. More specifically, the feed gas, residual hydrocarbons and olefins, higher molecular weight hydrocarbons or mixtures thereof may be conveyed to a dehydration and product recovery unit wherein water is removed from the remaining constituents. The olefins, higher molecular weight hydrocarbons or mixtures thereof as well as $C_{2+}$ components may be then separated from the gas. The residual gas from the product recovery unit which is primarily methane with acceptable concentrations of $C_{2+}$ lower molecular alkane components as noted above may then be combined with bromine and conveyed to the alkane bromination stage of the processes of the present invention. The remaining $C_{2+}$ components and olefins, higher molecular weight hydrocarbons or mixtures thereof may be conveyed to a product stabilizer column in which the $C_{2+}$ components are removed from the liquid hydrocarbon product. The $C_{2+}$ components may be used in conjunction with a shift reactor in a manner as hereinafter described, while the liquid hydrocarbon product may be removed from the product stabilizer column for use or further petrochemical or fuel processing.

In accordance with the processes of the present invention as previously noted, the feed gas containing predominantly methane and acceptable amounts of $C_{2+}$ lower molecular weight alkane components may be reacted exothermically in the bromination reactor with dry bromine vapor at a relatively low temperature in the range of about 250° C. to about 600° C., and at a pressure in the range of about 1 bar to about 30 bar to produce gaseous alkyl bromides and hydrogen bromide. The upper limit of the operating temperature range is greater than the upper limit of the reaction initiation temperature range to which the feed mixture is heated due to the exothermic nature of the bromination reaction. In the case of methane, the formation of methyl bromide is believed to occur in accordance with the following general reaction:

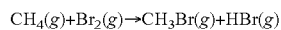

$$CH_4(g)+Br_2(g) \rightarrow CH_3Br(g)+HBr(g)$$

Due to the free-radical mechanism of the gas-phase bromination reaction, di-bromomethane and some tri-bromomethane and other alkyl bromides may be also formed. Bromination often occurs in the bromination reactor with a relatively high degree of selectivity to methyl bromide due to the alkane to bromine ratio employed. For example, in the case of the bromination of methane, a methane to bromine ratio of about 6:1 is believed to increase the selectivity to mono-halogenated methyl bromide to average approximately 88%, depending on reaction conditions, such as residence time, temperature, and turbulent mixing. At these conditions, some di-bromomethane and only extremely small amounts of tri-bromomethane approaching the detectable limits may also be formed in the bromination reaction. If a lower methane to bromine ratio of approximately 2.6 to 1 is utilized, selectivity to the mono-halogenated methyl bromide may fall to the range of approximately 65 to 75% depending on other reaction conditions. At a methane to bromine ratio significantly less than about 2.5 to 1, unacceptable low selectivities to methyl bromide occurs, and, moreover, significant formation of undesirable di-bromomethane, tri-bromomethane, and carbon soot may be observed. The relatively high methane to bromine ratio employed in the bromination reactor also ensures that bromine is substantially consumed in the bromination reactor thereby effectively inhibiting subsequent formation of free-radical bromination in subsequent stages of the processes of the present invention due to the presence of elemental bromine. The residence time of the reactants in the bromination reactor necessary to achieve such selectivity to mono-halogenated methyl bromide is relatively short and may be as little as 1-5 seconds under adiabatic reaction conditions. Higher alkanes, such as ethane, propane and butane, also may be brominated, resulting in mono and multiple brominated species such as ethyl bromides, propyl bromides and butyl bromides. Further, in some embodiments, the dry bromine vapor that is fed into the bromination reactor may be substantially water-free. Applicant has discovered that, at least in some instances, this may be preferred because it appears that elimination of substantially all water vapor from the bromination step substantially eliminates the formation of unwanted carbon dioxide. This may increase the selectivity of alkane bromination to alkyl bromides, thus possibly eliminating the large amount of waste heat generated in the formation of carbon dioxide from alkanes.

The $C_{2+}$ lower molecular weight alkane components removed from the liquid hydrocarbon product in the product stabilizer column may be combined with the effluent withdrawn from the bromination reactor that comprises alkyl bromides and hydrogen bromide and introduced into a shift reactor. [The small amount of unreacted bromine which is not reacted in the bromination reactor and which may be present in the effluent from the bromination reactor is readily consumed by thermal bromination reaction with $C_{2+}$ hydrocarbons prior to or upon introduction into the shift reactor.] In the shift reactor, a significant portion of the di- and tri-brominated alkanes that may be present in the alkyl bromides contained in the effluent from the bromination reactor may be selectively converted upon reaction with $C_{2+}$ components to mono-brominated alkanes. As an example, where $C_3$ and di-bromomethane are the reactants, it is believed that the conversion occurs in accordance with the following general reaction:

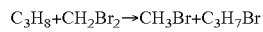

$$C_3H_8+CH_2Br_2 \rightarrow CH_3Br+C_3H_7Br$$

Although this reaction may proceed thermally without a catalyst, it has been determined that such thermal reaction requires unacceptably long residence time within the shift reactor and does not achieve satisfactory conversion rates to mono-brominated alkanes. Accordingly, it is preferred that the shift reactor contain a bed of suitable catalyst selected from Group VIII metals, Group VIB metals, Group IB metals, aluminum, zinc, vanadium, magnesium, calcium, titanium, yttrium, lanthanum or cerium and mixtures thereof. Group VIII metals include iron, cobalt, nickel, platinum, palladium, rhodium, ruthenium, iridium, osmium or mixtures of two or more thereof. Group VIB metals include tungsten, molybdenum or chromium. Group IB metals include copper or silver. Preferably, the Group VIII metal used in this embodiment of the present invention is a noble metal selected from platinum, palladium, rhodium, ruthenium, iridium, osmium, or mixtures of two or more thereof, and more preferably the Group VIII metal is platinum. Most preferably, the Group VIII metal is iron employed as a metal bromide, metal oxide or non-stoichometric metal oxy-bromide. Preferably the Group VIB metals are molybdenum or tungsten. Preferably the Group IB metal is copper employed as a metal bromide, metal oxide or metal oxy-bromide. Non-limiting examples of suitable metal catalysts listed above which may form more than one thermally reversible bromide salt as used in the processes of the present invention are iron, molybdenum, tungsten, copper, vanadium, chromium or mixtures of two or more thereof. Non-limiting examples of suitable catalysts listed above which may form single bromide salts as used in the processes of the present invention are cobalt, nickel, silver, zinc, magnesium, calcium, titanium, aluminum, lanthanum, cerium or mixtures of two or more thereof. These metals which form more than one thermally reversible bromide salt or a single bromide salt may be initially employed in the processes of the present invention as a bromide salt or an oxide since they would exist and function as bromides in the shift reactor due to conversion to bromide salts via a reaction with hydrobromic acid under the conditions employed in the shift reactor. Suitable supports are selected to have relatively low acidity to inhibit thermal decomposition and cracking of poly-brominated alkanes and have relatively low surface area to inhibit adsorption of the poly-brominated alkanes onto the support. Non-limiting examples of suitable supports for use with the catalyst in the shift reactor are silica, titania, zirconia or low surface area alumina, preferably having a specific surface area less than about 50 m2/g.

The catalyst is loaded and dispersed upon a suitable support to yield high activity in a cost effective manner as will be evident to a skilled artisan. For example, it is preferred to use a loading of from about 0.1 wt % to about 1 wt % and more preferably from about 0.3 wt % to about 0.5 wt % when platinum is employed as the catalyst in the shift reactor bed, while a loading of from about 1 wt % to about 10 wt % and more preferably 3 wt % to about 10 wt % is employed when palladium is employed as the catalyst. In the case of the preferred non-noble metals such as iron, molybdenum or mixtures thereof with higher loadings in the range of about 10% to about 20% or greater (as metal oxide) are cost-effective. When using a catalyst in the shift reactor, it is preferred to operate the reactor at from about 200° C. to about 500° C., more preferably from about 400° C. to about 500° C. The residence time of the reactants in the shift reactor necessary to achieve the desired selectivity to mono-brominated alkanes is relatively short and may be as little as 2 to 8 seconds.

The effluent from shift reactor 410 which contains a significantly increased ratio of mono-brominated alkanes to poly-brominated alkanes, i.e. di- or tri-brominated alkanes, may be transported to a synthesis reactor and reacted over a suitable catalyst (as described above in conjunction with reactor 34) in the presence of hydrogen bromide to form olefins, higher molecular weight hydrocarbons or mixtures thereof. The particular olefins, higher molecular weight hydrocarbons or mixtures thereof produced is dependent upon the catalyst employed in the synthesis, the composition of the alkyl bromides introduced into this reactor and the exact operating parameters employed in this reactor.

Hydrogen bromide may be removed from olefins, higher molecular weight hydrocarbons or mixtures in a hydrogen bromide (HBr) removal stage and may be conveyed to a bromine recovery stage wherein hydrogen bromide may be neutralized by a partially oxidized metal bromide salt to yield a metal bromide salt. The resultant metal bromide salt may be contacted with oxygen or air in the bromide recovery stage of the present invention to yield elemental bromine which may be recycled to the alkane bromination stage as a dry bromine vapor and a partially oxidized metal bromide salt which may be used to neutralize and remove additional hydrogen bromide removed from the olefins and higher molecular weight hydrocarbons produced by the process.

Figure 11:
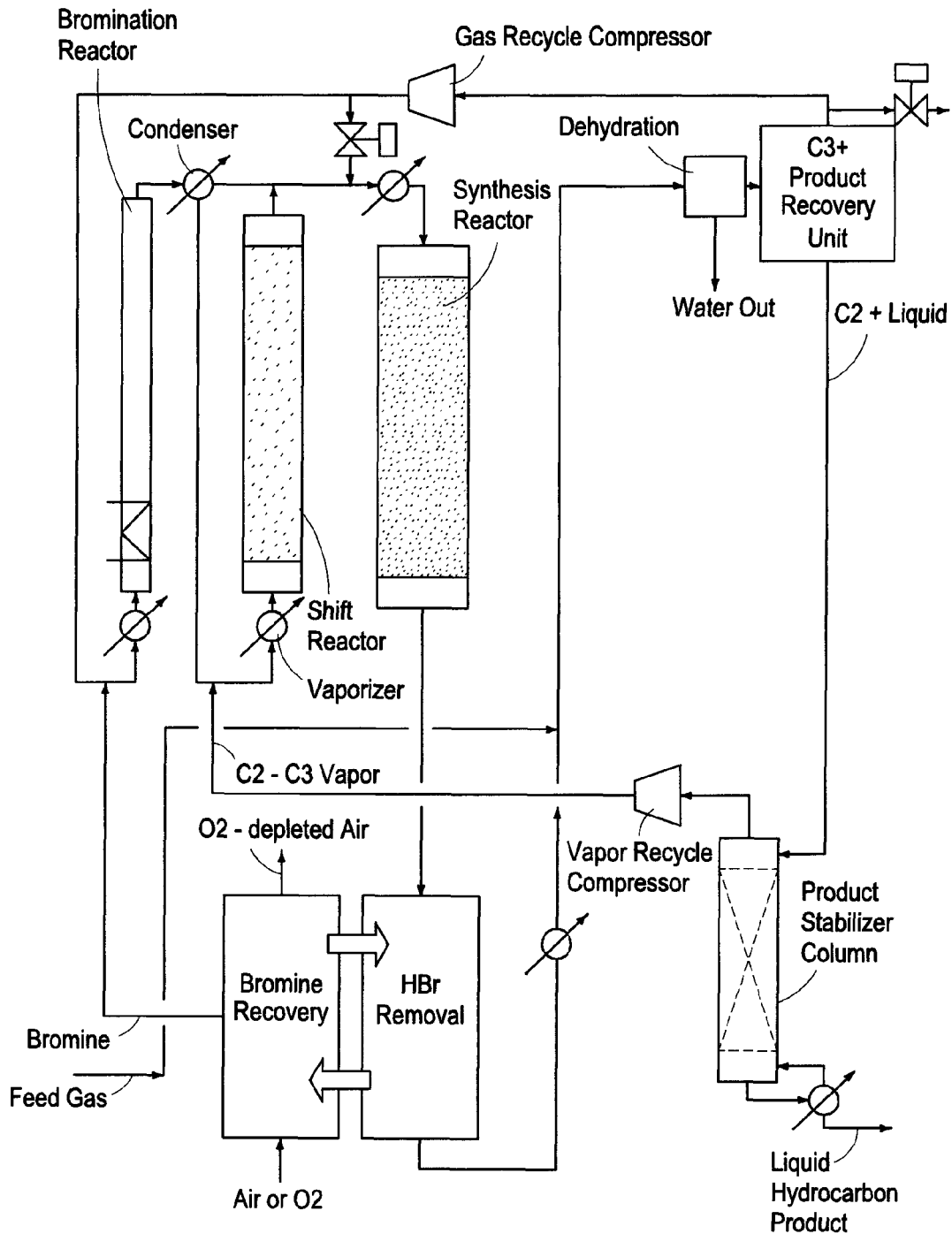
FIG. 11 is a simplified block flow diagram of the processes of the present invention configured in accordance with another embodiment of the present invention to reduce formation of multi-brominated alkanes.

A block flow diagram generally depicting the processes of the present invention is illustrated in FIG. 11 and depicts some aspects of certain embodiments of the processes of the present invention. In accordance with the general depiction of the processes of the present invention as illustrated in FIG. 11, a shift reactor is employed and the processes operated similar to the manner as described in conjunction with FIG. 10 except that the effluent from poly-brominated alkanes may be condensed from this stream by ambient cooling. The $C_{2+}$ lower molecular weight hydrocarbon component may be mixed with the separated multi-brominated alkanes which may be then vaporized and transported to the shift reactor to convert the poly-brominated alkanes in a manner as described above. Since only the multi-brominated alkane portion of the stream being transported to synthesis reactor is required to be treated in shift reactor, the embodiment of FIG. 11 advantageously requires a smaller shift reactor to attain the same conversion of multi-brominated alkanes to mono-brominated alkanes.

In accordance with the embodiments of the processes of the present invention described above and generally illustrated in FIGS. 10 and 11, undesirable multibrominated alkanes, for example di- and tri-brominated alkanes, typically formed during the conventional bromination of lower molecular weight alkanes may be effectively reduced to non deleterious levels. Concentrations of the $C_{2+}$ lower molecular weight hydrocarbons in the feed gas to the bromination reactor may be reduced, if necessary, to provide for relatively high concentrations of methane, e.g. 90 mol % or greater, in the feed gas being brominated. In addition, the methane to bromine ratio in the bromination reactor is selected to be at least about 2.5:1 so as to further ensure monobromination selectively. What small amount of multi-brominated alkanes may be formed after bromination in accordance with the processes of the present invention may be readily converted over a suitable catalyst in the shift reactor to mono-brominated alkanes. The very short residence times in both the bromination and shift reactors in the processes of the present invention permit use of reduced reactor vessel sizes to obtain significant conversion of multi-brominated alkanes, for example about 80% to about 100% conversion, most preferably greater than about 90% conversion. Furthermore, Applicants have discovered that relatively high concentrations of byproduct hydrogen bromide in the vapor phase (formed as a result of the bromination reaction), i.e. concentrations higher than about 30 mol %, may have a significant inhibitory effect on the dehydrohalogenation/oligimerization reaction conversion rate, believed due to an equilibrium adsorption of the hydrogen bromide on the acid sites on certain synthesis catalysts. At very high concentrations of hydrogen bromide, i.e. of about 50 mol %, the activity of the dehydrohalogenation/oligimerization catalyst is believed to be significantly inhibited and may result in reduced conversion. Thus, in addition to operating the bromination reaction at an alkane to bromine molar ratio in excess of about 2.5 for the purposes of minimizing the formation of deleterious amounts of multi-brominated alkanes, the higher molar ratio and presence of excess alkanes reduces the hydrogen bromide concentration in the bromination reactor effluent to less than about 30 mol %.

Figure 12:
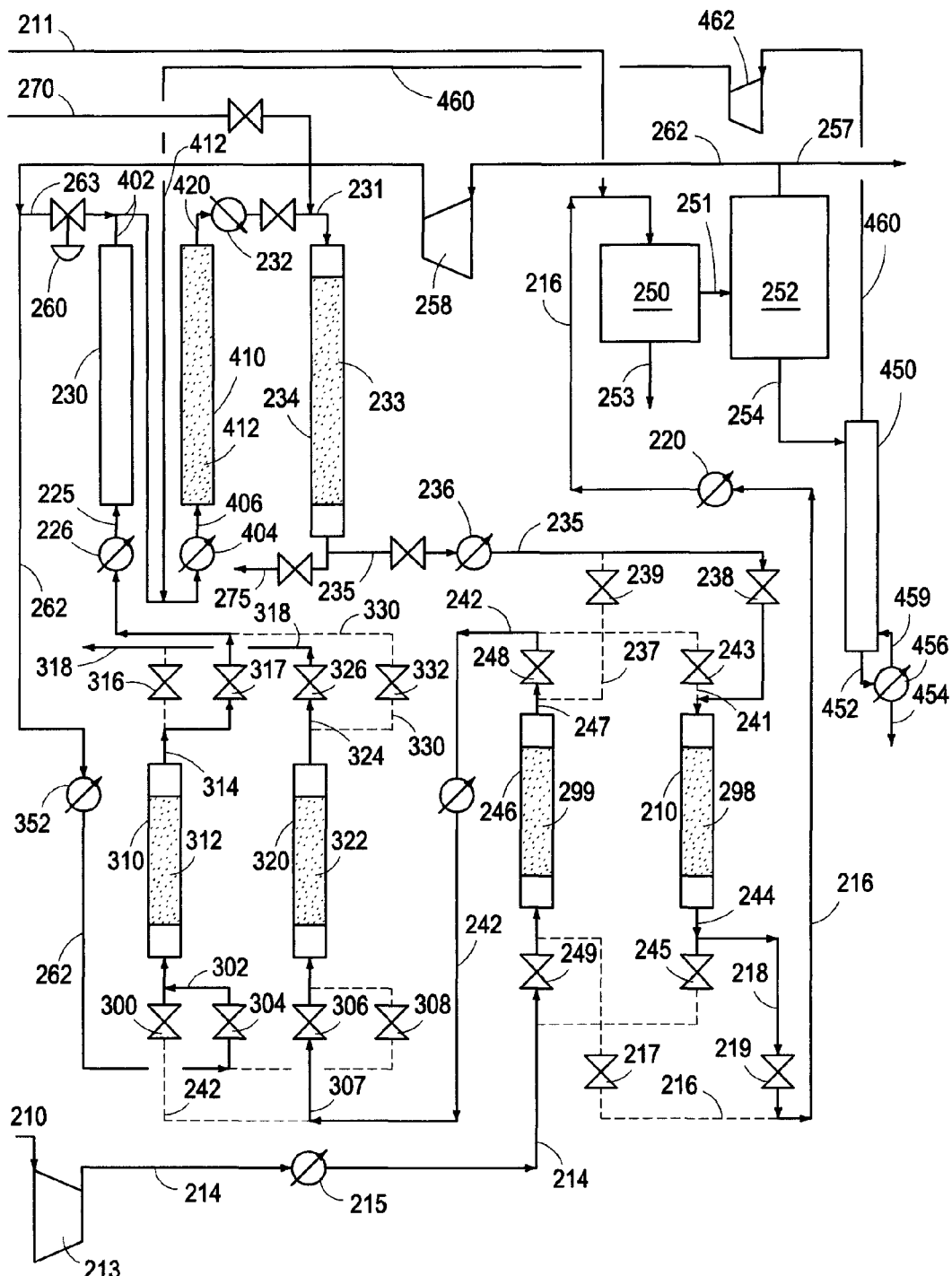
FIG. 12 is a schematic view of the embodiment of the processes of the present invention illustrated in FIGS. 7 and 8 and further configured in accordance with the block flow diagram of FIG. 10 to incorporate a shift reactor in a series configuration.

To illustrate a specific embodiment of the processes of the present invention that is generally illustrated in FIG. 10, an embodiment of the process of the present invention is illustrated in FIG. 12 and is similar in operation to the embodiment described in FIGS. 7 and 8 above but includes, among other additional equipment, a shift reactor 410, the operation and function of which are described below. In general, this embodiment pertains to effectively reducing the concentration of multi-brominated alkanes, for example di-, and tri-brominated alkanes, present in the alkyl bromides introduced into the second reactor.

In accordance with this embodiment, a gas stream containing lower molecular weight alkanes may be transported or conveyed via line, pipe or conduit 211, mixed with steam and high molecular hydrocarbons in line 216 and conveyed to dehydrator 250 to remove substantially all water from the gas stream. The water may be then removed from the dehydrator 250 via line 253. The dried gas stream containing the higher molecular weight hydrocarbons may be transported via line 251 to product recovery unit 252 to recover $C_3$ and $C_4$ as desired, but primarily the $C_{5+}$ fraction in line 254. Any conventional method of dehydration and liquids recovery such as solid-bed desiccant adsorption followed by, for example, refrigerated condensation, cryogenic expansion, or circulating absorption oil, as used to process natural gas or refinery gas streams, as known to a skilled artisan, may be employed in the implementation of this invention. In accordance with this embodiment of the present invention, the stream in line 254 may be conveyed to a stabilizer column in which is operated at conditions sufficient to remove at least a portion of the $C_2$-$C_5$ hydrocarbons in a gaseous phase from the remaining higher molecular weight hydrocarbons which are transported from the stabilizer 450 via line 452 to stabilizer reboiler 456 which produces vapor to strip residual $C_2$-$C_5$ hydrocarbons from the higher molecular weight hydrocarbons leaving the bottom of the stabilizer column 450. The higher molecular weight hydrocarbons may be removed from the process 454 as a fuel product, a blend or for further processing. The $C_2$-$C_5$ hydrocarbons may be removed from stabilizer column 450a gaseous phase in line 460 and pressurized in a compressor 462 for further use in the process as hereinafter described. While C$_2$-C$_5$ hydrocarbons may be removed from stabilizer column 450 and introduced with the feed into the shift reactor 410, it is preferred that the stabilizer column is operated at conditions to maximize the C$_3$ content of this hydrocarbon stream. Further, it is preferable to recover C$_5$ as a product rather than recycle it for further use in the process.

The vapor effluent from product recovery unit 252 that contains lower molecular weight alkanes may be split into a purge stream 257 that may be utilized as fuel for the process and a feed gas which is compressed via compressor 258. The gas discharged from compressor 258 may be split into two fractions. A first fraction is transported via line 262 to heat exchanger 352, wherein the gas stream may be preheated to a temperature in the range of about 150° C. to about 600° C. The heated gas stream may be then passed through valve 304 and line 302 to a second vessel or reactor 310 containing a bed 312 of a solid phase metal bromide in an oxidized valence state wherein the temperature of the gas stream thermally decomposes the solid phase metal bromide in an oxidized valence state to yield elemental bromine vapor and a solid metal bromide in a reduced state. In addition, the lower molecular weight alkanes contained in the gas stream may react over the heated bed 312 of the solid metal bromide in an oxidized state to produce gaseous alkyl bromides, hydrogen bromide and a solid metal bromide in a reduced state. By controlling the temperature of the gas stream and therefore the temperature of the bed 312 of the solid phase metal bromide in an oxidized valence state, the degree to which bromine is liberated and to which the lower molecular weight alkanes are brominated in second vessel or reactor 310 may be controlled. The resultant bromine vapor, alkyl bromide and hydrogen bromide may be transported with the gas stream containing lower molecular weight alkanes via lines 314, valve 317, line 330, heat exchanger 226 and line 225 prior to being introduced into alkyl bromination reactor 230 for further bromination of lower molecular weight alkanes contained in the gas stream. If significant amounts of the lower molecular weight gaseous alkanes are brominated in second vessel or reactor 310, the heat exchanger 226 and bromination reactor 230 may be eliminated from the process. Some C$_2$ for example about 0.1 to about 10 mol %, may be tolerated in the bromination reaction, however only small amounts of C$_3$ are tolerable, for example concentrations in excess of about 0.2 mol % in reactor 230 result in rapid formation of carbon-containing, coke-like solids which cause fouling and plugging in reactors 230, 410 and 234. This adverse condition is substantially inhibited in the process illustrated in FIG. 10 as a significant portion of C$_2$ and in particularly C$_{3+}$ hydrocarbons may be removed in product recovery unit 252 from vapor effluent that is ultimately fed to the first reactor 230.

The effluent that contains alkyl bromides and hydrogen bromide may be withdrawn from the first reactor 230 (or the second vessel or reactor 310 depending upon the extent of bromination achieved therein) via line 402. The second fraction vapor effluent from product recovery unit 252 may be drawn off line 262 via line 263, introduced into the effluent from the first reactor 230 in line 402, and regulated by control valve 260. The rate at which the second fraction may be introduced into the first reactor effluent in line 402 is sufficient to dilute the alkyl bromide concentration fed to reactor 410 and reactor 234 and absorb the heat of reaction such that reactor 410 and reactor 234 may be maintained at the selected operating temperatures. Thus, the dilution provided by the second fraction of vapor effluent permits selectivity of bromination in the first reactor 230 to be controlled in addition to moderating the temperature in shift reactor 410 and second reactor 234. In accordance with the embodiment illustrated in FIG. 10, the gas containing C$_2$-C$_5$ hydrocarbons in line 460 may be also introduced into the mixture of first reactor effluent and second fraction of vapor effluent contained in line 402 and the resultant mixture is passed to heat exchanger 404 wherein the mixture is heated to a temperature of from about 250° C. to about 450° C., more preferably from about 300° C. to about 400° C. and most preferably from about 350° C. to about 400° C. prior to be introduced into shift reactor 410 via line 406.

In shift reactor 410, a significant portion of the di- and tri-brominated alkanes that are present in the alkyl bromides contained in the effluent from first reactor 230 may be selectively converted upon reaction with C$_2$-C$_4$ hydrocarbons to mono-brominated alkanes. As an example, where C$_3$ and di-bromomethane are the reactants, it is believed that the conversion occurs in accordance with the following general reaction:

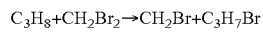

$$C_3H_8+CH_2Br_2\rightarrow CH_2Br+C_3H_7Br$$

Although this reaction may proceed thermally without a catalyst, it has been determined that such thermal reaction requires unacceptably long residence time within shift reactor 410 and does not achieve satisfactory conversions, thus it is preferred that shift reactor 410 contain a bed 412 of suitable catalyst selected as set forth above with respect to FIG. 10. When using a catalyst in shift reactor 410, it is preferred to operate the reactor at from about 250° C. to about 570° C., more preferably from about 300° C. to about 400° C. Heat exchanger 404 may be operated accordingly to heat the input to shift reactor 410 to the desired point within this range. The effluent from shift reactor 410 which contains a significantly increased ratio of mono-brominated alkanes to di- or tri-brominated alkanes may be withdrawn via line 231 and is partially cooled to a temperature in the range of about 150° C. to 450° C. in heat exchanger 232 before flowing to a second reactor 234. In second reactor 234, the alkyl bromides may be reacted exothermically at a temperature range of from about 250° C. to about 500° C., and a pressure in the range of about 1 bar to 30 bar, over a fixed bed 233 of suitable catalyst a mixture of higher molecular weight hydrocarbons and additional hydrogen bromide. In this embodiment of the present invention, reactors 240 and 246 may be operated in a cyclic fashion as discussed above with reference to FIGS. 4 and 5 and reactors 310 and 320 are operated in a cyclic fashion as discussed above in reference to FIGS. 7 and 8.

A high selectivity to mono-brominated alkanes in the stream introduced into second reactor 234 in accordance with the embodiment of FIG. 12 is highly desirable because the presence of di-brominated alkanes and tri-brominated alkanes results in the undesirably formation of heavy hydrocarbons, such as naphthalenes other poly-aromatics and coke, which significantly accelerate deactivation of the catalyst used in third reactor 234. The increased amount of mono-brominated alkanes, and in particular propyl bromide, in the second reactor will also result in a desirable increase of C$_4$-C$_8$ hydrocarbons, including iso-octane, being formed in reactor 234.

Although the embodiment of FIG. 12 has been described as using a C$_2$-C$_4$ stream, and preferably a C$_3$ rich stream, that is separated from higher molecular weight hydrocarbons in stabilizer column 450 prior to introduction with the feed to shift reactor 410, this C$_2$-C$_4$ stream, and preferably a C$_3$ rich stream, may be obtained from any suitable source, for example from commercially available natural gas or propane, as will be evident to a skilled artisan.

Figure 13:
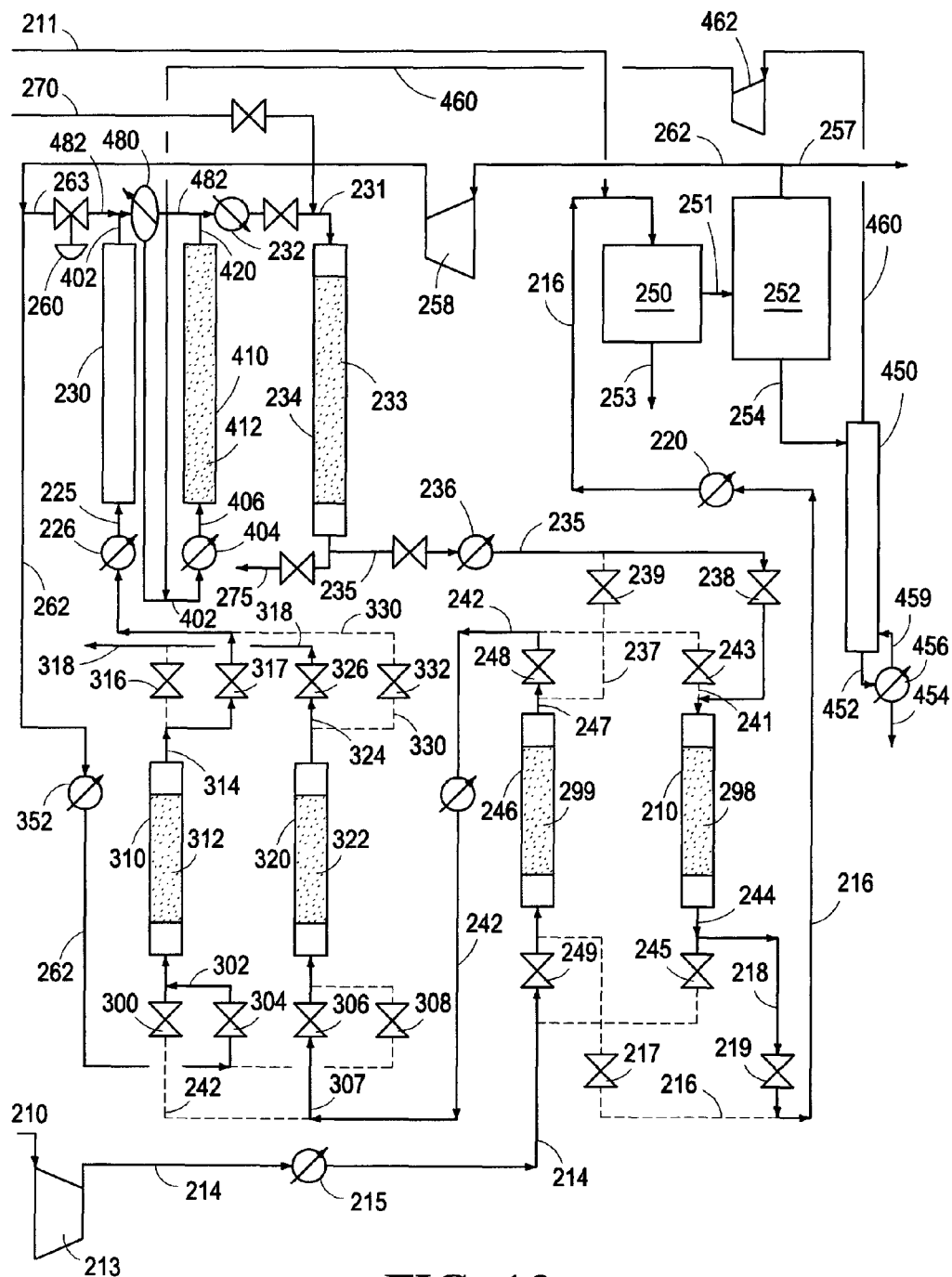
FIG. 13 is a schematic view of the embodiment of the processes of the present invention illustrated in FIGS. 7 and 8 and further configured in accordance with the block flow diagram of FIG. 10 to incorporate a shift reactor in a parallel configuration.

Another embodiment of the processes of the present invention illustrated in FIG. 13 is similar in design and operation to that illustrated in FIG. 12 and described above except that the effluent that contains alkyl bromides and hydrogen bromide withdrawn from the first reactor 230 (or the second vessel or reactor 310 depending upon the extent of bromination achieved therein) and the second fraction vapor effluent from product recovery unit 252 contained in line 402 may be conveyed to a condenser 480 wherein the di- and tri-brominated alkanes are condensed from this stream by ambient cooling and transported via line 402. The $C_2$-$C_5$ hydrocarbons in line 460 may be mixed with the separated di and tri brominated alkanes in line 402 and transported to shift reactor 410 to convert the di and tri brominated alkanes in a manner as described above. The shift reactor 410 preferably contains a catalyst as described above with respect to the embodiment of FIG. 10. The effluent from the shift reactor 410 may be withdrawn via line 420 and combined with remaining stream in line 482 prior to introduction to reactor 234 as described above with respect to FIG. 10. Since only the di- and tri-brominated alkane portion of the stream being transported to reactor 234 is required to be pretreated in shift reactor 410, the embodiment of FIG. 13 advantageously requires a smaller reactor 410 to attain the same conversion of di- and tri-brominated alkanes to mono-brominated alkanes.

While the shift reactor has been described above and illustrated in FIGS. 12 and 13 as being included in the embodiment of the processes of the present invention illustrated in FIGS. 7 and 8, a shift reactor may also be employed in any of the processes of the present invention as will be evident to those of ordinary skill in the art with the benefit of this disclosure. Further, the use of a shift reactor in conjunction with a bromination reactor has broad application to processes in which alkanes are brominated to form mono-brominated alkanes which are suitable intermediates in chemical processes so as to effectively inhibit any deleterious effects in subsequent use or processing due to the presence of polybrominated alkanes.

Figure 16:
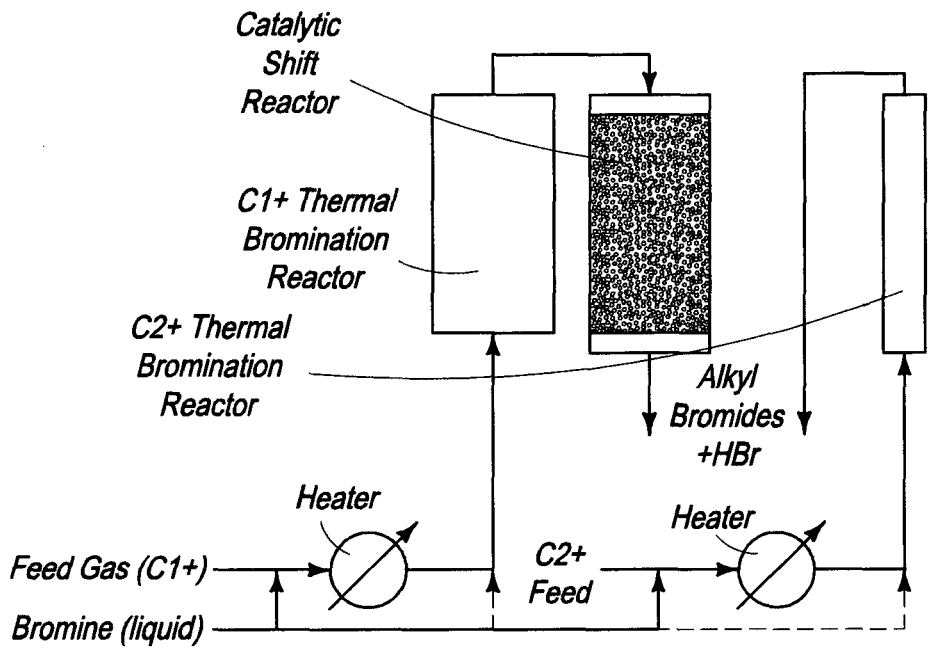
FIG. 16 is a schematic view of the processes of the present invention configured in accordance with an embodiment of the present invention to incorporate a catalytic shift reactor in a series configuration to reduce formation of multi-brominated alkanes.

In accordance with an embodiment of the processes of the present invention generally illustrated in FIG. 16, bromine liquid is combined with a methane ($CH_4$) containing feed gas. The liquid bromine may be first mixed with the gaseous feed and the mixture heated to effect vaporization of the bromine, or the gas may be first super-heated and liquid introduced into the hot gas where it is vaporized. It is preferred that the feed gas containing lower molecular weight alkanes be processed if necessary, by refrigerated condensation, cryogenic expansion, circulating solvent or other separation means normally employed in natural gas processing plants, oil refineries, etc., to reduce concentrations of the $C_{2+}$ lower molecular weight hydrocarbons in the feed gas so as to provide for relatively high concentrations of methane, e.g. 90 mol % or greater, in the predominately methane containing feed gas being brominated. While some $C_2$ hydrocarbons may be tolerated in the bromination reactor for example in concentrations in the range of about 0.1 mol % to about 10 mol %, concentrations of $C_{3+}$ hydrocarbons in excess of about 0.2% may result in the rapid formation of carbon-containing coke-like solids which cause fouling and plugging in the bromination reactor as well as downstream components. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

The ratio of methane to bromine that may be utilized in the feed to the thermal bromination reactor is a function of the $C_{2+}$ content of the feed as well as the temperature. Lower $C_{2+}$ content in the feed and operation at lower temperatures may allow operation at lower methane to bromine ratios. Further, if the constraint of complete reaction of all the bromine occurring in the thermal bromination step is not required, as is the case when the catalytic shift reactor of the present invention is operated downstream of thermal bromination, this may facilitate operation at lower temperatures and hence operation at methane to bromine substantially below the minimum ratio of 2.5 to 1 stated for previously discussed embodiments.

Hence with the addition of the catalytic shift reactor and with appropriate control of the $C_{2+}$ content of the feed gas, the molar ratio of methane to bromine in the feed to the thermal bromination reaction is less than about 7 to 1 but greater than about 1.25 to 1, and preferably less than about 4 to 1 but greater than about 1.5 to 1, and more preferably less than about 3 to 1 but greater than about 1.67 to 1. The feed gas and liquid bromine mixture may be conveyed to a heat exchanger wherein the mixture is heated to a temperature between about 300° C. to about 550° C., but more preferably in the range of about 450° C. to about 500° C., and wherein the liquid bromine is vaporized.

Further, in some embodiments, the dry bromine vapor in the mixture fed into the thermal bromination reactor may be substantially water-free. Applicant has discovered that, at least in some instances, this may be preferred because it appears that elimination of substantially all water vapor from the bromination step substantially eliminates the formation of unwanted carbon dioxide. This may increase the selectivity of alkane bromination to alkyl bromides, thus possibly eliminating the large amount of waste heat generated in the formation of carbon dioxide from alkanes.

The heated feed gas, containing predominantly methane and acceptable amounts of $C_{2+}$ lower molecular weight alkane components, and bromine vapor mixture may be first transported to a $C_{1+}$ thermal bromination reactor wherein lower molecular weight alkanes, predominantly methane and lower molecular weight alkanes, present in the feed gas are thermally brominated. If necessary, the thermal bromination reactor may contain an inlet pre-heater zone (similar to zones 28, 128 and 228 described above) to ensure that the mixture remains heated to a reaction initiation temperature in the range of about 300° C. to about 500° C. In the case of methane, the formation of methyl bromide is believed to occur in accordance with the following general reaction:

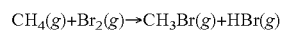

$$CH_4(g)+Br_2(g)\rightarrow CH_3Br(g)+HBr(g)$$

The resultant mixture of alkyl bromides, hydrogen bromide, unreacted bromine and feed gas containing unreacted alkanes, predominately methane, may be removed from thermal bromination reactor and transported to a catalytic shift reactor. The temperature of this feed to the catalytic shift reactor may in the range of about 350° C. to about 570° C., more preferably 500° C. to about 570° C., and most preferably 530° C. to about 570° C. As the thermal bromination reaction is exothermic, the feed gas and bromine introduced to the thermal bromination reactor may be heated to a temperature within the about 300° C. to about 500° C. range to ensure that the effluent from the thermal bromination reactor is within the desired range for introduction into the catalytic shift reactor given the reactor operating conditions of the thermal bromination reactor as will be evident to a skilled artisan. Alternatively, the effluent mixture from the thermal bromination reactor may be heated or cooled to a temperature within the range of about 350° C. to about 570° C. prior to contact with the catalyst employed in the catalytic shift reactor by any suitable means as evident to a skilled artisan.

The catalyst useful in the catalytic shift reactor in the embodiment of the processes of the present invention illustrated generally in FIG. 16 may be a metallic element that is capable of forming both metal halides or metal oxy-halides, or mixtures thereof, and include Fe, Mo, La, Ce, W, Cr, Co, Ni, Cu, Ag, Zn, Mn, V, Nb, Ta, Ti, Y, Zr, Mg and Ca. Halogens that may be useful for the formation of catalytically-active metal halides or metal oxy-halides are Br, Cl and F, with Br being preferred.

While the catalyst may be initially prepared as a metal bromide dispersed on a catalyst support, it is generally more common to disperse a metal oxide by an incipient wetness technique utilizing a metal nitrate solution precursor, followed by drying and calcination at high-temperature in air or other oxidizing gas mixture. Further, as many metal bromide salts are hygroscopic, handling, storage and transport may require special measures. Accordingly the catalyst used in the shift reactor may be most practically, commercially available in only the metal oxide state. Such a metal oxide catalyst may be initially employed in the catalytic shift reactor of FIG. 16 as it will be converted into a metal bromide or metal oxy-bromide, or mixtures thereof over time due to the reaction thereof with hydrogen bromide, methyl bromide, di-bromomethane or other alkyl bromides. However, as activity of a metal oxide catalyst in the catalytic shift reactor is appreciably less than that of a metal bromide or metal oxy-bromide and carbon losses or coking is increased until conversion is completed, it may be desirable to convert the initial metal oxide catalyst in-situ to a metal bromide or metal oxy-bromide, or mixtures thereof prior to introduction of feed into the catalytic shift reactor by any suitable means, such as by reaction with hydrogen bromide and a carrier gas, for example methane or nitrogen.

In the catalytic shift reactor, a significant portion of the di- and tri-brominated alkanes that may be present in the alkyl bromides contained in the effluent from the thermal bromination reactor may be selectively converted upon reaction with the unreacted alkane components, predominantly methane, present in the feed, to mono-brominated alkanes. As an example, where $C_1$ and di-bromomethane are the reactants, it is believed that the conversion occurs in accordance with the following general reaction:

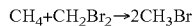
$CH_4 + CH_2Br_2 \rightarrow 2CH_3Br$

Due to the high temperatures in the both the thermal and catalytic reactors, elemental bromine is likely to be essentially completely converted. It is believed that the catalyst used in the catalytic shift reactor promotes a selective reaction of di-bromomethane with methane to yield methyl bromide via a selective catalytic reaction of bromine (supplied by dissociative adsorption of di-bromomethane on the catalyst surface) with methane.

The effluent from the catalytic shift reactor which contains a significantly increased ratio of mono-brominated alkanes to di- or tri-brominated alkanes may be transported for further processing, such as to a synthesis reactor in accordance with the embodiments of the processes of the present invention illustrated in FIGS. 1-9 and described above in detail.

The $C_{2+}$ components produced by the process or contained in the feed gas which are removed so that the feed to the $C_{1+}$ thermal bromination contains an acceptable amount of $C_{2+}$ and in particular $C_{3+}$ may be processed in a $C_{2+}$ thermal bromination reactor using a fraction of the liquid bromine feed. The $C_{2+}$ thermal bromination reactor operates at an alkane to bromine ratio of in the range of about 4 to 1 about 1.25 to 1, and preferably in the range of about 2 to 1 about 1.5 to 1 and at a temperature in the range of about 250° C. to 550° C. The effluent from the $C_{2+}$ thermal bromination contains various alkyl bromides and hydrogen bromide may be further processed, for example by being commingled with the effluent from the catalytic shift reactor and transporting the mixture to a catalytic synthesis reactor, wherein the various alkyl bromides in the mixture undergo dehydrohalogenation/oligimerization reactions to produce higher molecular-weight hydrocarbon products and additional hydrogen bromide.

Figure 17:
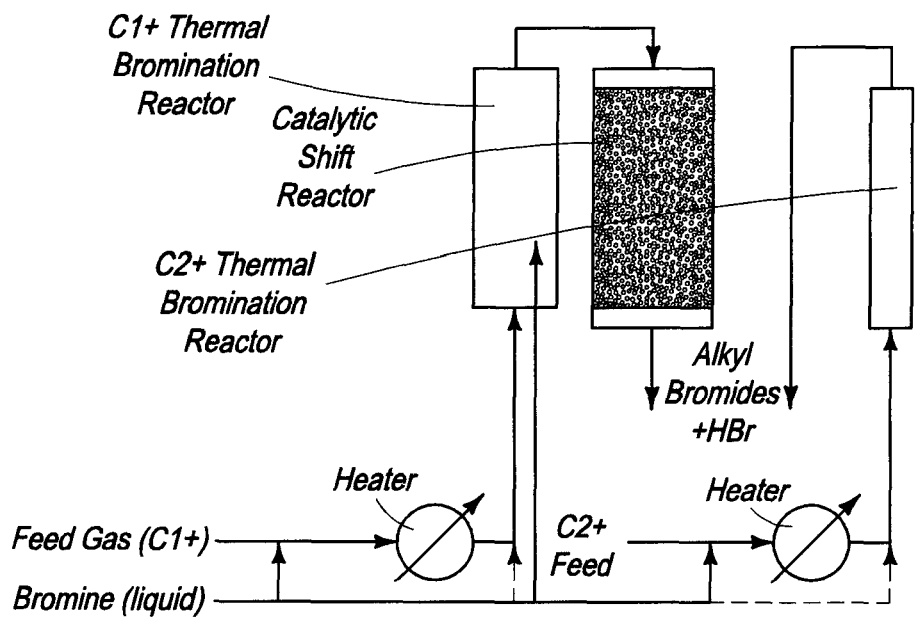
FIG. 17 is a schematic view of the processes of the present invention configured in accordance with another embodiment of the present invention to incorporate a catalytic shift reactor in a series configuration to reduce formation of multi-brominated alkanes.

An embodiment of the processes of the present invention generally illustrated in FIG. 17 is similar to that illustrated in FIG. 16 and described above, except that while bromine liquid is combined with a methane (CH4) containing feed gas prior to transportation to a heat exchanger wherein the liquid bromine is vaporized (alternatively the gas may be first superheated and liquid introduced into the hot gas where it is vaporized), a separate stream of bromine liquid is also introduced directly into the bromination reactor by spray or any other suitable means, such as evaporation of liquid bromine from the surface of an inert packing material. Since thermal bromination proceeds exothermically, the heat of the bromination reaction is sufficient to vaporize the liquid bromine directly injected into the reactor thereby minimizing the heat duty and heat exchange requirements and costs associated therewith. The amount of liquid bromine injected directly into the reactor is determined by the methane to bromine ratio that is selected and the desired effluent temperature from the thermal bromination reactor. For example if the higher the overall methane to bromination ratio the larger the fraction of liquid bromine that may be injected directly into the reactor, so long as the minimum initiation temperature of the bromination is sustained and the reaction not quenched. Conversely, at a specified fixed methane to bromine ratio, as the fraction of liquid bromine that is directly injected into the reactor is increased, the lesser the temperature rise that will occur across the thermal bromination reactor, as long as the minimum reaction temperature is sustained.

Figure 18:
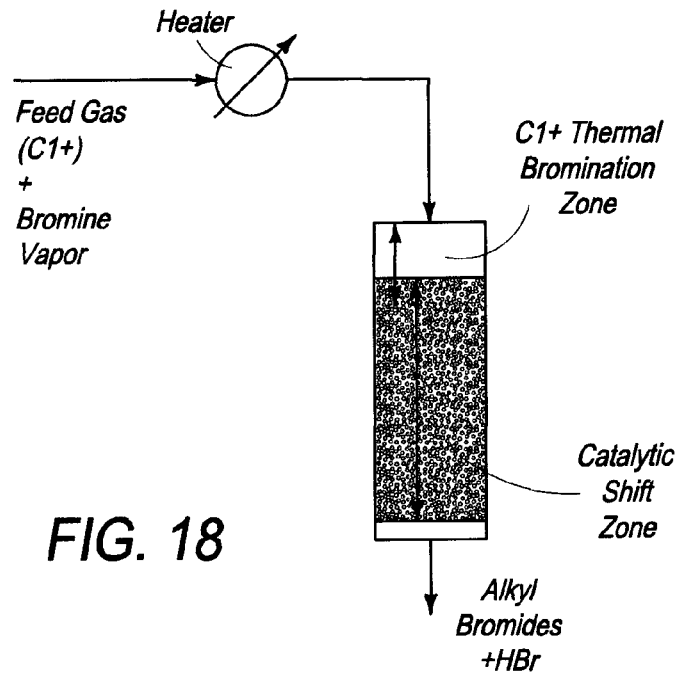
FIG. 18 is a schematic view of the processes of the present invention configured in accordance with a further embodiment of the present invention to incorporate a catalytic shift reactor in a parallel configuration to reduce formation of multi-brominated alkanes.

An embodiment of the processes of the present invention generally illustrated in FIG. 18 is similar to that illustrated in FIG. 16 and described above, except that the heated mixture of feed gas and bromine vapor may be transported directly to a reactor containing a suitable catalyst as illustrated in FIG. 18 wherein thermal and catalytic bromination are allowed to proceed substantially in series. The reactor may be sized to have a sufficient head space above the catalyst bed to define a thermal bromination zone wherein heated mixture of feed gas, containing predominantly methane and acceptable amounts of $C_{2+}$ lower molecular weight alkane components, and bromine vapor are thermally brominated. If necessary, the thermal bromination zone may contain an inlet pre-heater zone (similar to zones 28, 128 and 228 described above) to ensure that the mixture remains heated to a reaction initiation temperature in the range of about 300° C. to about 530° C. In the case of methane, the formation of methyl bromide is believed to occur in accordance with the following general reaction:

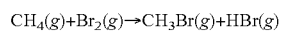
$CH_4(g) + Br_2(g) \rightarrow CH_3Br(g) + HBr(g)$

The resultant mixture of alkyl bromides, hydrogen bromide, unreacted bromine and feed gas containing unreacted alkanes, predominately methane, flow into a catalytic shift reaction zone.

The temperature of this feed to the catalytic shift reaction zone may in the range of about 350° C. to about 570° C., more preferably 500° C. to about 570° C., and most preferably 530° C. to about 570° C. As the thermal bromination reaction is exothermic, the feed gas and bromine introduced to the thermal bromination zone must be heated to a temperature within the about 300° C. to about 500° C. range to ensure that the effluent from the thermal bromination zone is within the desired range for introduction into the catalytic shift reaction zone given the reactor operating conditions in the thermal bromination zone as will be evident to a skilled artisan. Alternatively, the effluent mixture from the thermal bromination zone may be heated or cooled prior to contact with the catalyst employed in the catalytic shift reaction zone by any suitable means as evident to a skilled artisan.

The catalyst useful in the catalytic shift reaction zone in the embodiment of the processes of the present invention illustrated generally in FIG. 18 may be a metallic element that is capable of forming both metal halides or metal oxy-halides, or mixtures thereof, and include Fe, Mo, La, Ce, W, Cr, Co, Ni, Cu, Ag, Zn, Mn, V, Nb, Ta, Ti, Y, Zr, Mg and Ca. Halogens that may be useful for the formation of catalytically-active metal halides or metal oxy-halides are Br, Cl and F, with Br being preferred. The catalyst may be initially prepared as a metal bromide dispersed on a catalyst support, however it is generally more common to disperse a metal oxide by an incipient wetness technique utilizing a metal nitrate solution precursor, followed by drying and calcination at high-temperature in air or other oxidizing gas mixture. Further, as many metal bromide salts are hygroscopic, handling, storage and transport may require special measures. Hence the catalyst used in the shift reactor may be most practically, commercially available in only the metal oxide state. Such a metal oxide catalyst may be initially employed in the catalytic shift reaction zone of the reactor illustrated in FIG. 18 as it will be converted into a metal bromide or metal oxy-bromide, or mixtures thereof over time due to the reaction thereof with hydrogen bromide, methyl bromide, present in the bromination reaction effluent. However, as activity of a metal oxide catalyst in the catalytic shift reaction zone is appreciably less than that of a metal bromide or metal oxy-bromide and carbon losses or coking is increased until conversion is completed, it may be desirable to convert the metal oxide catalyst to a metal bromide or metal oxy-bromide, or mixtures thereof prior to introduction of feed into the catalytic shift reaction zone by any suitable means, such as by reaction with hydrobromic acid and a carrier gas, for example methane or nitrogen.

In the catalytic shift reaction zone in the reactor illustrated in FIG. 18, a significant portion of the poly-brominated alkanes, e.g. di- and tri-brominated alkanes, that may be present in the alkyl bromides contained in the effluent from the thermal bromination zone may be selectively converted upon reaction with the unreacted alkane components, predominantly methane, present in the feed to this zone, to mono-brominated alkanes. As an example, where $C_1$ and di-bromomethane are the reactants, it is believed that the conversion occurs in accordance with the following general reaction:

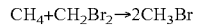

$$CH_4 + CH_2Br_2 \rightarrow 2CH_3Br$$

Due to the high temperatures in both the thermal and catalytic reactors, bromine is essentially completely converted. It is believed that the catalyst used in the catalytic shift reactor promotes a selective reaction of di-bromomethane with methane to yield methyl bromide via a selective catalytic reaction of bromine (supplied by dissociative adsorption of di-bromomethane on the catalyst surface) with methane.

Although the free-radical thermal bromination reactions may occur entirely in the free gas phase in the thermal bromination zone, at least a portion of the free radical Bromination may occur and be substantially completed within the void spaces present in a shallow region of the catalytic reactor bed in the catalytic shift reaction zone, while still achieving the desired selectivity to mono-bromomethane at the outlet of the catalytic shift reaction zone.

The effluent from the catalytic shift reaction zone which contains a significantly increased ratio of mono-brominated alkanes to di- or tri-brominated alkanes may be transported for further processing, such as to a synthesis reactor in accordance with the embodiments of the processes of the present invention illustrated in FIGS. 1-9 and described above in detail. As with the embodiments in FIGS. 16 and 17, the $C_{2+}$ components produced by the process or contained in the feed gas which are removed so that the feed to the $C_{1+}$ thermal bromination contains an acceptable amount of $C_{2+}$ and in particular $C_{3+}$ may be processed in a $C_{2+}$ thermal bromination reactor as illustrated in FIGS. 16 and 17 using a fraction of the liquid bromine feed and the effluent further processed.

Figure 19:
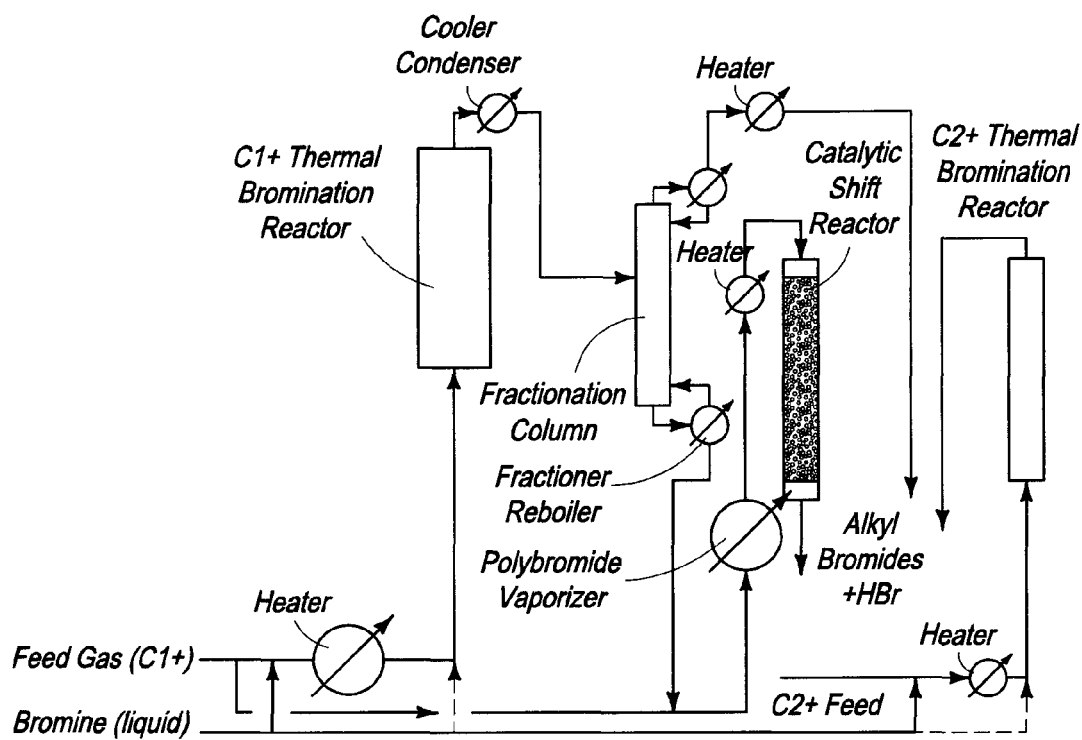
FIG. 19 is a schematic view of the processes of the present invention configured in accordance with a still further embodiment of the present invention to incorporate a catalytic shift reactor in a parallel configuration to reduce formation of multi-brominated alkanes.

In accordance with an embodiment of the processes of the present invention generally illustrated in FIG. 19, bromine liquid is combined with a methane ($CH_4$) containing feed gas. The liquid bromine may be first mixed with the gaseous feed and the mixture heated to effect vaporization of the bromine, or the gas may be first super-heated and liquid introduced into the hot gas where it is vaporized. It is preferred that the feed gas containing lower molecular weight alkanes be treated, if necessary, to reduce concentrations of the $C_{2+}$ lower molecular weight hydrocarbons in the feed gas so as to provide for relatively high concentrations of methane, e.g. 90 mol % or greater, in the predominately methane containing feed gas being brominated. While some $C_{2+}$ hydrocarbons may be tolerated in the bromination reactor, higher concentrations thereof, and in particular, higher concentrations of $C_{3+}$ hydrocarbons, may result in the rapid formation of carbon-containing coke-like solids which cause fouling and plugging in the bromination reactor as well as downstream components. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

The ratio of methane to bromine that may be utilized in the feed to the thermal bromination reactor, is a function of the $C_{2+}$ content of the feed as well as the temperature. Lower $C_{2+}$ content in the feed and operation at lower temperatures may allow operation at lower methane to bromine ratios. Further, if the constraint of complete reaction of all the bromine occurring in the thermal bromination step is not required, as is the case when the catalytic shift reactor of the present invention is operated downstream of thermal bromination, this may facilitate operation at lower temperatures and hence operation at methane to bromine substantially below the previously preferred minimum ratio of 2.5 to 1. Hence with the addition of the catalytic shift reactor and with appropriate control of the $C_{2+}$ content of the feed gas, the molar ratio of methane to bromine in the feed gas to the thermal bromination reactor is less than about 7 to 1 but greater than about 1.25 to 1, and preferably less than about 4 to 1 but greater than about 1.5 to 1, and more preferably less than about 3 to 1 but greater than about 1.67 to 1. The feed gas is passed to a heat exchanger between about 300° C. to about 550° C., but more preferably in the range of about 350° C. to about 500° C. and wherein the liquid bromine is vaporized.

The heated feed gas is introduced in the reactor wherein the bromination of the lower molecular weight alkanes present in the feed gas containing predominantly methane and acceptable amounts of $C_{2+}$ lower molecular weight alkane components may proceed thermally. If necessary, the thermal bromination reactor may contain an inlet pre-heater zone (similar to zones 28, 128 and 228 described above) to ensure that the mixture remains heated to a reaction initiation temperature in the range of about 300° C. to about 550° C. In the case of methane, the formation of methyl bromide is believed to occur in accordance with the following general reaction:

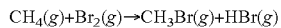

$$CH_4(g)+Br_2(g) \rightarrow CH_3Br(g)+HBr(g)$$

The resultant mixture of unreacted bromine, alkyl bromides, hydrogen bromide and feed gas containing unreacted alkane, predominately methane, may be subsequently cooled and transported to a fractionation column wherein poly-brominated alkanes, e.g. bi- and tri-brominated alkanes, are removed from this mixture. The fractionation column bottom liquid containing such poly-brominated alkanes are passed to the fractionator reboiler which vaporizes a fraction of the liquid stripping the residual lighter mono-bromomethane from the heavier poly-brominated alkanes in the liquid; these vapors are recycled to the fractionator. The poly-brominated alkanes are then combined with the feed gas containing predominately methane and vaporized and preheated to a temperature of about 450° C. to about 500° C. and introduced to a catalytic shift reactor wherein the poly-brominated alkanes are reacted with methane to further form predominately mono-brominated alkanes and hydrogen bromide. The alkyl bromides and hydrogen bromide may be transported from the catalytic shift reactor for further processing, such as to a synthesis reactor in accordance with the embodiments of the processes of the present invention illustrated in FIGS. 1-9 and described above in detail. The components in the fractionator overhead vapor which have been separated from the poly-brominated alkanes in the fractionation column may be conveyed to a condenser wherein any remaining poly-brominated alkanes may be condensed and refluxed to the fractionation column. The remaining stream comprising predominately alkyl bromides and hydrogen bromide may also be transported for further processing, such as to a synthesis reactor in accordance with the embodiments of the processes of the present invention illustrated in FIGS. 1-9 and described above in detail.

The $C_{2+}$ components produced by the process or contained in the feed gas which are removed so that the feed to the C1+ thermal bromination contains an acceptable amount of $C_{2+}$ and in particular $C_{3+}$ may be processed in a $C_{2+}$ thermal bromination reactor using a fraction of the liquid bromine feed. The $C_{2+}$ thermal bromination reactor operates at a alkane to bromine ratio of in the range of about 4 to 1 to about 1.25 to 1, and preferably in the range of about 2 to 1 to about 1.5 to 1 and at a temperature in the range of about 250° C. to 550° C. The effluent from the $C_{2+}$ thermal bromination contains various alkyl bromides and hydrogen bromide may be further processed, for example by being commingled with the effluent from the catalytic shift reactor and the mixture passed to a catalytic synthesis reactor, wherein the various alkyl bromides in the mixture undergo dehydrohalogenation/oligimerization reactions to produce higher molecular-weight hydrocarbon products and additional hydrogen bromide.

The catalyst useful in the catalytic shift reactor in the embodiment of the processes of the present invention illustrated generally in FIG. 19 may be a metallic element that is capable of forming both metal halides or metal oxy-halides, or mixtures thereof, and include Fe, Mo, La, Ce, W, Cr, Co, Ni, Cu, Ag, Zn, Mn, V, Nb, Ta, Ti, Y, Zr, Mg and Ca. Halogens that may be useful for the formation of catalytically-active metal halides or metal oxy-halides are Br, Cl and F, with Br being preferred. The catalyst may be initially prepared as a metal bromide dispersed on a catalyst support, however it is generally more common to disperse a metal oxide by an incipient wetness technique utilizing a metal nitrate solution precursor, followed by drying and calcination at high-temperature in air or other oxidizing gas mixture. Further, as many metal bromide salts are hygroscopic, handling, storage and transport may require special measures. Hence the catalyst used in the shift reactor may be most practically, commercially available in only the metal oxide state. Such a metal oxide catalyst may be initially employed in the catalytic shift reactor of FIG. 16 as it will be converted into a metal bromide or metal oxy-bromide, or mixtures thereof over time due to the reaction thereof with hydrogen bromide, methyl bromide, di-bromomethane or other alkyl bromides in the effluent from the thermal bromination reaction. However, as activity of a metal oxide catalyst in the catalytic shift reactor is appreciably less than that of a metal bromide or metal oxy-bromide and carbon losses or coking is increased until conversion is completed, it may be desirable to convert the metal oxide catalyst to a metal bromide or metal oxy-bromide, or mixtures thereof prior to introduction of feed into the catalytic shift reactor by any suitable means, such as by reaction with hydrobromic acid and a carrier gas, for example methane or nitrogen.

In the catalytic shift reactor, a significant portion of the di and tri brominated alkanes that may be present in the alkyl bromides contained in the effluent from the thermal bromination reactor may be selectively converted upon reaction with the unreacted alkane components, predominantly methane, present in the feed, to mono-brominated alkanes. As an example, where $C_1$ and di-bromomethane are the reactants, it is believed that the conversion occurs in accordance with the following general reaction:

$$CH_4+CH_2Br_2 \rightarrow 2CH_3Br$$

Due to the high temperatures in both the thermal and catalytic reactors, bromine is essentially completely converted. It is believed that the catalyst used in the catalytic shift reactor promotes a selective reaction of di-bromomethane with methane to yield methyl bromide via a selective catalytic reaction of bromine (supplied by dissociative adsorption of di-bromomethane on the catalyst surface) with methane.

The catalytic bromination process schematics, including the bromination reactor(s), illustrated in FIGS. 16-19 and described above can be utilized in lieu of the bromination process schematics, including reactors 30, 130 and 230, in any of the embodiments of the process of the present invention illustrated in FIGS. 2-13 and described above. Bromination in accordance with any of the catalytic bromination embodiments of the processes of the present invention as illustrated generally in FIGS. 16-19 is believed to result in increased carbon efficiencies at much lower methane to bromine ratios over those achieved by other bromination schematics. This may result in higher product yields, longer cycle lengths, reduction in vessel volumes and gas-recycle, product recovery, and utility requirements, thereby dramatically improving the overall economics of the process.

While the embodiments of the processes of the present invention illustrated in FIGS. 16, 17 and 19 and described above disclose different manners of vaporizing liquid bromine to obtain a mixture of bromine vapor and an appropriate feed gas for introduction into a bromination reactor, it will be evident to a skilled artisan that the bromination reactors described in these embodiments can be operated simply by feeding a mixture of appropriate feed gas and bromine vapor in instances where bromine is available either commercially or as a process stream in a vapor form. Further, while the embodiment of the processes of the present invention illustrated in FIG. 18 and described above disclose heating a mixture of appropriate feed gas and bromine vapor prior to introduction into a bromination reactor, it will be evident to a skilled artisan that bromine liquid can be vaporized in accordance with the embodiments of FIG. 16, 17 or 19 prior to introduction into the bromination reactor described in this embodiment where bromine is available either commercially or as a process stream in a liquid form.

Although the means for heating the feed gas, bromine mixture to a temperature sufficient to initiate thermal bromination is illustrated in FIGS. 16-19 as a simple externally-heated heat exchanger, other methods of heating this mixture will be evident to a skilled artisan. For example, heating by cross-exchange with other hot process streams, injection of hot inert materials, electromagnetic radiation, ionizing radiation, electrical discharge and pilot flames can be utilized to heat the mixture of feed gas and bromine vapor to a temperature sufficient to initiate thermal bromination. These methods may be performed prior to introduction of the mixture into a thermal bromination reactor or zone, in the thermal bromination reactor or zone, or both.

To facilitate a better understanding of the present invention, the following examples of certain aspects of some embodiments are given. The following examples should not be read or construed in any manner to limit, or define, the entire scope of the invention.

Example 1

Figure 14:
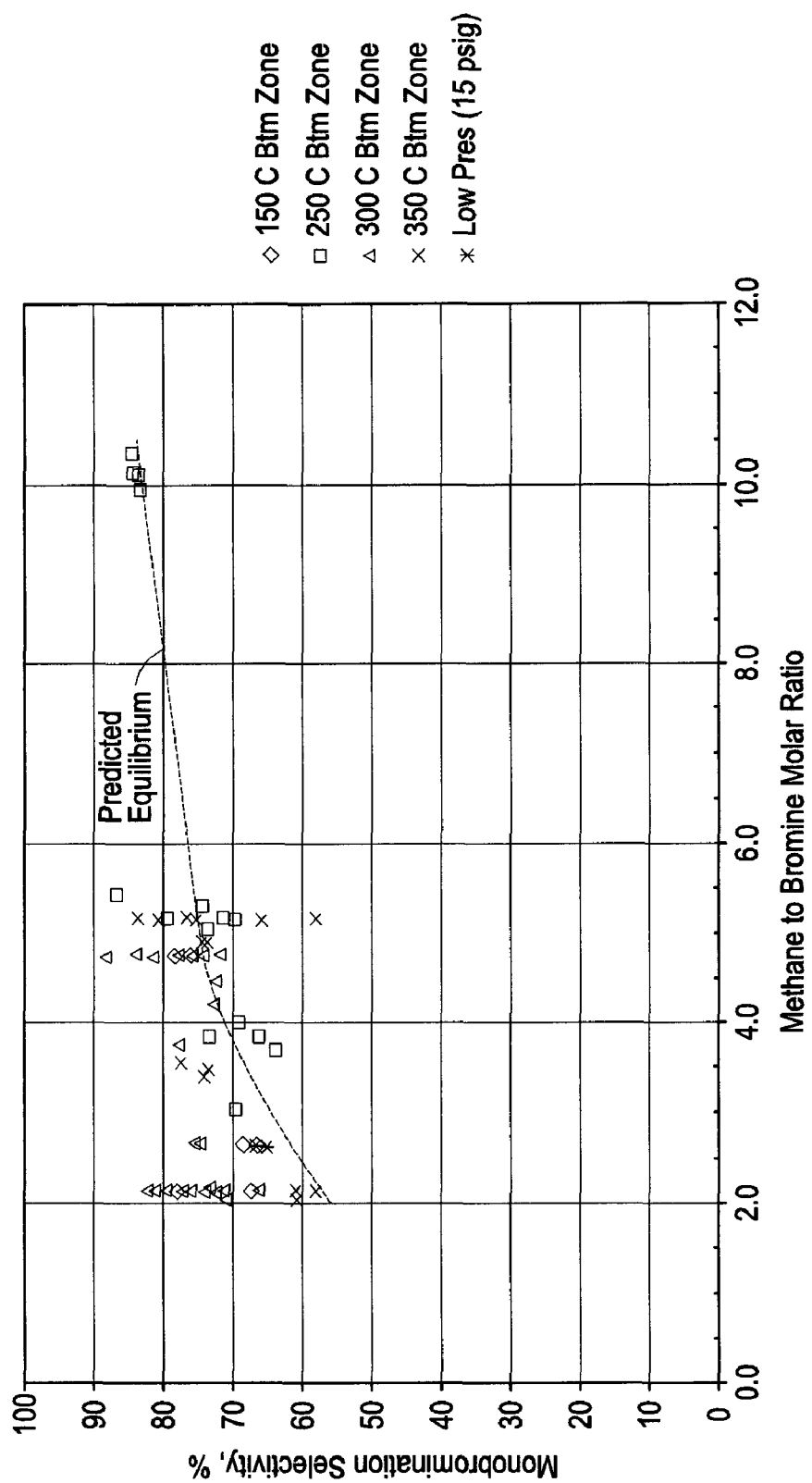
FIG. 14 is a graph of monobromination selectivity for varying methane to bromine molar ratios used in the bromination stage of the present invention.
Figure 15:
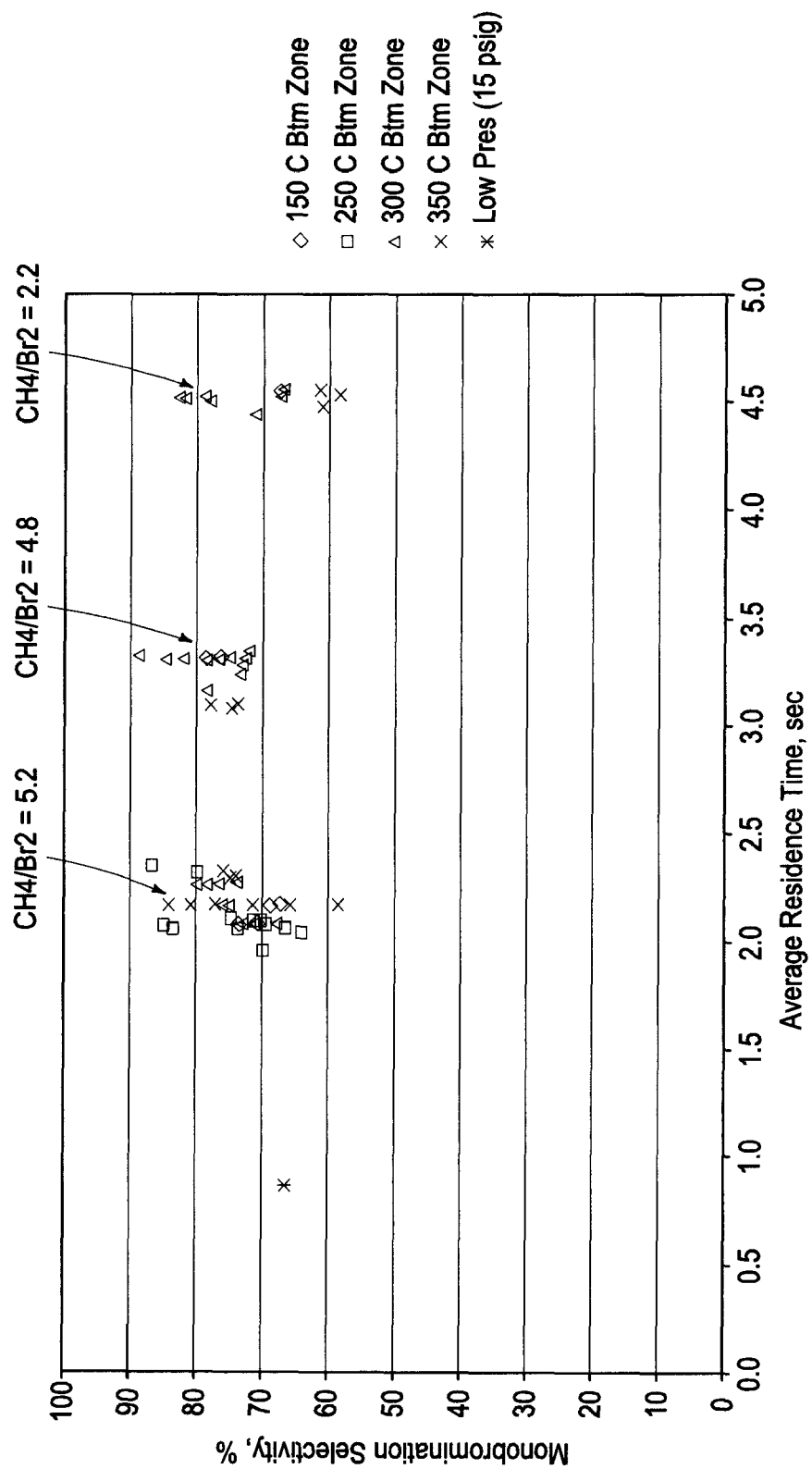
FIG. 15 is a graph of monobromination selectivity versus average residence time for varying methane to bromine molar ratios employed in the bromination stage of the present invention.

A mixture of methane and vaporized bromine at various mixture ratios is flowed vertically upward through a un-packed tubular reactor which is externally heated in three zones using electrical heating elements. The top (outlet) zone is maintained at an average temperature of about 494° C., the middle zone is maintained at an average temperature of about 450° C. and the inlet (preheat) zone is operated at various temperatures over the range of about 150° C. to about 300° C. Reaction residence times ranged from about 2.0 to 4.5 seconds. As depicted in FIG. 14, increasing the molar ratio of methane to bromine introduced into the bromination reactor above 2.5 results in a significant increase in monobromination selectivity of approximately 70%. At molar ratios of methane to bromine of about 5, monobromination selectivity averages about 80%, while at molar ratios of methane to bromine of about 10, monobromination selectivity exceeds 80%. As further depicted in FIG. 15, this increased monobromination selectivity at methane to bromine ratios above 2.5 is achieved at short residence times of about 3.25 seconds for a ratio of 4.8 and about 2 seconds for a ratio of about 5.2. At an example set of data points taken at a low methane to bromine ratio of about 2.1 which is below the preferred minimum ratio of about 2.5, CH3Br concentration in the reactor effluent averages about 16.8 mol %, CH2Br2 concentration averages about 6.8 mol % and the HBr concentration is undesirably high, averaging about 33.7 mol %. At a methane to bromine ratio of about 2.6, just above the minimum preferred ratio of about 2.5, CH3Br concentration in the reactor effluent averages about 15.4 mol %, CH2Br2 concentration averages about 5 mol % and the HBr concentration averages about 26.4 mol %. At a more-preferred methane to bromine ratio of about 4.8, CH3Br concentration in the reactor effluent averages about 10.7 mol %, CH2Br2 concentration averages about 3.1 mol % and the HBr concentration averages about 16.8 mol %.

Example 2

An externally heated open-tube (nominal ⅜-inch diameter) laboratory-scale thermal bromination reactor (R-1a) is operated upstream in series with a nominal 1-inch diameter catalytic shift reactor (R-1b) operating at about 490° C. and a GHSV of about 650° $hr^{-1}$, according to the invention. Flows of methane, bromine and nitrogen are controlled to target feed $CH_4:Br_2$ ratios of either 3:1 or 2:1 to the first open-tube thermal bromination reactor. For each of the two targeted CH4:Br2 feed ratio mixtures the first open tubular thermal bromination reactor is heated (with a three-zone temperature profile from the bottom inlet to the top outlet at 425° C., 450° C. and 470° C.) to initiate the thermal gas-phase free-radical bromination reaction in the open tube thermal reactor. The compositions of samples of the inlet and outlet gases to the Catalytic Shift Reactor are shown in the table below for the two different target methane-bromine mixtures. When the thermal bromination is initiated upstream of the catalytic shift reactor, the feed to the catalytic shift reactor has a relatively low selectivity to mono-bromomethane (MeBr or $CH_3Br$) and a relatively high selectivity to di-bromomethane (DBM or $CH_2Br_2$), nevertheless the $CH_2Br_2$ formed in the thermal bromination reaction reacts with excess un-reacted alkane (methane) over the catalyst in the catalytic shift reactor to convert the $CH_2Br_2$ to $CH_2Br$ resulting in a high final outlet selectivity to the mono-bromomethane (See results in Table 1 and 2).

TABLE 1

3 to 1 Methane:Bromine Ratio

| | Target Open-tube Feed Open-tube Reactor at 425/450/475° C. (thermal bromination reaction initiated) | Sample Inlet Shift Reactor | Sample Outlet Shift Reactor |
|---|---|---|---|
| $CH_4$, mol % | 52.5 | 42.7 | 39.9 |
| $Br_2$, mol % | 17.5 | 0.0 | 0.0 |
| $CH_3Br$, mol % | 0.0 | 8.2 | 14.0 |
| $CH_2Br_2$, mol % | 0.0 | 6.3 | 1.0 |
| Mono-bromomethane Selectivity, % | | 56.6 | 93.3 |

TABLE 2

2 to 1 Methane:Bromine Ratio

| | Target Open-tube Feed Open-tube Reactor at 425/450/470° C. (thermal bromination reaction initiated) | Sample Inlet Shift Reactor | Sample Outlet Shift Reactor |
|---|---|---|---|
| $CH_4$, mol % | 46.7 | 33.0 | 27.9 |
| $Br_2$, mol % | 23.3 | 0.0 | 0.0 |
| $CH_3Br$, mol % | 0.0 | 8.4 | 17.2 |
| $CH_2Br_2$, mol % | 0.0 | 8.4 | 1.8 |
| Mono-bromomethane Selectivity, % | | 50.0 | 90.5 |

Example 3

An externally heated laboratory-scale catalytic shift reactor (nominal 1-inch diameter) is operated at about 490° C. and a GHSV of about 650 $hr^{-1}$, according to the invention. Flows of methane, bromine and nitrogen are controlled to target feed $CH_4:Br_2$ ratios of 3:1 and are preheated to about 175° C. in the first open tube thermal bromination reactor (R-1a) and fed to the catalytic shift reactor (R-1b).

Figure 20:
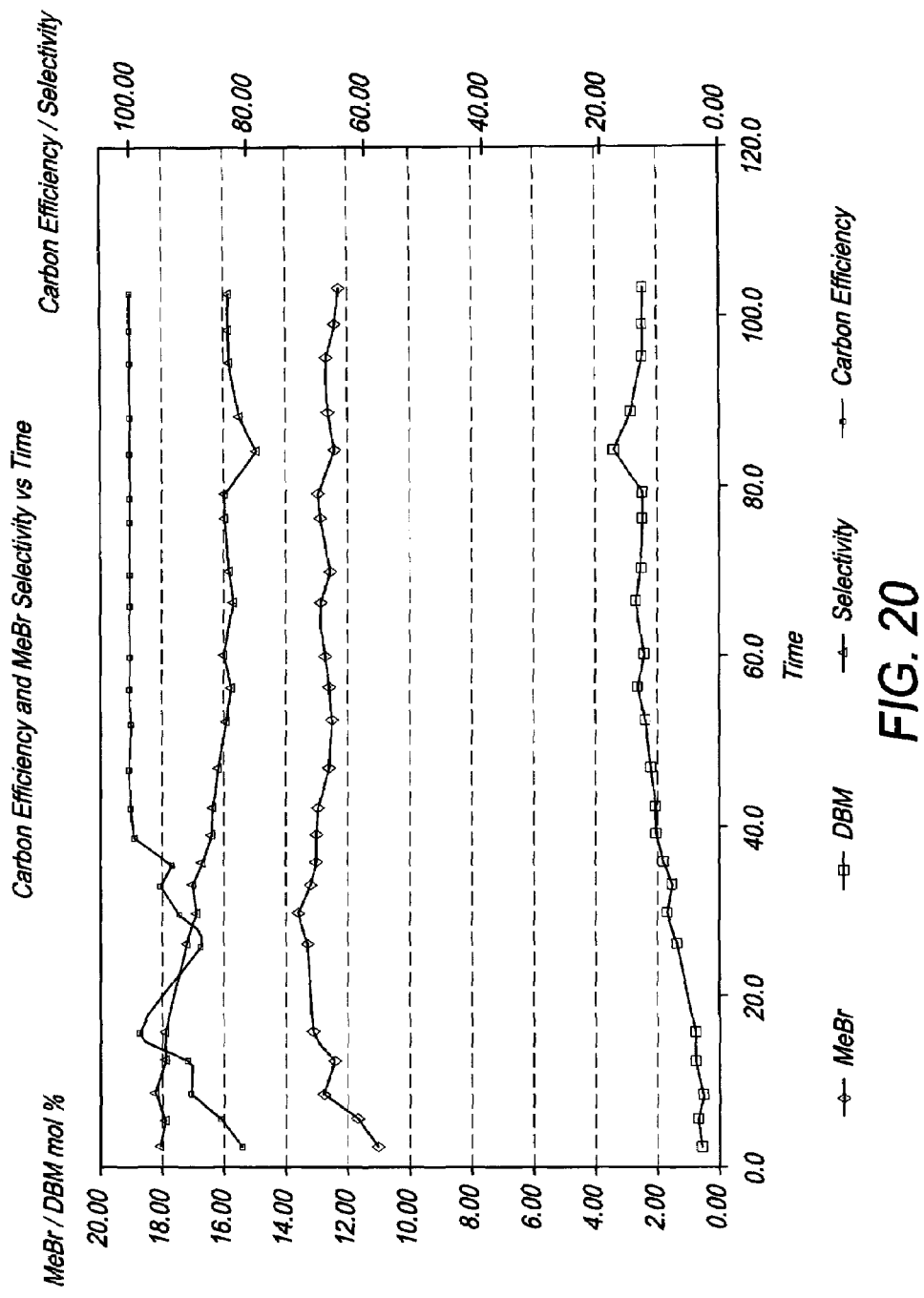
FIG. 20 is a graph of carbon efficiency and monobromination selectivity for varying methane vs. time in the bromination stage of an embodiment of the processes of the present invention.

The catalyst was initially composed of a mixture of iron oxide and molybdenum oxide dispersed on a silica support, prepared using a wet precursor impregnation/post calcination method. Prior to each test the catalyst is maintained at a temperature of about 490° C. and calcinated/regenerated with a mixture of oxygen and nitrogen for several hours to insure that the catalyst was in an initial oxide form, then purged with N2, prior to the introduction of the methane-bromine reactants. As illustrated in FIG. 20, the amount of $CH_3Br$ (MeBr) increases with time for approximately the first 30 hours and the amount of $CH_2Br_2$ (DBM) increases at a slower rate over about 60 hours. Similarly, the carbon efficiency (defined as a percentage of the amount of $(CH_3Br+CH_2Br_2)$ observed in the reactor compared against the amount of CH4 which is reacted) increases for about the first 40 hours and is maintained at nearly 100% thereafter past 100 hrs. This indicates that the catalyst, which is initially in the oxide state, is less active and that some of the $CH_3Br$ and $CH_2Br_2$ is initially lost to the formation of coke or carbonaceous deposits on the catalyst. Over the course of the run it can be seen that the catalyst becomes more active and the rate of coking declines, and it can be inferred that a least a portion of the metal oxide(s) present on the catalyst are converted to metal bromides or oxy-bromides by reaction of the metal oxide(s) with the hydrogen bromide (HBr) by-product of the free-radical bromination reaction and also possibly from some of the alkyl bromides ($CH_3Br$ and/or $CH_2Br_2$). Furthermore, when a control experiment is run (not illustrated in FIG. 20) in which the catalyst, initially in an oxide state from calcination in an oxygen-nitrogen mixture, is preconditioned by passing a mixture of HBr and $N_2$ over the catalyst for an extended period of time, prior to the introduction of the methane and bromine reactants, initial observed carbon efficiencies of near 100% are observed and the high efficiencies are sustained throughout the test run.

Thus, the desired functioning of the catalyst in its most active, stable state involves the presence of metal bromides and/or metal oxy-bromides. This can be obtained by initial deposition of suitable metal bromides on an inert support. Preferably, these stable active species can be obtained in-situ under reaction conditions starting with the catalyst containing a suitable metal or mixture of metals initially in oxide states, but more preferably can be obtained by in situ, pre-conversion/pre-activation of the initial metal oxides(s) to metal bromide or metal oxy-bromide states using hydrogen bromide.

Example 4

An externally heated laboratory-scale catalytic shift reactor (nominal 1-inch diameter) is operated at various temperatures at a GHSV of about 650 hr$^{-1}$, according to the invention. Flows of methane, bromine and nitrogen are controlled to target feed $CH_4$:$Br_2$ ratios of 3:1 and preheated to about 175° C. in the first open tube thermal bromination reactor (R-1a) and fed to the catalytic shift reactor (R-1b) which is initially operated at 490° C. and allowed to stabilize over a period of about 125 hours. As can be seen from the plot, the carbon efficiency is near 100% and the $CH_3Br$ (MeBr) selectivity at the 490° C. initial operating temperature is approximately 80%. At about 140 hrs the catalytic shift reactor (R-1b) temperature is increased to 510° C., which increases the $CH_3Br$ selectivity to about 85%, and near 100% carbon efficiency is maintained. At about 155 hours the catalytic shift reactor (R-1b) temperature is increased to 520° C., which increases the CH3Br selectivity to about 88%, and near 100% carbon efficiency is maintained. At about 188 hours the catalytic shift reactor (R-1b) temperature is increased to 530° C., which increases the CH3Br selectivity to about 90%, and near 100% carbon efficiency is maintained. Subsequently, after about 200 hours, the catalytic shift reactor (R-1b) temperature is increased by approximate 10° C. increments, which gradually increases the $CH_3Br$ selectivity to a maximum of about 93% at about 570° C., and near 100% carbon efficiency is maintained. After about 220 hours, the catalytic shift reactor (R-1b) temperature is increased to 580° C., which does not cause a further increase in $CH_3Br$ selectivity, however a significant drop in carbon efficiency is noted, indicating that the optimum temperature for efficient reaction over the preferred catalyst is less than about 580° C.

The processes of the present invention are less expensive than conventional processes since the processes of the present invention operate at low pressures in the range of about 1 bar to about 30 bar and at relatively low temperatures in the range of about 20° C. to about 600° C. for the gas phase, and preferably about 20° C. to about 180° C. for the liquid phase. These operating conditions permit the use of less expensive equipment of relatively simple design that are constructed from readily available metal alloys, glass-lined, refractory/ceramic-lined equipment for the higher-temperature gas phase reactors and associated equipment and polymer-lined or glass-lined vessels, piping and pumps for the liquid phase-containing equipment. The processes of the present invention are also more efficient because less energy is required for operation and the production of excessive carbon dioxide as an unwanted byproduct is minimized. The reactors and process equipment utilized in the processes of the present invention may be of any suitable design as will be evident to a skilled artisan.

The processes of the present invention are capable of directly producing higher molecular weight hydrocarbons containing various molecular-weight components in the liquefied petroleum gas (LPG), olefin and motor gasoline fuels range that have substantial aromatic content thereby significantly increasing the octane value of the gasoline-range fuel components. These higher molecular weight hydrocarbons may be used directly as a product, as an intermediate product and/or as a feedstock for further processing depending upon the particular catalyst employed in and the operating parameters of the process. For example, the higher molecular weight hydrocarbons obtained by the processes of the present invention may be used directly as a motor gasoline fuel having a substantial aromatic content, as a fuel blending stock or as feedstock for further processing.

Where olefins are produced by the processes of the present invention, such olefins may be used as feed to a process for producing polyolefins.

While the foregoing preferred embodiments of the invention have been described and shown, it is understood that the alternatives and modifications, such as those suggested and others, may be made thereto and fall within the scope of the invention.

We claim:
1. A process comprising:
reacting bromine with gaseous alkanes containing methane at a first temperature from about 300° C. to about 600° C. sufficient to form bromination products comprising alkyl bromides; and
reacting said alkyl bromides with a portion of said methane in the presence of a catalyst and at a second temperature from about 500° C. to about 570° C. sufficient to convert at least a portion of poly-brominated alkanes present in said alkyl bromides to mono-brominated alkanes, wherein said catalyst is a metal halide, a metal oxyhalide or mixtures thereof and said metal is selected from Fe, Mo or mixtures thereof.

2. The process of claim 1 wherein said methane to bromine molar ratio in the contacting step greater than about 1.25:1 but less than 7:1.

3. The process of claim 2 wherein said methane to bromine molar ratio in the contacting step greater than about 1.5:1 but less than 4:1.

4. The process of claim 3 wherein said methane to bromine molar ratio in the contacting step greater than about 1.67:1 but less than 3:1.

5. The process of claim 1 wherein said second temperature is from about 530° C. to about 570° C.

6. The process of claim 1 wherein the steps of contacting and reacting are performed in separate reactors.

7. The process of claim 1 wherein the steps of contacting and reacting are performed in a reactor.

8. The process of claim 1 wherein said gaseous alkanes comprise at least 90 mol % methane.

9. The process of claim 1 wherein said gaseous alkanes contain from about 0.1 mol % to about 10 mol % $C_{2+}$ hydrocarbons.

10. The process of claim 1 wherein said gaseous alkanes contain less than about 0.2 mol % $C_{3+}$ hydrocarbons.

11. The process of claim 1 wherein said gaseous alkanes are sourced from natural gas, coal-bed methane, regasified liquefied natural gas, gas derived from gas hydrates and/or chlathrates, gas derived from anaerobic decomposition of organic matter or biomass, gas derived in the processing of tar sands, synthetically produced natural gas or alkanes, or mixtures of these sources.

12. The process of claim 1 wherein said gaseous alkanes are sourced from synthetically produced alkanes.

13. The process of claim 1 wherein said gaseous alkanes are sourced from synthetically produced natural gas.

14. The process of claim 1 wherein said gaseous alkanes are sourced from gas derived in the processing of tar sands.

15. The process of claim 1 further comprising:
reacting said alkyl bromides after the conversion of at least a portion of poly-brominated alkanes present in said alkyl bromides to mono-brominated alkanes in the presence of a second catalyst to form alkyl bromides.

16. The process of claim 1 wherein said bromination products further comprise hydrogen bromide, unreacted bromine and unreacted alkanes and said alkyl bromides are reacted with a portion of said methane in the further presence of said unreacted bromine and said unreacted alkanes.

* * * * *